United States Patent
Jeong et al.

(10) Patent No.: US 11,107,993 B2
(45) Date of Patent: Aug. 31, 2021

(54) ORGANIC COMPOUND AND ORGANIC ELECTROLUMINESCENT ELEMENT COMPRISING SAME

(71) Applicant: MATERIAL SCIENCE CO., LTD., Seoul (KR)

(72) Inventors: Jae Ho Jeong, Incheon (KR); Hyun Bin Kang, Gyeonggi-do (KR); Ji Woong Yoo, Busan (KR); Sang Hoon Hong, Seoul (KR); In Kyung Jeong, Seoul (KR)

(73) Assignee: Material Science Co., Ltd.

( * ) Notice: Subject to any disclaimer, the term of this patent is extended or adjusted under 35 U.S.C. 154(b) by 334 days.

(21) Appl. No.: 16/067,056

(22) PCT Filed: Dec. 29, 2016

(86) PCT No.: PCT/KR2016/015488
§ 371 (c)(1),
(2) Date: Jun. 28, 2018

(87) PCT Pub. No.: WO2017/116169
PCT Pub. Date: Jul. 6, 2017

(65) Prior Publication Data
US 2019/0006592 A1    Jan. 3, 2019

(30) Foreign Application Priority Data

Dec. 31, 2015 (KR) .................. 10-2015-0191309
Oct. 10, 2016 (KR) .................. 10-2016-0130598

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/54* (2013.01); *C07C 211/61* (2013.01);
(Continued)

(58) Field of Classification Search
None
See application file for complete search history.

(56) References Cited

U.S. PATENT DOCUMENTS

2004/0076853 A1    4/2004   Jarikov
2005/0048313 A1    3/2005   Sotoyama

FOREIGN PATENT DOCUMENTS

JP    2011-222831    11/2011
JP    2012-231136    11/2012
(Continued)

OTHER PUBLICATIONS

Brule et al., Superacid-Catalyzed Dimerization/Cylization of Isopropenyl-PAHs—Novel Pathways to PAH Dimers, Phenalenes and Their Stable Carbocations; Eur. J. Org. Chem, 2008, pp. 3700-3708 (Year: 2008).*

(Continued)

*Primary Examiner* — Gregory D Clark
(74) *Attorney, Agent, or Firm* — Sheridan Ross P.C.

(57) ABSTRACT

The present invention relates to an organic light-emitting diode (OLED) including a novel organic compound used in a light emitting layer thereof. Particularly, the present invention relates to an OLED including a novel pyrene-based organic compound.

8 Claims, 1 Drawing Sheet

(51) Int. Cl.
<table>
<tr><td>C09K 11/06</td><td>(2006.01)</td></tr>
<tr><td>C07C 211/54</td><td>(2006.01)</td></tr>
<tr><td>H05B 33/14</td><td>(2006.01)</td></tr>
<tr><td>C07C 255/58</td><td>(2006.01)</td></tr>
<tr><td>C07C 217/94</td><td>(2006.01)</td></tr>
<tr><td>C07C 233/07</td><td>(2006.01)</td></tr>
<tr><td>C07C 215/82</td><td>(2006.01)</td></tr>
<tr><td>C07C 215/88</td><td>(2006.01)</td></tr>
<tr><td>C07C 211/61</td><td>(2006.01)</td></tr>
<tr><td>C07C 217/92</td><td>(2006.01)</td></tr>
<tr><td>C07D 213/74</td><td>(2006.01)</td></tr>
<tr><td>C07D 307/91</td><td>(2006.01)</td></tr>
<tr><td>C07D 333/76</td><td>(2006.01)</td></tr>
<tr><td>C07F 7/08</td><td>(2006.01)</td></tr>
</table>

(52) U.S. Cl.
CPC .......... *C07C 215/82* (2013.01); *C07C 215/88* (2013.01); *C07C 217/92* (2013.01); *C07C 217/94* (2013.01); *C07C 233/07* (2013.01); *C07C 255/58* (2013.01); *C07D 213/74* (2013.01); *C07D 307/91* (2013.01); *C07D 333/76* (2013.01); *C07F 7/081* (2013.01); *C09K 11/06* (2013.01); *H01L 51/00* (2013.01); *H01L 51/0054* (2013.01); *H01L 51/50* (2013.01); *H05B 33/14* (2013.01); *C07C 2603/18* (2017.05); *C07C 2603/52* (2017.05); *C09K 2211/1007* (2013.01); *C09K 2211/1011* (2013.01); *C09K 2211/1014* (2013.01); *C09K 2211/1022* (2013.01); *H01L 51/0055* (2013.01); *H01L 51/0058* (2013.01); *H01L 51/0061* (2013.01); *H01L 51/0067* (2013.01); *H01L 51/0071* (2013.01); *H01L 51/0073* (2013.01); *H01L 51/0074* (2013.01); *H01L 51/0094* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/5384* (2013.01)

(56) References Cited

FOREIGN PATENT DOCUMENTS

| JP | 2013-045813 | 3/2013 |
|---|---|---|
| JP | 2015-174901 | 10/2015 |

OTHER PUBLICATIONS

Pospisil et al., Possibilities of the determination of alkylsubstituted polyaromatic hydrocarbons by LSC, GC/MS, and HPLC/UV techniques., 1998, Petroleum and Coal (1998), 40(3), 170-174 (STN Abstract Only) 2667-72 (Year: 1998).*

Clar et al., Aromatic hydrocarbons. LXV. Triangulene derivatives, Journal of the American Chemical Society (1953), 75, 2667-72 (Year: 1953).*

Engler et al. "Synthesis of peri-Cyclobutarenes by Thermolysis of [Methoxy(trimethylsilyl)methyl]arenes," The Journal of Organic Chemistry, Jun. 1999, vol. 62, No. 12, pp. 4247-4254.

Minabe et al. "Electrophilic Substitution of 3,4-Dihydrocyclopenta(cd)pyrene and the 3-Ketone," Bulletin of the Chemical Society of Japan, Apr. 1993, vol. 66, No. 4, pp. 1248-1253.

Sarobe et al. "Triscyclopenta[cd,fg,jk]pyrene: another congener of the externally cyclopenta-fused pyrene series," Chemical Communications, 1999, No. 11, pp. 1021-1022.

Van Het Goor et al. "π-dimerization of pleiadiene radical cations at low temperatures revealed by UV-vis spectroelectrochemistry and quantum theory," Journal of Solid State Electrochemistry, Oct. 2011, vol. 15, No. 10, pp. 2107-2117.π

International Search Report prepared by the Korean Intellectual Property Office dated Apr. 14, 2017, for International Application No. PCT/KR2016/015488.

CAS Registry No. 7130-15-6, Nov. 16, 1984, 5 pages.

CAS Registry No. 224183-39-5, Jun. 4, 1999, 4 pages.

Chemical Abstract Compound, STN express. RN 224813-39-5, Jun. 4, 1999, 1 page.

Brule et al. "Superacid-Catalyzed Dimerization/Cyclization of Isopropenyl-PAHs—Novel Pathways to PAH Dimers, Phenalenes and Their Stable Carbocations," Eur. J. Org. Chem., 2008, vol. 2008, No. 21, pp. 3700-3708.

Sugimoto et al. "Evaluation of Recycle Solvent Qualities for Coal Liquefaction by GC/MS-chromatograms," Journal of the Japan Institute of Energy, 1996, vol. 75, No. 2, pp. 93-98 (English abstract).

Tucker et al. "Effect that Various Electron Donating and Electron Withdrawing Functional Groups have Regarding Nitromethane's Ability to Selectively Quench Fluorescence Emission of Alternant Polycyclic Aromatic Hydrocarbons," Polycyclic Aromatic Compounds, 1994, vol. 4, pp. 141-160.

* cited by examiner

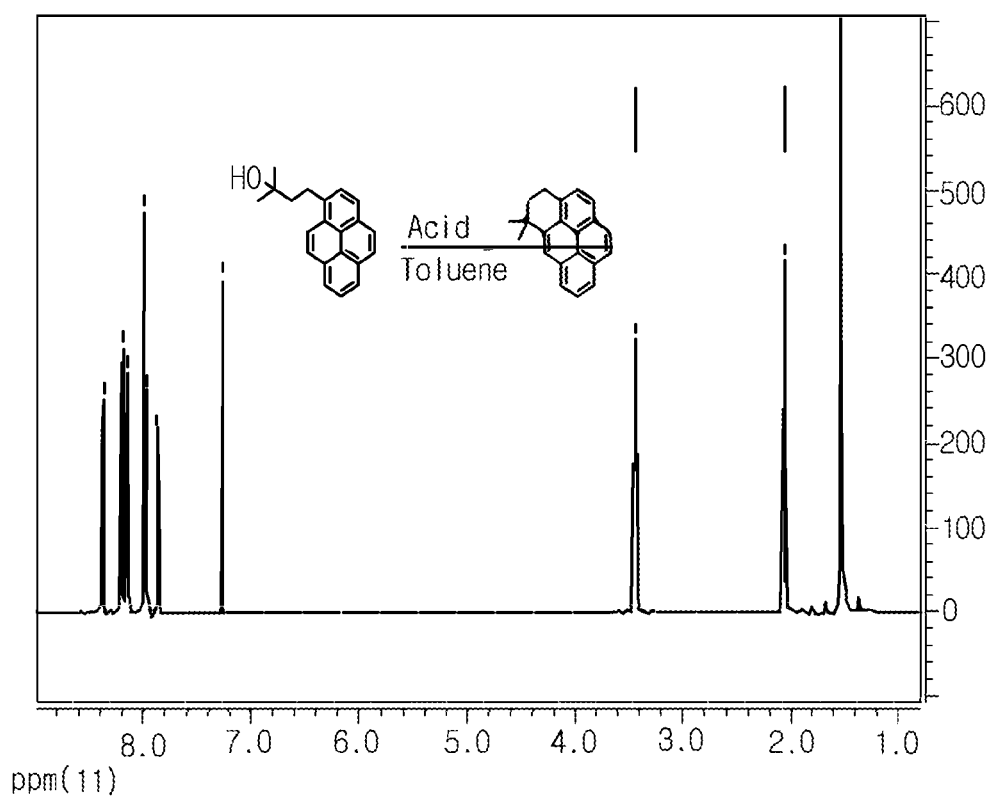

ORGANIC COMPOUND AND ORGANIC ELECTROLUMINESCENT ELEMENT COMPRISING SAME

CROSS REFERENCE TO RELATED APPLICATIONS

This application is a national stage application under 35 U.S.C. 371 and claims the benefit of PCT Application No. PCT/KR2016/015488 having an international filing date of 29 Dec. 2016, which designated the United States, which PCT application claimed the benefit of the Republic of Korea Application No. 10-2015-0191309 filed 31 Dec. 2015, and the Republic of Korea Application No. 10-2016-0130598 filed 10 Oct. 2016, the disclosure of each of which are incorporated herein by reference.

TECHNICAL FIELD

The present invention relates to a novel organic compound used in an organic light-emitting diode and an organic light-emitting diode including the same. Particularly, the present invention relates to a novel pyrene-based organic compound and an organic light-emitting diode using the same.

BACKGROUND ART

Since a first organic electroluminescent diode was developed using an aromatic diamine as a light emitting layer and an aluminum compound at Eastman Kodak by C. W. Tang in 1987 (C. W. Tang, S. A. Vanslyke, Applied Physics Letters, Vol. 51, 1987, 913), a variety of studies on a multilayer thin film-type OLED and an organic material therefor have been actively conducted. An OLED is being actively developed to be used as a backlight for flat panel displays such as a wall-mounted TV or other displays, a light source for lighting equipment or advertising boards, etc. due to a simple structure, various advantages in a manufacturing process, high brightness, a wide viewing angle, a fast response speed, and a low driving voltage, compared with the existing other flat panel displays, such as a liquid crystal display (LCD), a plasma display panel (PDP) and a field emission display (FED).

Generally, an OLED is a diode emitting light by combining holes with electrons in a light emitting layer when a voltage is applied to a cathode (electron injection electrode) and an anode (hole injection electrode), and has a structure including a plurality of organic layers between both electrodes. Here, the OLED may include a hole injection layer (HIL), a hole transport layer (HTL), an electron transport layer (ETL) or an electron injection layer (EIL), in addition to a light emitting layer (EML), and to increase the efficiency of the EML, the OLED may further include an electron blocking layer (EBL) or a hole blocking layer (HBL) when needed. The OLED including all of the organic layers mentioned above has a structure in which an anode /HIL/ HTL/EBL/EML/HBL/ETL/EIL/a cathode are laminated.

Most of the materials used in an OLED are pure organic materials or complex compounds made of an organometallic complex between an organic material and a metal, and may be classified into a hole injection material, a hole transport material, a light emitting material, an electron transport material, and an electron injection material according to its intended use. Here, as a hole injection material or a hole transport material, an organic material having relatively low ionization energy is mainly used, and as an electron injection material or an electron transport material, an organic material having relatively high electronegativity is mainly used. In addition, a material used as an auxiliary EML preferably satisfies the following properties.

First, materials used in an OLED preferably have excellent thermal stability. This is because Joule heating occurs due to movement of charges in the OLED. At present, since TPD or NPB, which is mainly used as a HTL material, has a low glass transition temperature (Tg) of 60 or 96° C., respectively, when the OLED is driven at a high temperature, due to crystallization, light emitting efficiency may be reduced.

Second, for low-voltage driving, organic materials adjacent to a cathode and an anode are necessarily designed to have a lower charge injection barrier, and necessarily have high charge mobility.

Third, there is always an energy barrier at the interface between an electrode and an organic layer, or between organic layers, and a part of charges are indispensably accumulated. For this reason, materials having excellent electrochemical stability have to be used.

The EML consists of two materials, a host and a dopant, wherein the dopant necessarily has high quantum efficiency, and the host has a larger energy gap than the dopant, thereby facilitating energy transfer to the dopant. A display used in a TV or mobile realizes full color with three colors of red, green and blue, and each EML consists of red host/dopant, green host/dopant or blue host/dopant. Until now, the blue EML has the greatest inferiority in terms of a lifespan, efficiency and colorimetric purity with respect to other color EMLs.

As a material used as a blue dopant, perylene, coumarine, anthracene, or pyrene may be used, and these fluorescent compounds are used in various fields such as photocatalyst, semiconductor, charge transport, crystallographic, carbon nanotube (CNT), DNA probe, and dendrimer fields. Particularly, pyrene-based compounds are actively applied to blue EMLs due to a smaller full width at half maximum (FWHM) of an emission wavelength than other materials. While blue light emitting OLEDs using such pyrene-based compounds have been disclosed in U.S. Pat. No. 7,233,019, Korean Unexamined Patent Application Publication Nos. 2006-0006760, 2003-0054519, 2005-0101026, 2006-7023411, 2008-0123423, 2008-0133717, 2002-0066342, 2005-7005834, 2005-7017372, 2006-7023676, 2006-7024933, 2007-7005909, 2007-0140174, 2009-0071884, and 2009-0124172, there is a consistent demand for the development of a material having high quantum efficiency and capable of realizing deep blue color. Particularly, for RGB pixelation, a solution process such as an ink-jet method has been used, and to this end, there is an urgent demand for the development of a material with excellent solubility.

DISCLOSURE

Technical Problem

The present invention is for solving the above-mentioned problems by introducing a cyclized alkyl group in a pyrene molecule, and designing the molecule in an asymmetrical design.

The present invention is directed to providing a novel organic compound, which weakens the π-π interaction between molecules to facilitate sublimation and deposition of a material at a low temperature and has a shorter maximum emission wavelength than a conventional compound, thereby realizing a deeper blue color.

The present invention is also directed to providing an organic compound, which interrupts the formation of an excimer of a pyrene molecule and increases the electron density of a core and the stability of a dopant, thereby enabling an increase in the efficiency and lifespan of a diode.

The present invention is also directed to providing an organic compound, which solves the productivity and cost problems of the conventional blue dopant material in a process by improving solubility in a solution, and facilitates the realization of a diode even in a solution process, not a deposition process that is necessarily performed in a conventional OLED process.

The present invention is also directed to providing a deep blue-like blue host/dopant system, which is suitable for an AM-OLED.

The present invention is also directed to providing an OLED using the organic compound.

Technical Solution

In one exemplary embodiment of the present invention, the present invention provides a novel organic compound represented by Formula 1 below.

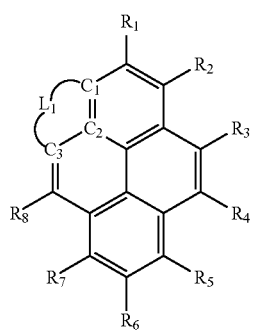

[Formula 1]

Here, $L_1$ includes $C_1$, $C_2$ and $C_3$ to form a saturated or unsaturated ring having 4 to 7 carbon atoms, and the ring may be substituted with alkyl having 1 to 10 carbon atoms, $R_1$ to $R_8$ are the same or different, and each independently selected from the group consisting of hydrogen, deuterium, a halogen, a nitro group, a cyano group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted cycloalkyl group having 3 to 30 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 6 to 30 carbon atoms, a substituted or unsubstituted heteroarylalkyl group having 6 to 30 carbon atoms, a substituted or unsubstituted alkylsilyl group having 1 to 30 carbon atoms, a substituted or unsubstituted arylsilyl group having 6 to 30 carbon atoms and a substituted or unsubstituted aryloxy group having 6 to 30 carbon atoms, and the substituents of $R_1$ to $R_8$ are the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms.

In another exemplary embodiment of the present invention, the present invention may provide an OLED, which includes a first electrode; a second electrode opposite to the first electrode; and one or more organic layers interposed between the first electrode and the second electrode, wherein the one or more organic layers include one or more organic compounds represented by Formula 1.

Advantageous Effects

An organic compound according to the present invention is a blue dopant material that shifts an emission wavelength to a 7 nm or more shorter wavelength than a conventional blue dopant, and thus a deep blue host/dopant system suitable for an AM-OLED can be manufactured.

A blue host/dopant system with a longer lifespan can be provided by introducing a cyclized alkyl group in a pyrene molecule and reducing the symmetry of the molecule.

The organic compound according to the present invention has properties suitable for the reduction of costs for a production process and manufacture of an OLED by improving solubility in a solution.

The OLED manufactured using the organic compound of the present invention realizes a diode with excellent colorimetric purity and high efficiency.

DESCRIPTION OF DRAWINGS

FIG. 1 is an NMR result for Intermediate A.

MODES OF THE INVENTION

In an exemplary embodiment of the present invention, a novel organic compound represented by Formula 1 below is provided.

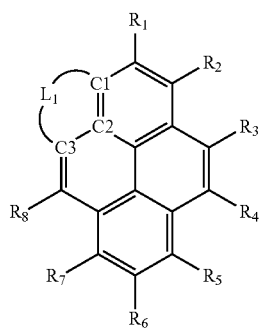

[Formula 1]

Here, $L_1$ includes $C_1$, $C_2$ and $C_3$ to form a saturated or unsaturated ring having 4 to 7 carbon atoms, and the ring may be substituted with alkyl having 1 to 10 carbon atoms, $R_1$ to $R_8$ are the same or different, and each independently selected from the group consisting of hydrogen, deuterium, a halogen, a nitro group, a cyano group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted cycloalkyl group having 3 to 30 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 6 to 30 carbon atoms, a substituted or unsubstituted heteroarylalkyl group having 6 to 30 carbon atoms, a substituted or unsubstituted alkylsilyl group having 1 to 30 carbon atoms, a substituted or unsubstituted arylsilyl group having 6 to 30 carbon atoms and a substituted or unsubstituted aryloxy group having 6 to 30 carbon atoms, and the substituents of $R_1$ to $R_8$ are the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms.

In another exemplary embodiment of the present invention, a material for forming an EML, which includes the organic compound represented by Formula 1 below, is provided.

In one exemplary embodiment of the present invention, the compound of Formula 1 may be an organic compound represented by Formula 2.

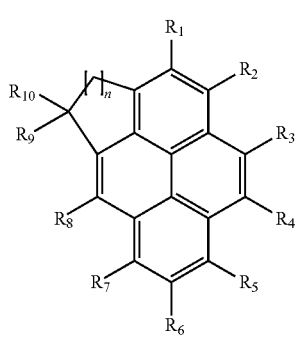

[Formula 2]

Here, $R_1$ to $R_8$ are defined in Formula 1, n is an integer of 1 to 3, $R_9$ and $R_{10}$ are the same or different, and each independently selected from the group consisting of hydrogen, a substituted or unsubstituted alkyl group having 1 to 10 carbon atoms, a substituted or unsubstituted cycloalkyl group having 3 to 12 carbon atoms, a substituted or unsubstituted alkoxy group having 1 to 10 carbon atoms, a halogen, a cyano group, a substituted or unsubstituted alkylsilyl group having 1 to 30 carbon atoms and a substituted or unsubstituted arylsilyl group having 6 to 30 carbon atoms, the substituents of $R_9$ and $R_{10}$ may be the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms and a heteroalkyl group having 2 to 30 carbon atoms.

According to an exemplary embodiment of the present invention, the compound represented by Formula 1 may be a compound represented by Formula 13 below:

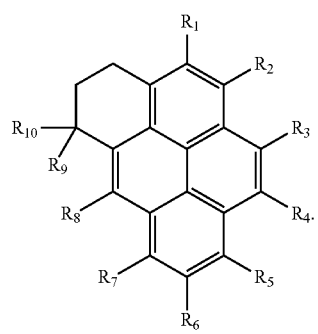

[Formula 13]

Here, $R_1$ to $R_{10}$ are defined in Formula 1 and Formula 2.

In an exemplary embodiment of the present invention, any one of $R_1$ to $R_8$ may be a functional group represented by Formula 3 below:

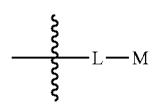

[Formula 3]

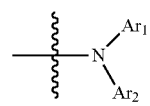

[Formula 4]

Here, L is a single bond, a substituted or unsubstituted arylene group having 6 to 8 carbon atoms or a substituted or unsubstituted heteroarylene group having 6 to 18 carbon atoms, M is hydrogen, deuterium or a functional group represented by Formula 4 as shown above, $Ar_1$ and $Ar_2$ may be each independently selected from the group consisting of hydrogen, deuterium, a halogen, a cyano group, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 6 to 30 carbon atoms, a substituted or unsubstituted alkylsilyl group having 1 to 30 carbon atoms and a substituted or unsubstituted arylsilyl group having 6 to 30 carbon atoms, and $Ar_1$ and $Ar_2$ are connected to each other, thereby forming a 6- to 18-membered ring including one or more N, O or S, and the substituents of L, $Ar_1$ and $Ar_2$ may be the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms.

According to an exemplary embodiment of the present invention, $Ar_1$ and $Ar_2$ may be a substituent selected from the group consisting of the compounds represented by Formula 5 to 10, but the present invention is not limited thereto:

[Formula 5]

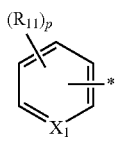

[Formula 6]

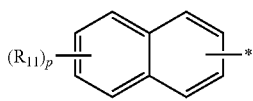

[Formula 7]

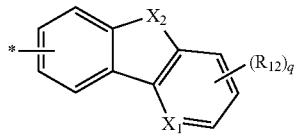

[Formula 8]

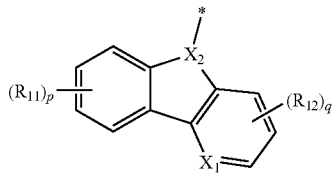

[Formula 9]

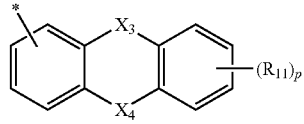

[Formula 10]

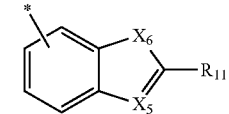

Here, * is a site where a bond is formed, p is an integer of 0 to 4, q is an integer of 0 to 3, $X_1$ is selected from the group consisting of $C(R_{13})$, N, S and O, $X_2$, $X_3$, $X_4$ and $X_6$ are the same or different, and each independently selected from the group consisting of $C(R_{13})(R_{14})$, $N(R_{13})$, S and O, $X_5$ and $X_7$ are the same or different, and each independently selected from the group consisting of $C(R_{13})$ and N, $R_{11}$ to $R_{14}$ are the same or different, and each independently selected from the group consisting of hydrogen, deuterium, a halogen, a cyano group, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 6 to 30 carbon atoms, a substituted or unsubstituted alkylsilyl group having 1 to 30 carbon atoms and a substituted or unsubstituted arylsilyl group having 6 to 30 carbon atoms, and the substituents of $R_{11}$ to $R_{14}$ may be the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms.

According to an exemplary embodiment of the present invention, $Ar_1$ and $Ar_2$ may be linked with N of M, thereby forming a ring, and the resulting compound may be a compound represented by Formula 11 or 12 below, but the present invention is not limited thereto:

[Formula 11]

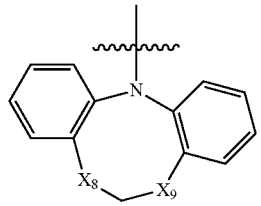

[Formula 12]

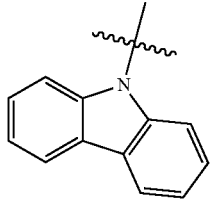

Here, $X_8$ and $X_9$ are the same or different, and each independently selected from the group consisting of $C(R_{15})(R_{16})$, $N(R_{15})$, S and O, $R_{15}$ and $R_{16}$ are the same or different, and each independently selected from the group consisting of hydrogen, deuterium, a halogen, a cyano group, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 6 to 30 carbon atoms, a substituted or unsubstituted alkylsilyl group having 1 to 30 carbon atoms and a substituted or unsubstituted arylsilyl group having 6 to 30 carbon atoms, and the substituents of $R_{15}$ and $R_{16}$ may be the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms.

According to an exemplary embodiment of the present invention, the compound represented by Formula 1 may be selected from the group consisting of the following compounds:

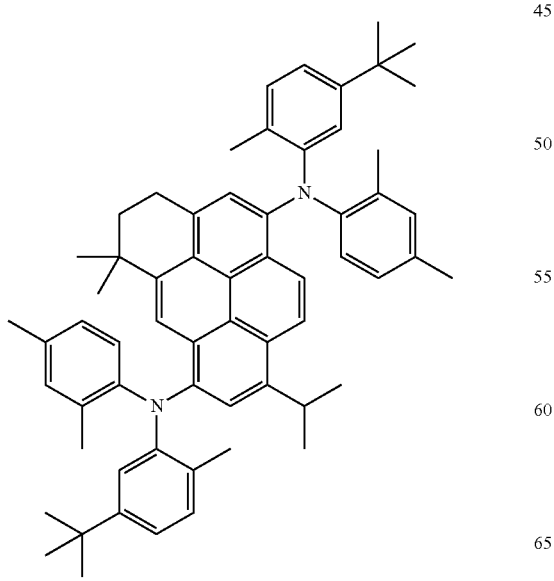

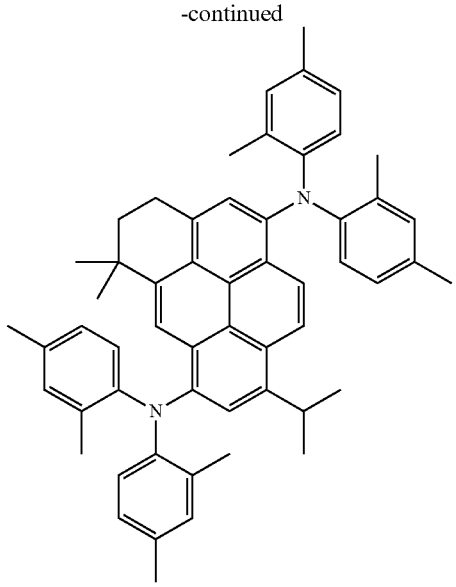

-continued

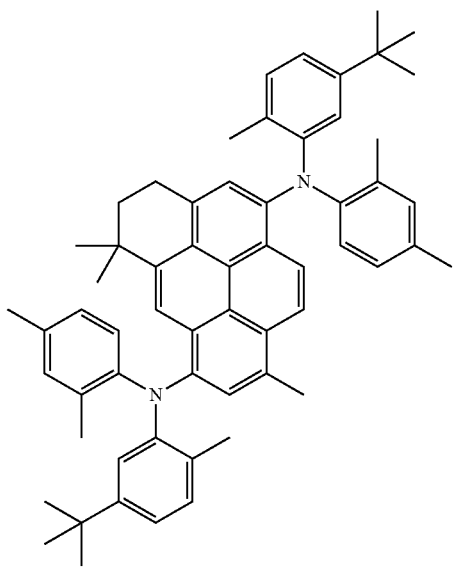

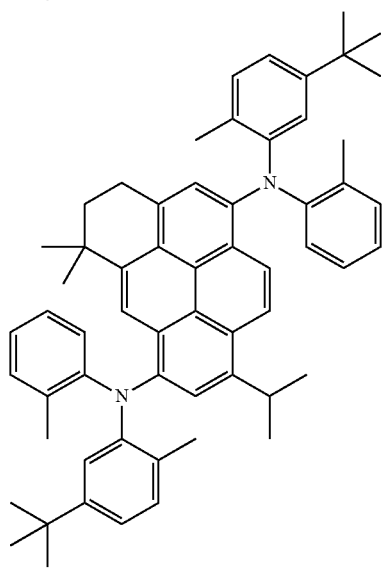

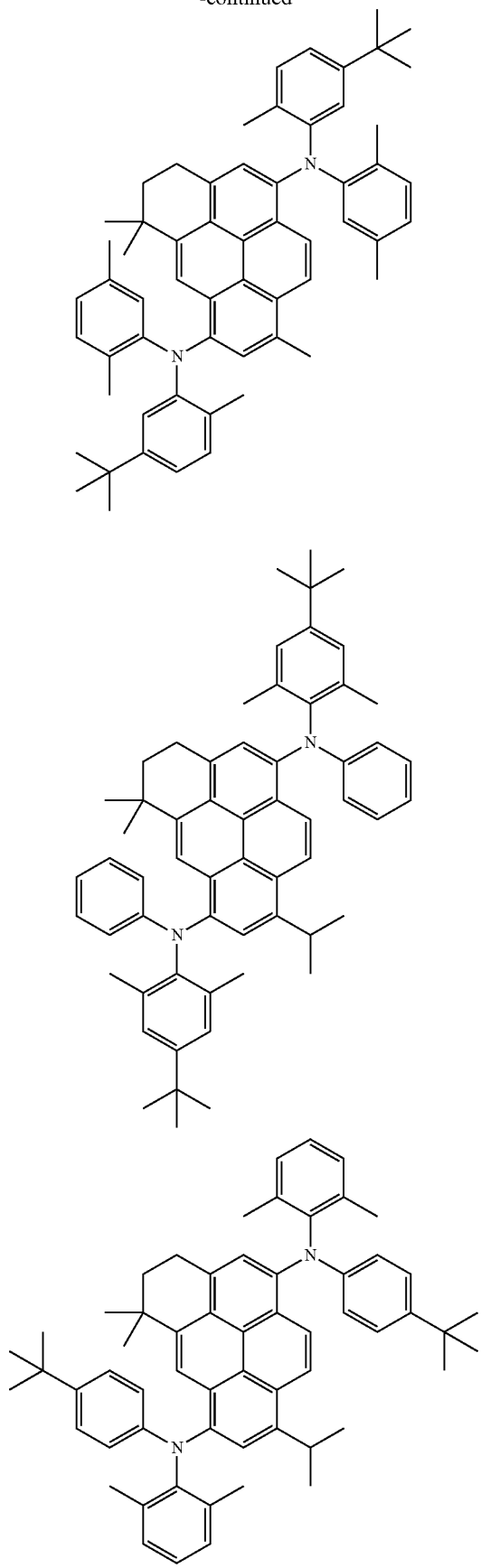
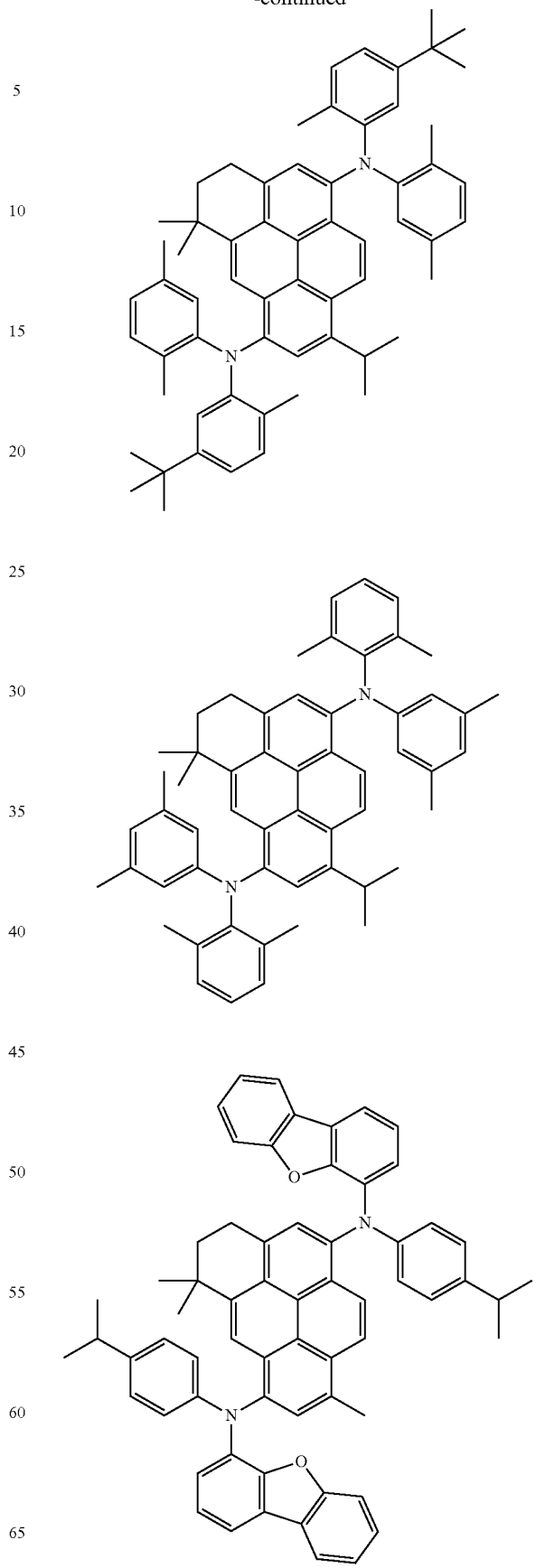

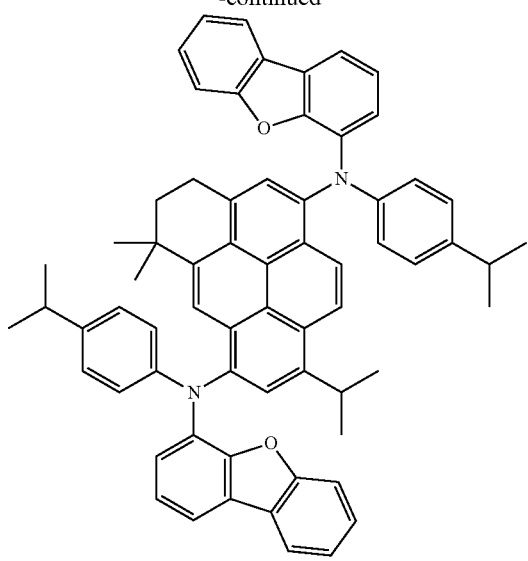
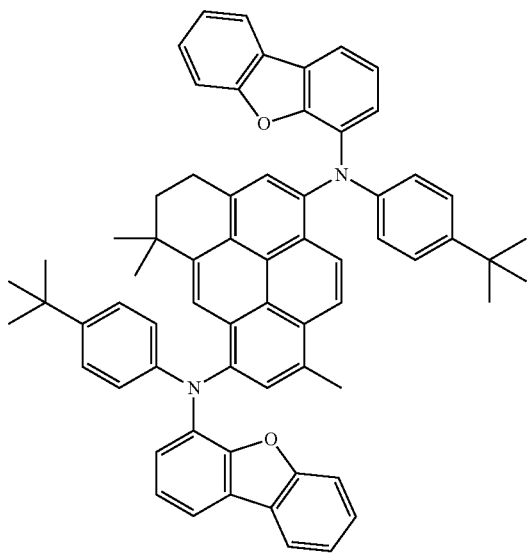
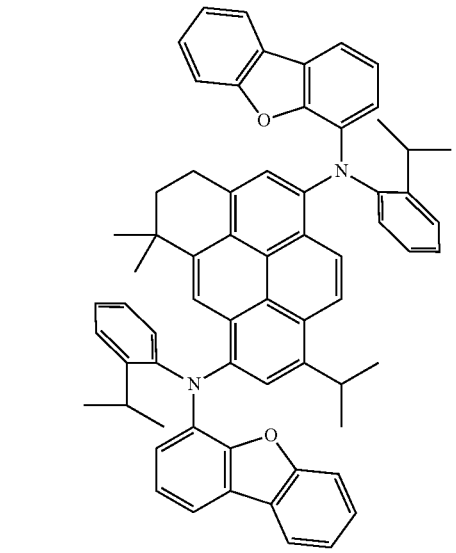
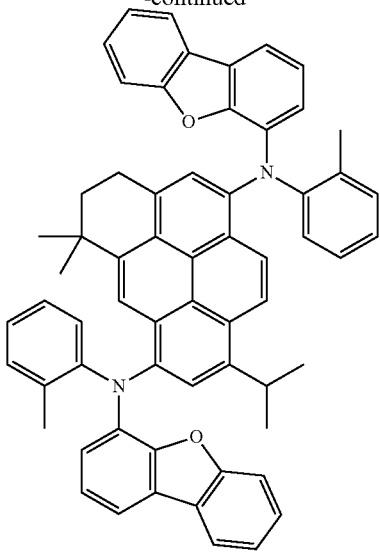
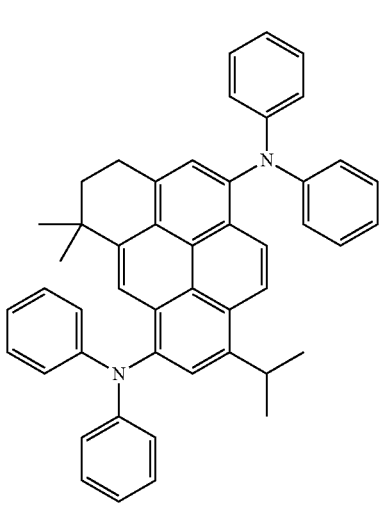
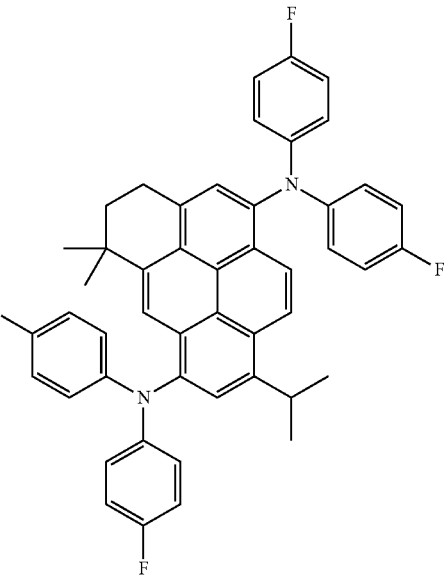

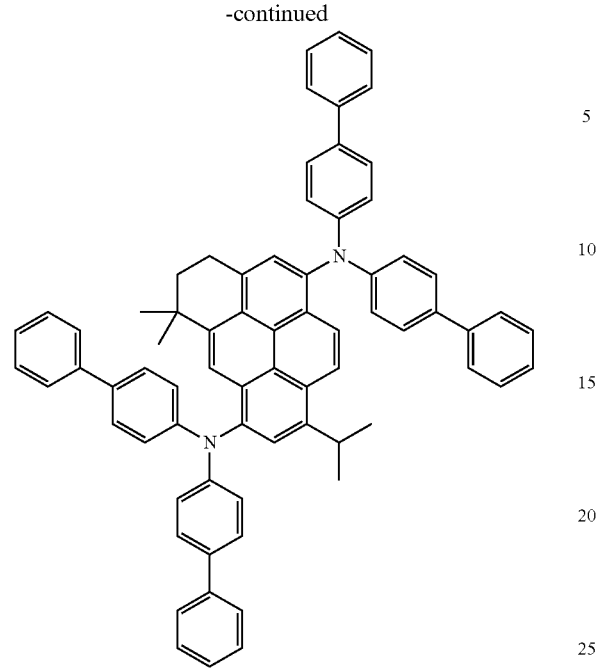
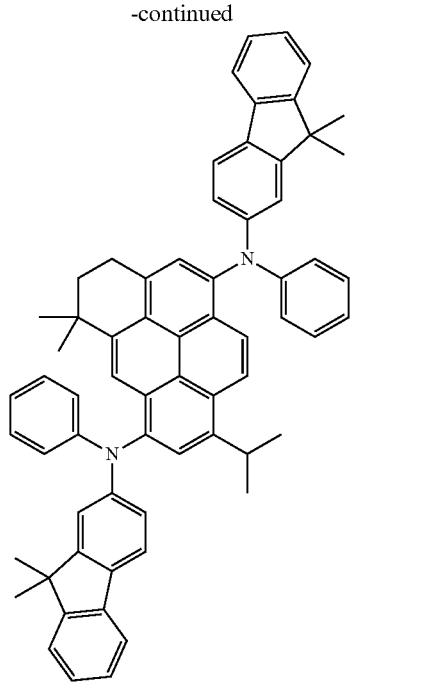
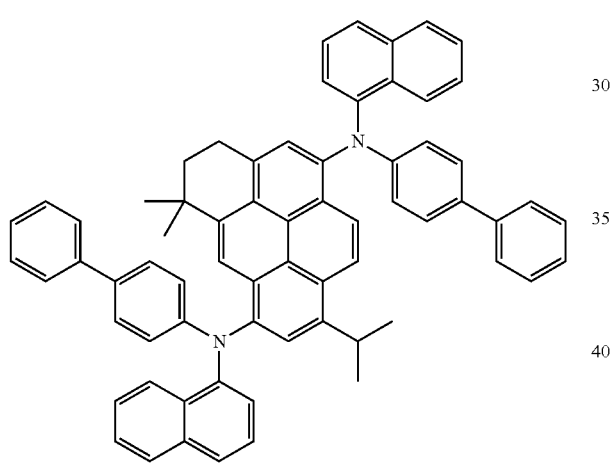
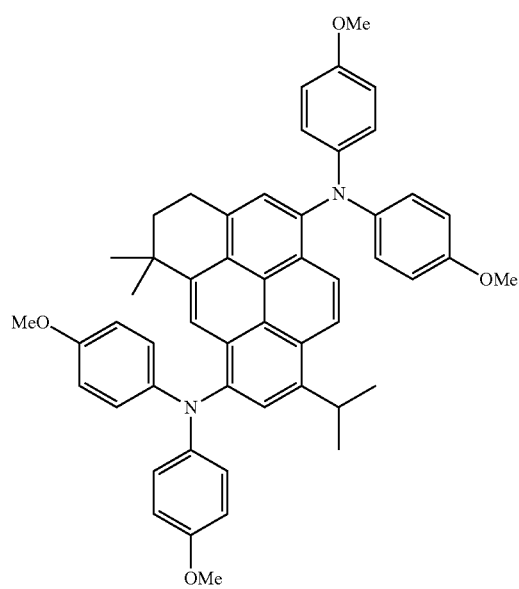
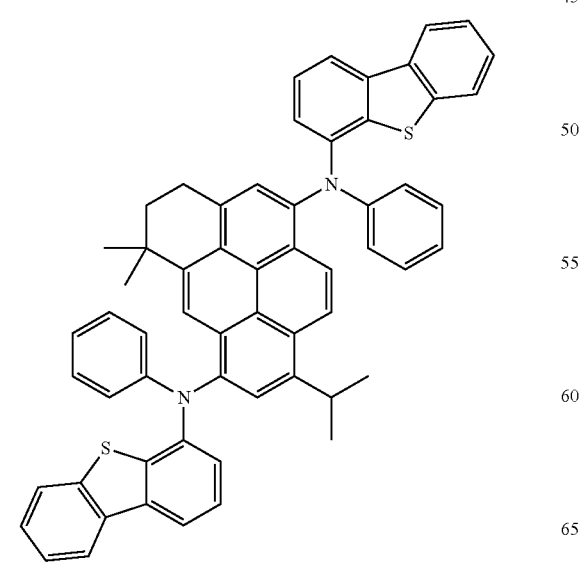
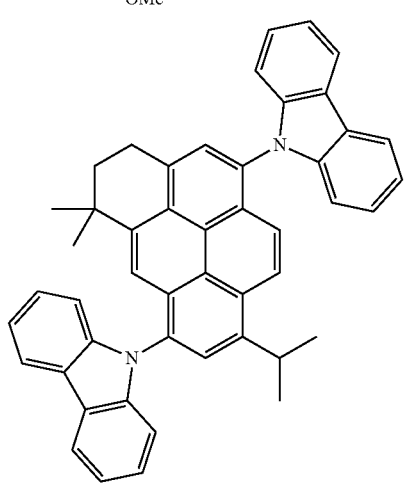

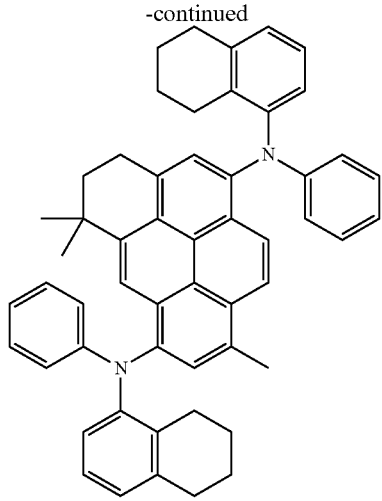
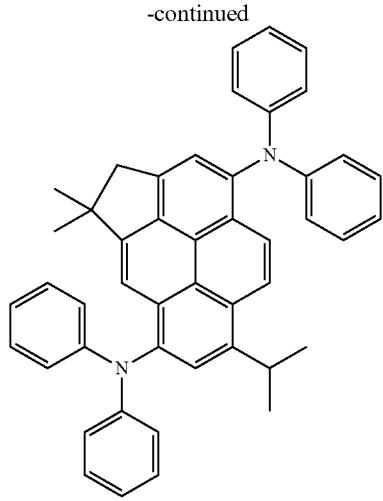
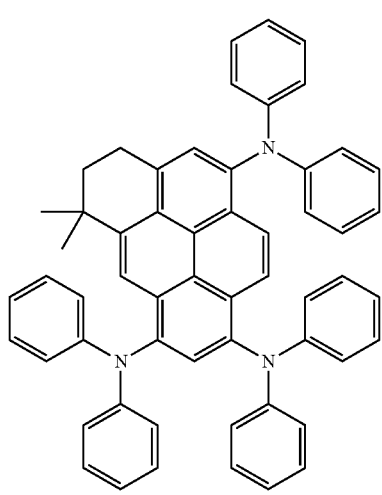
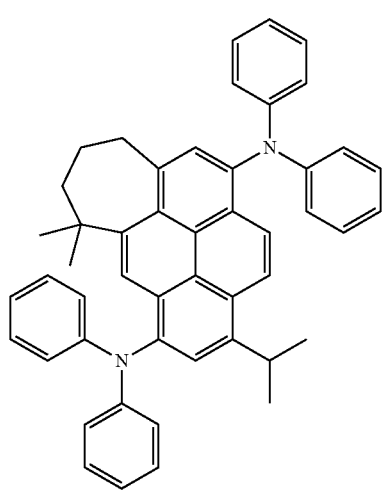
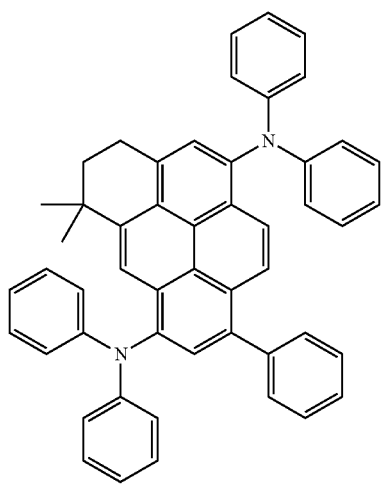
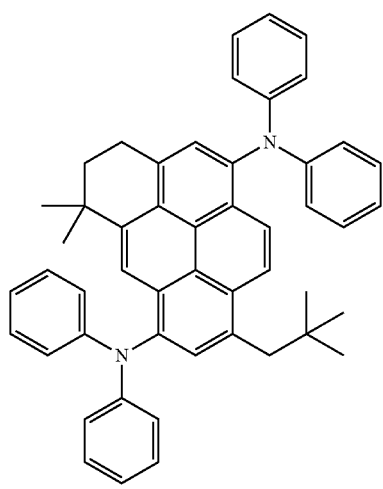

-continued
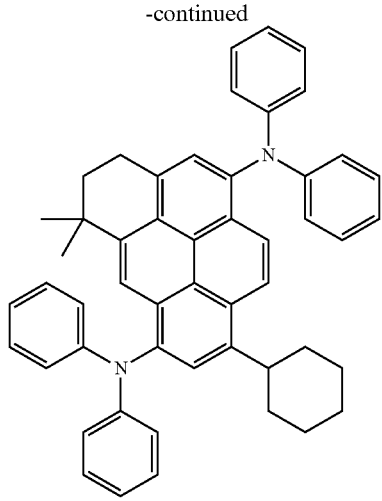
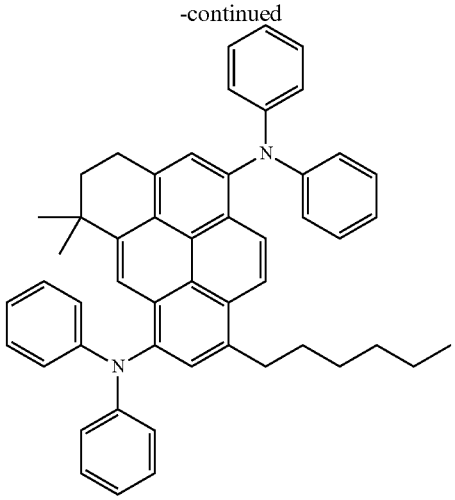
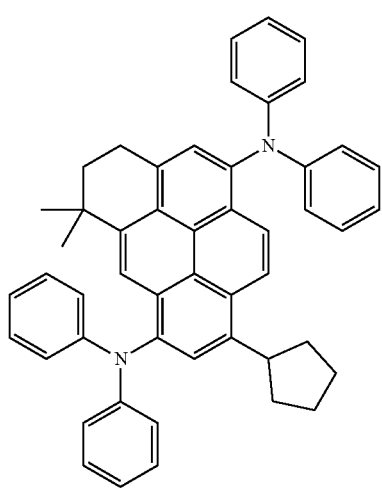
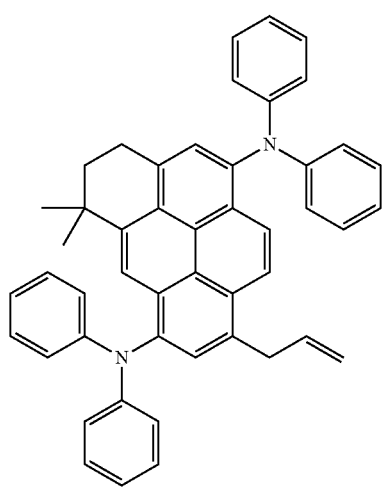
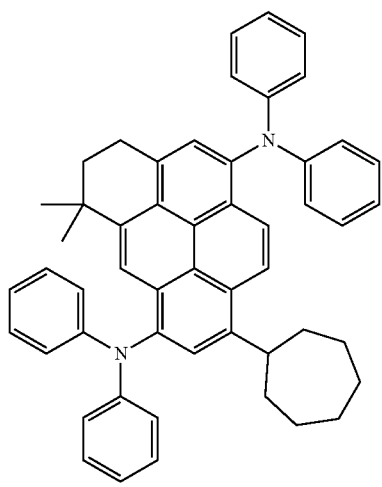
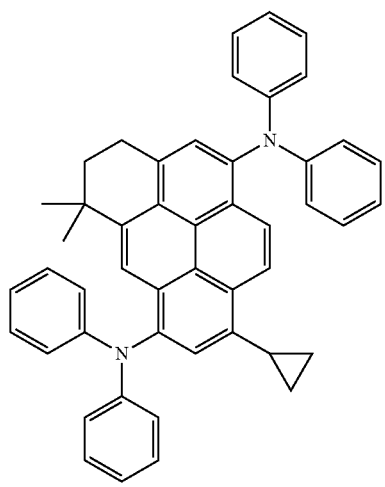

21
-continued
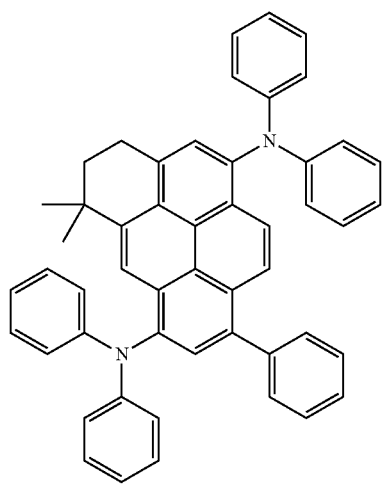
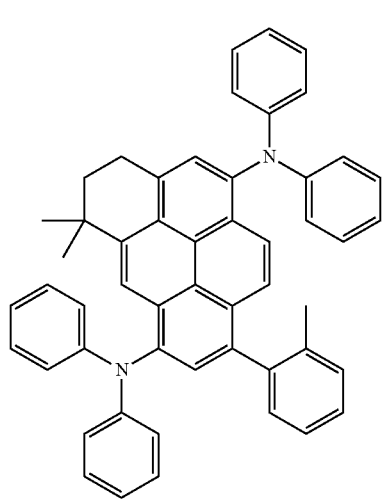
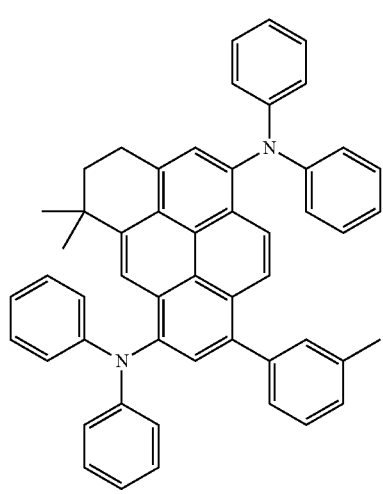
22
-continued
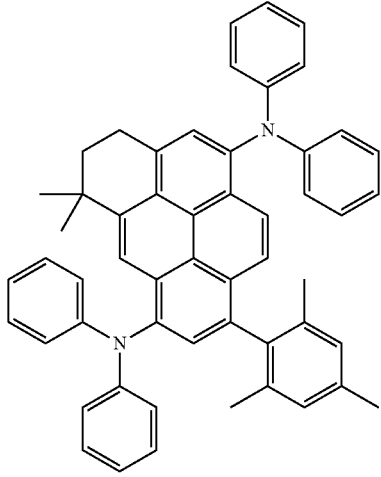
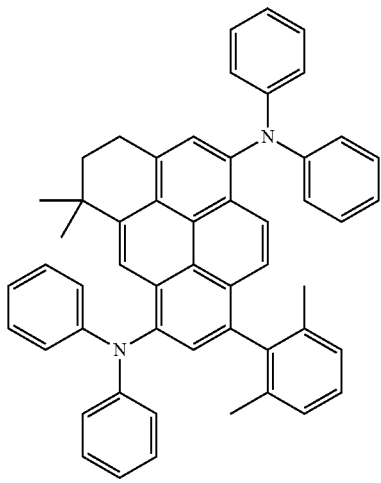
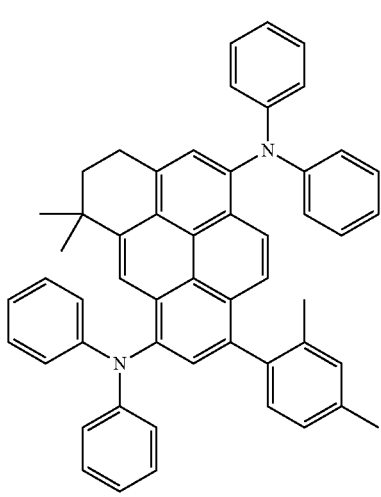

23
-continued
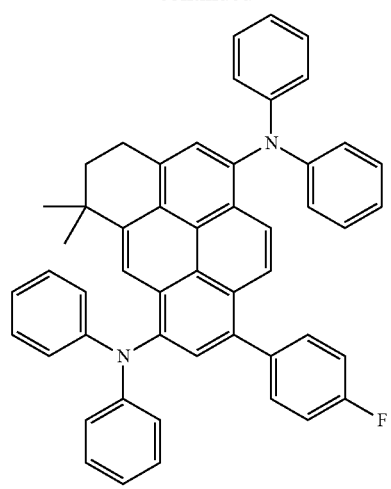
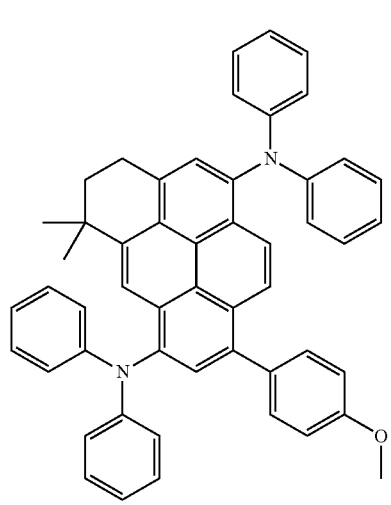
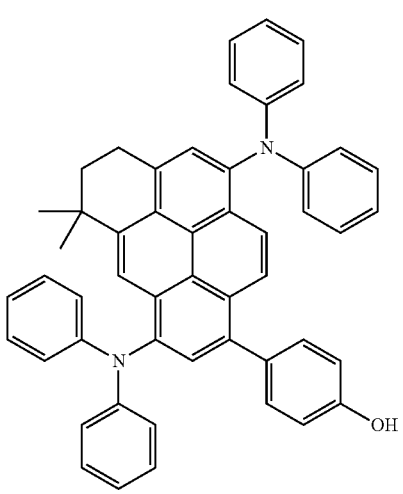
24
-continued
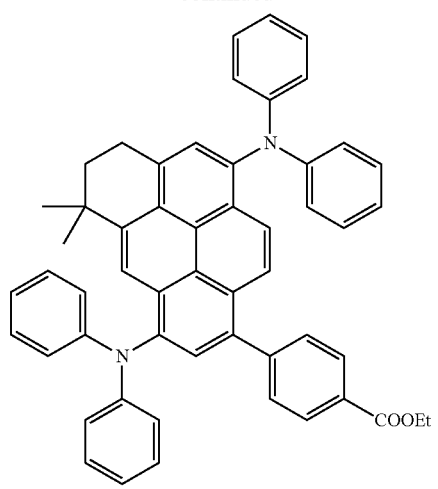
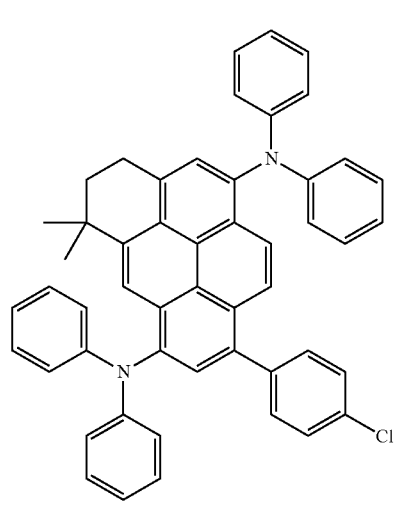
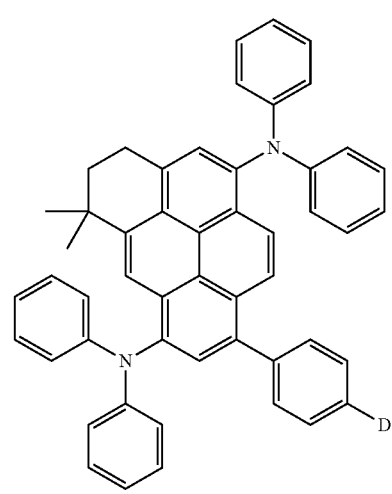

-continued
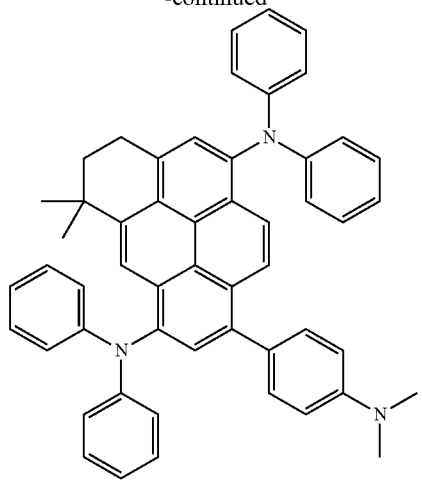
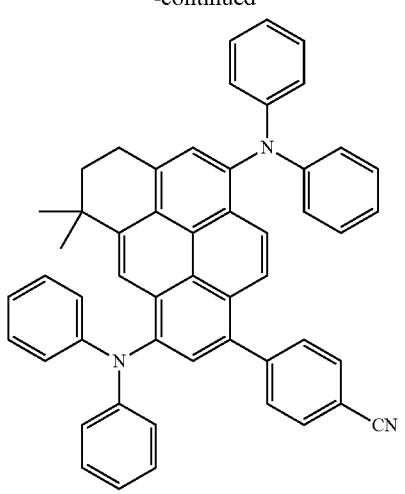
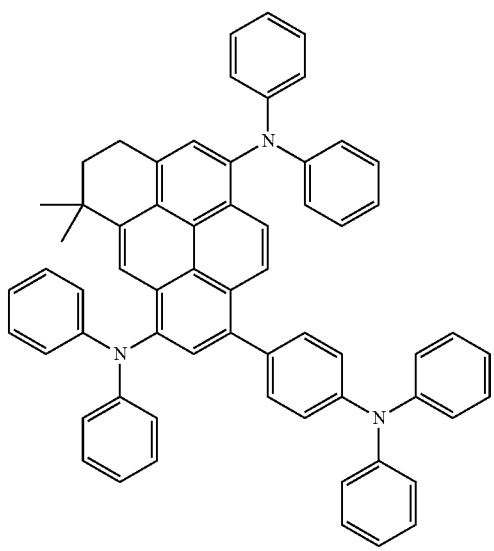
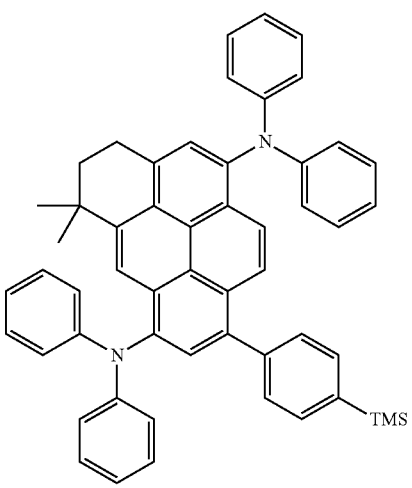
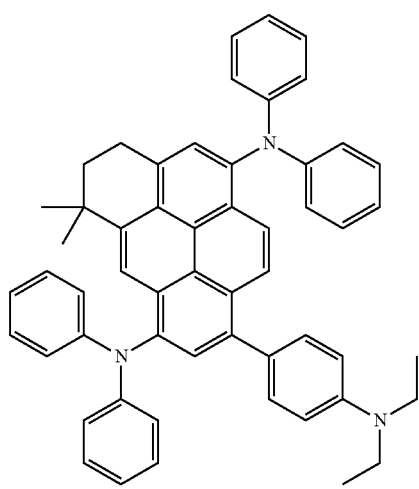
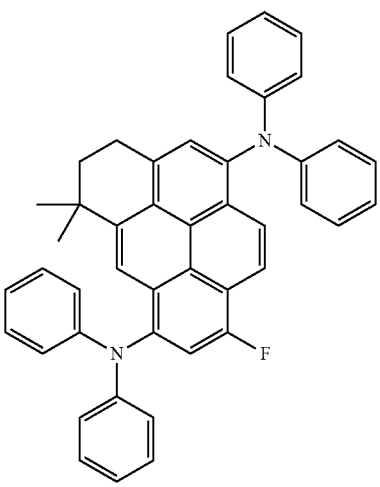

27
-continued
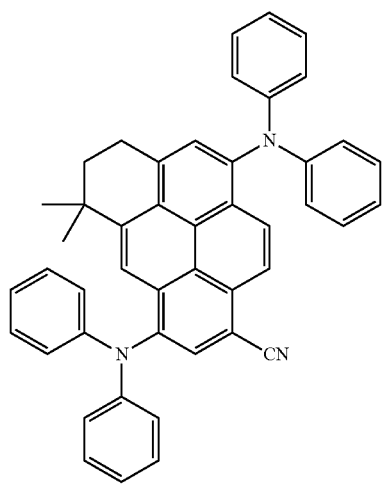
28
-continued
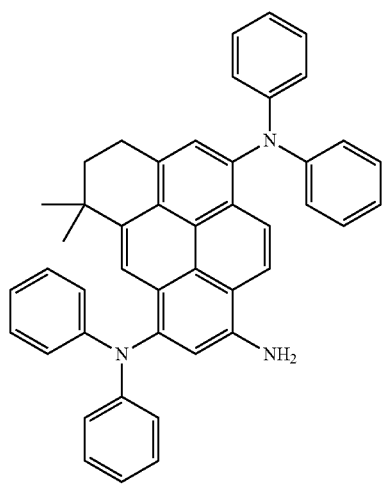
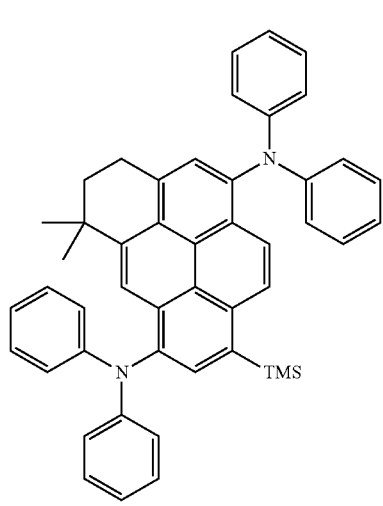
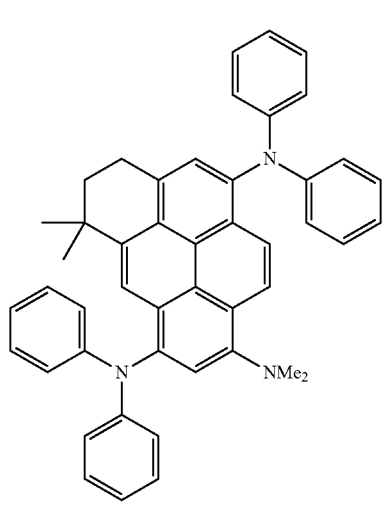
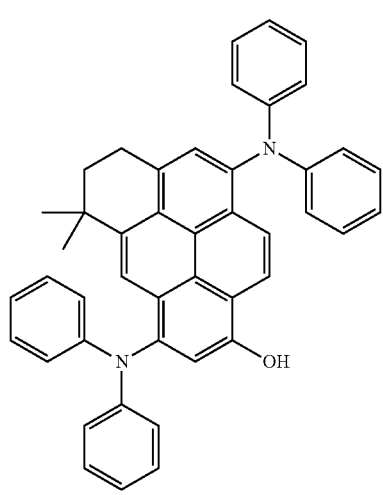
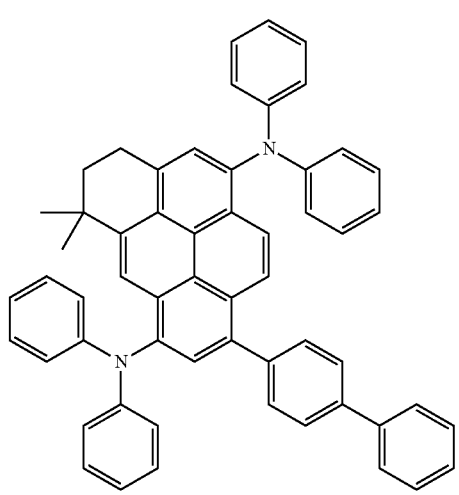

-continued
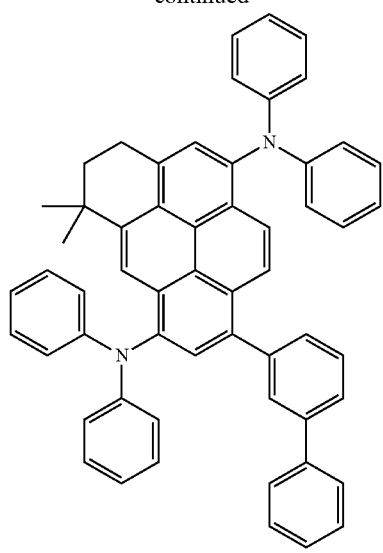
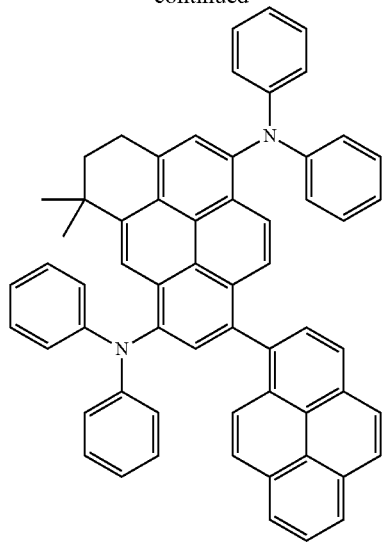
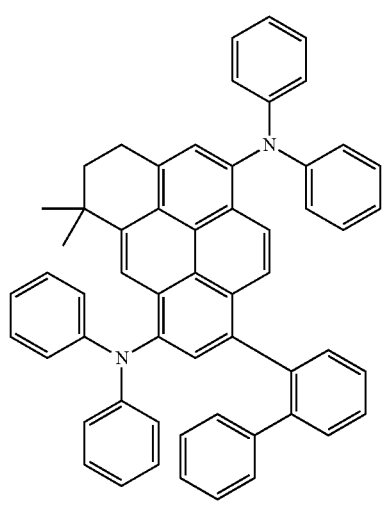
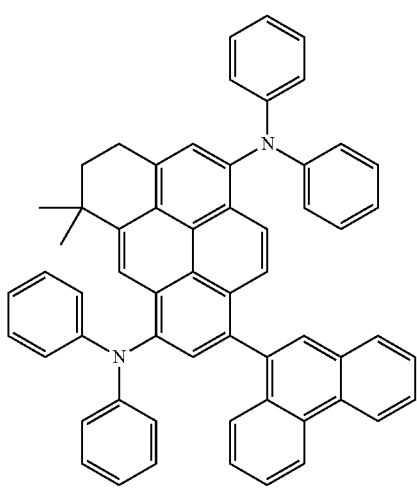
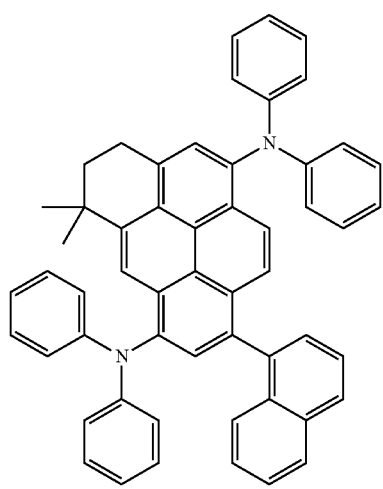
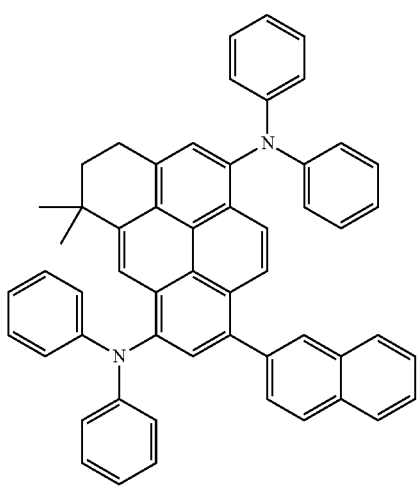

31
-continued
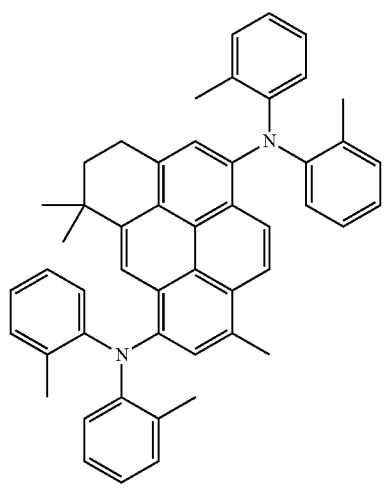
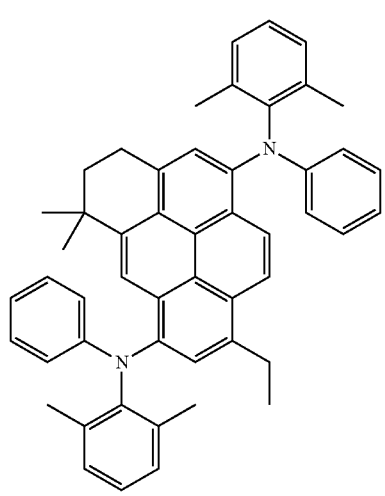
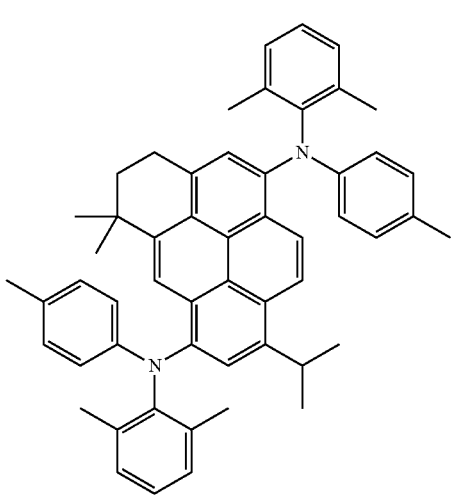
32
-continued
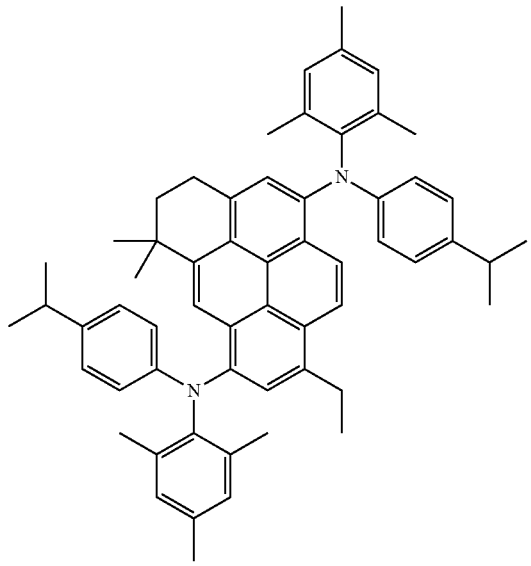
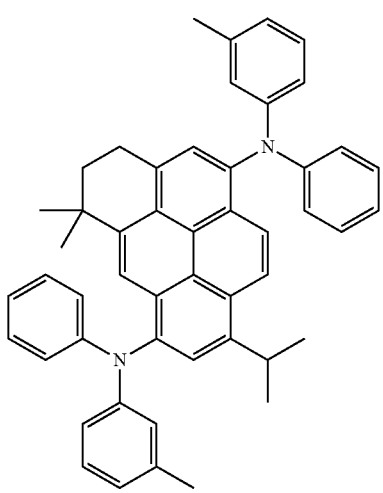
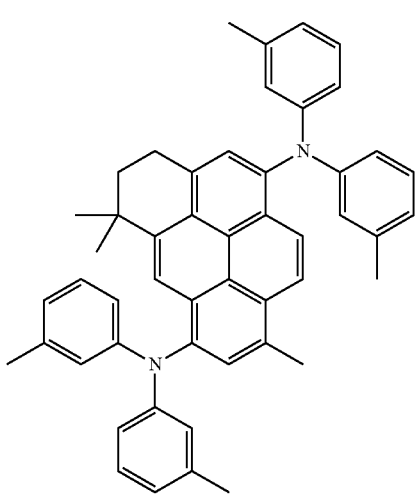

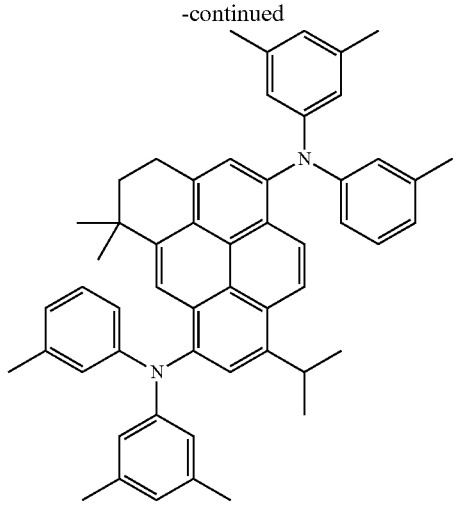
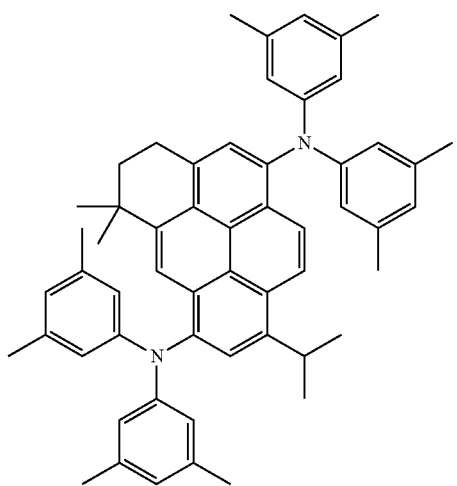
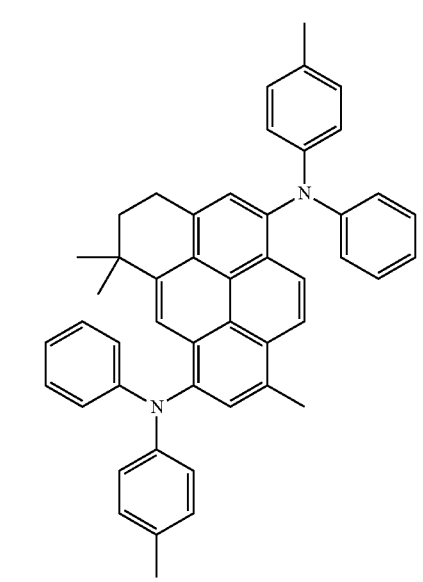
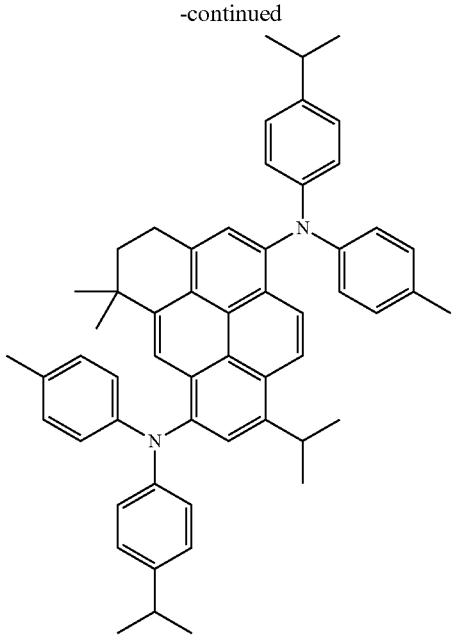
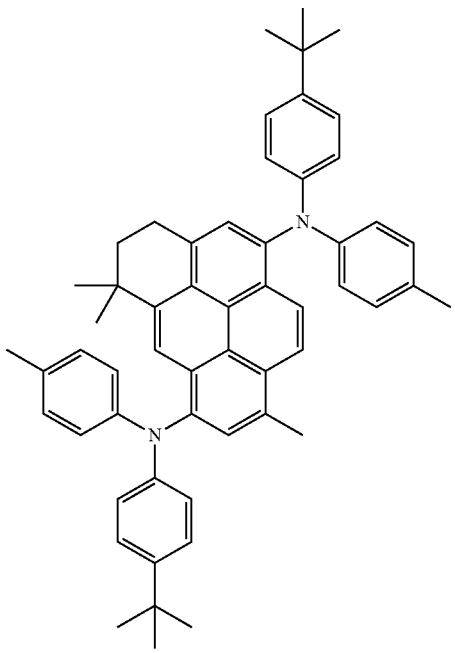

35
-continued
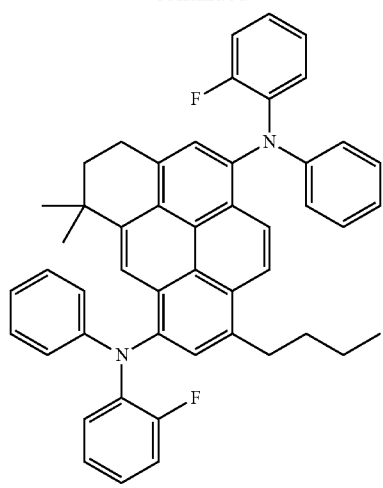
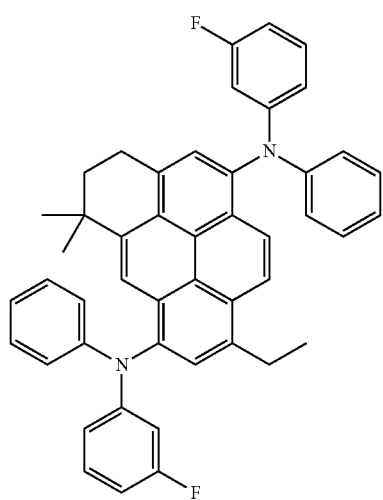
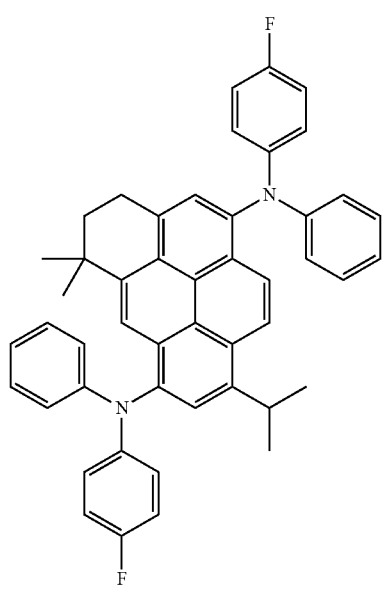
36
-continued
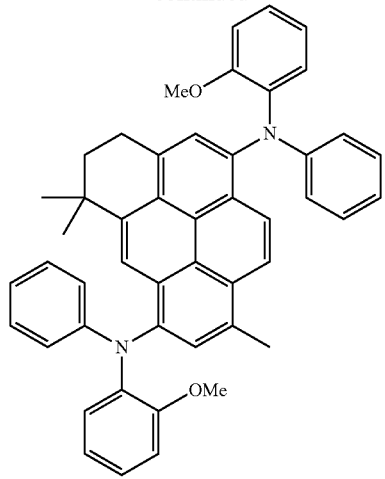
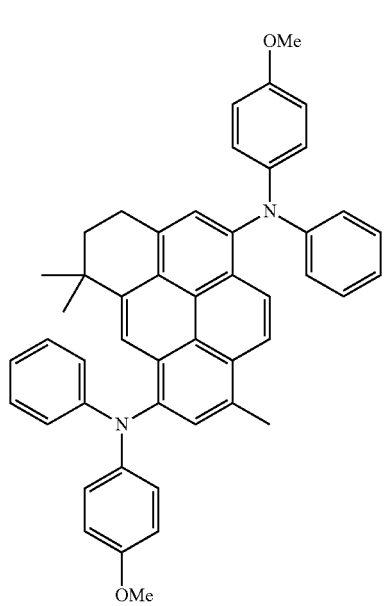
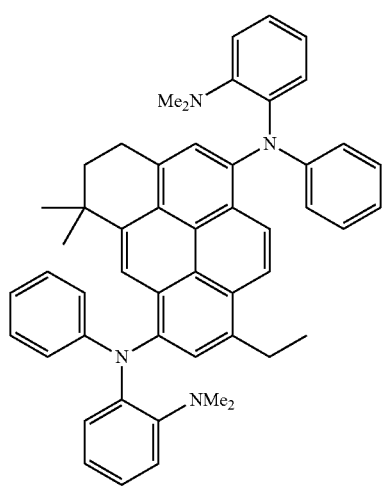

37
-continued
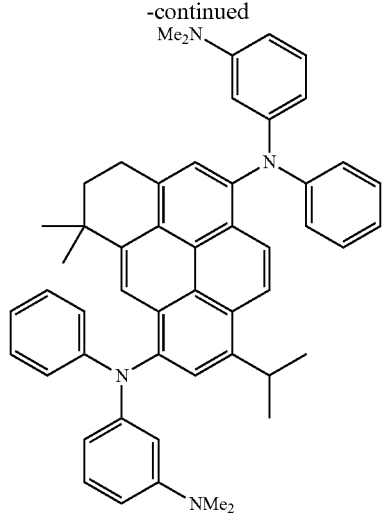
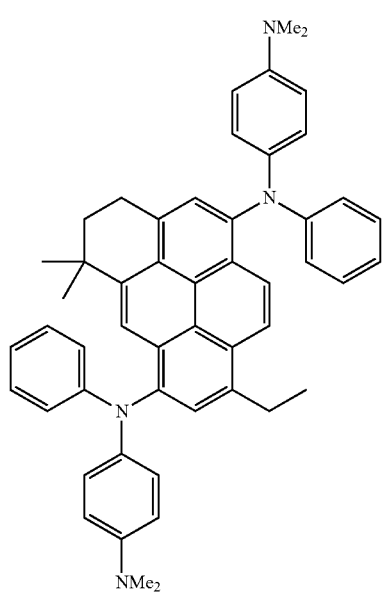
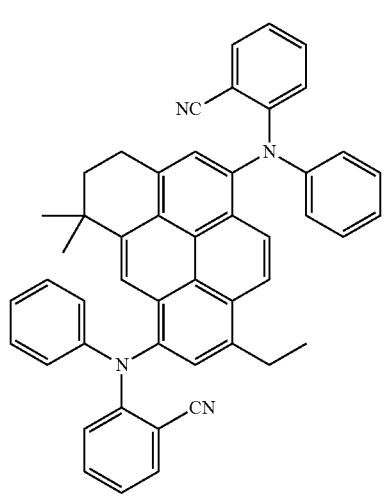
38
-continued
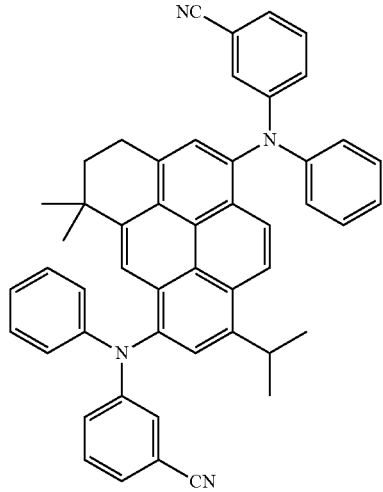
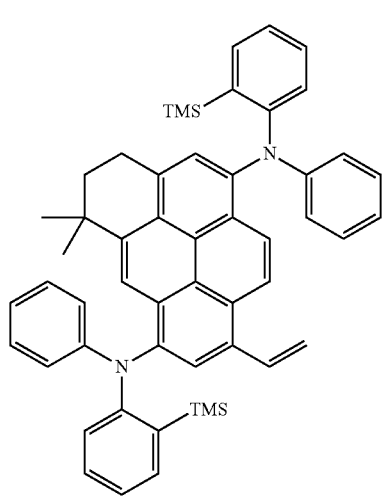
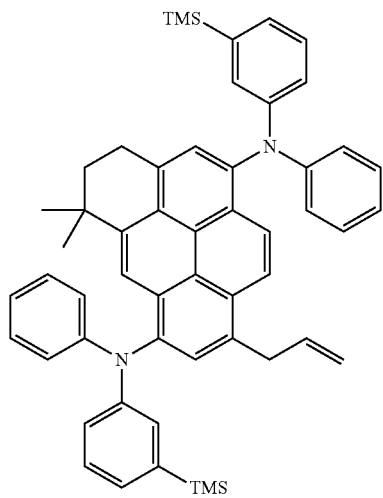

-continued
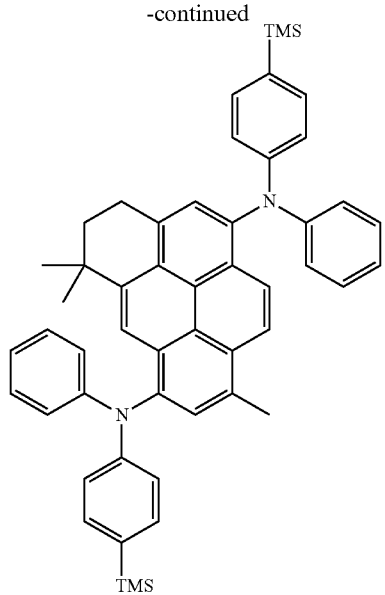
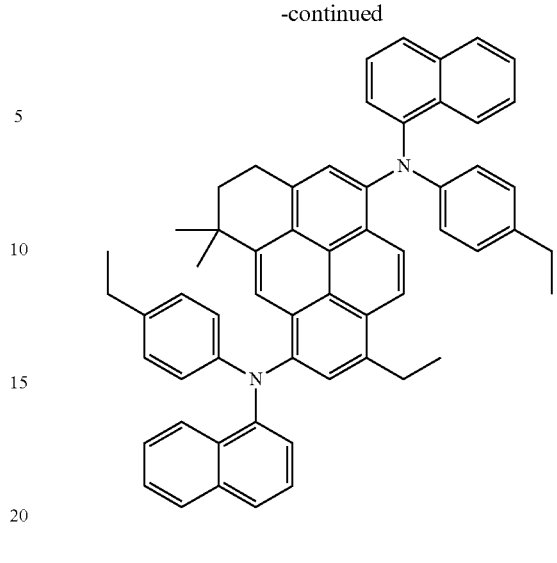
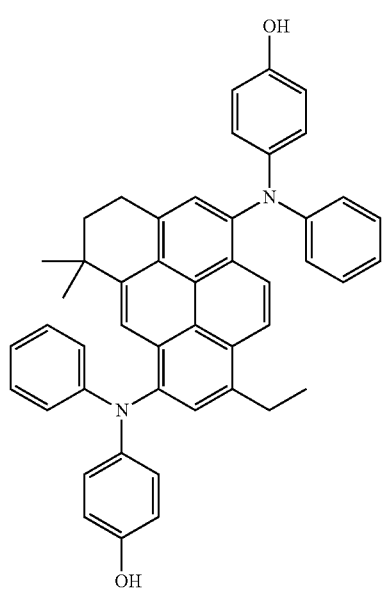
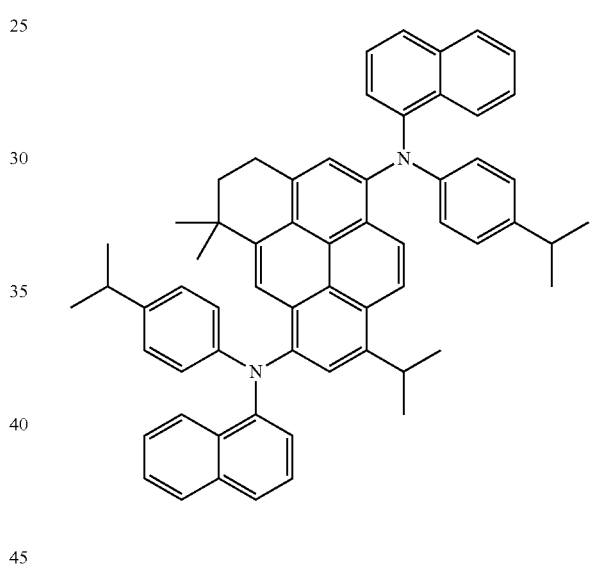
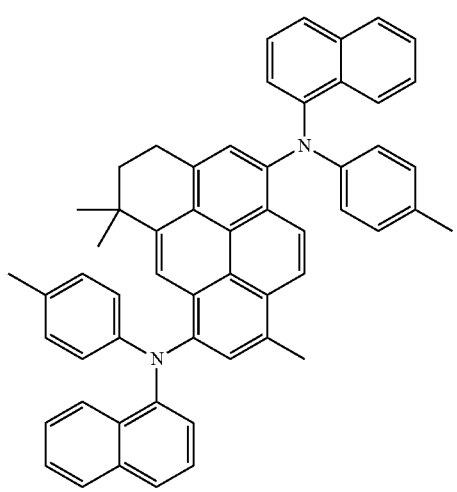
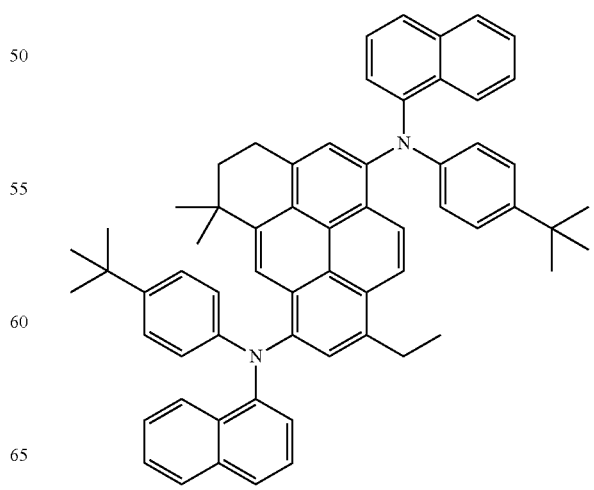

41
-continued
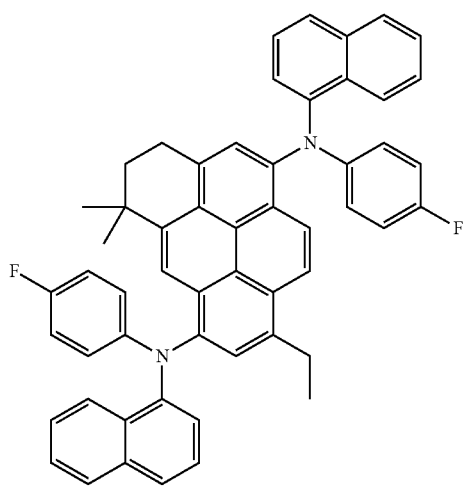
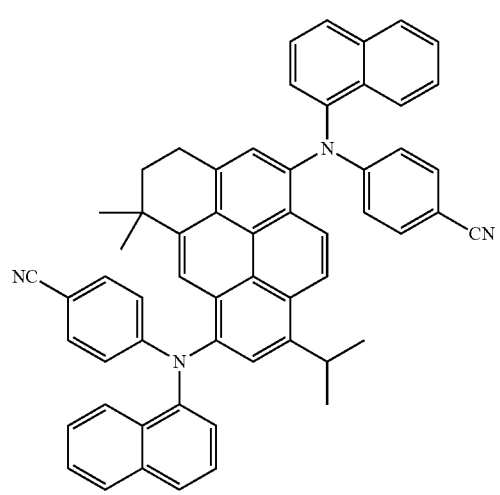
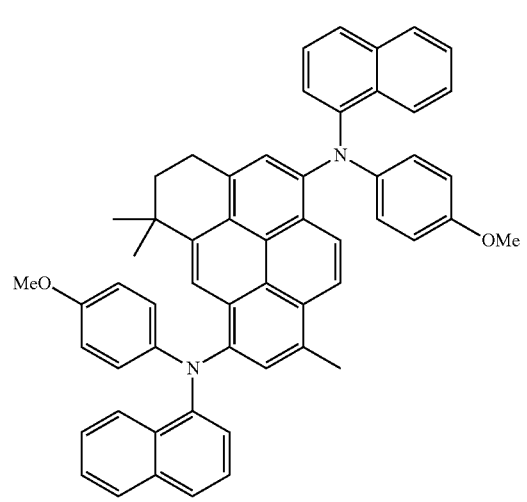
42
-continued
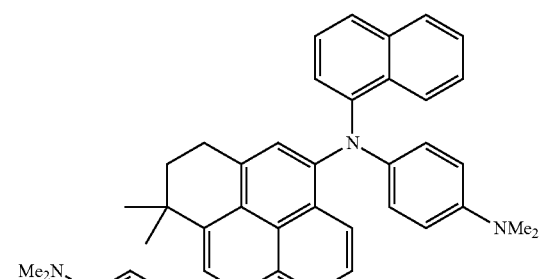
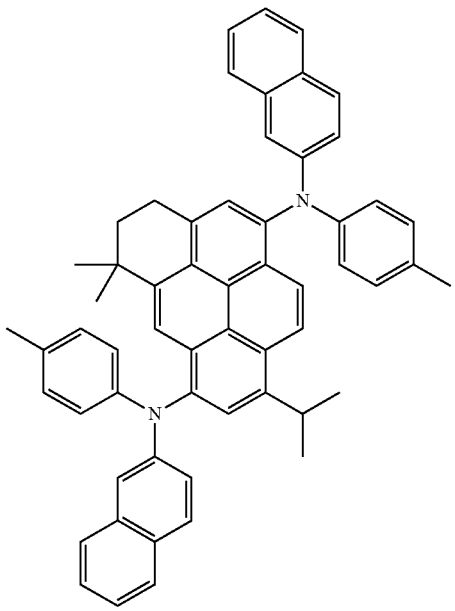
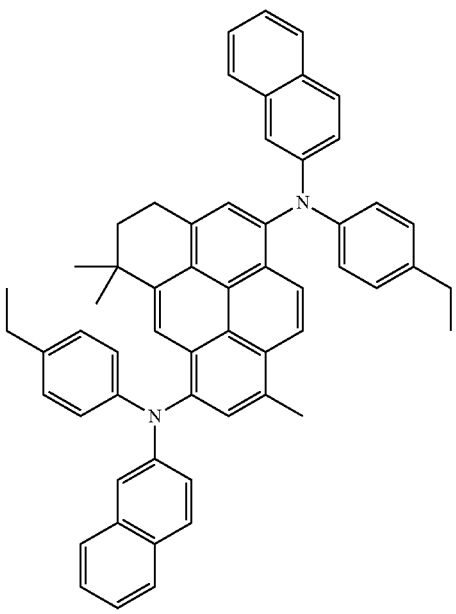

-continued
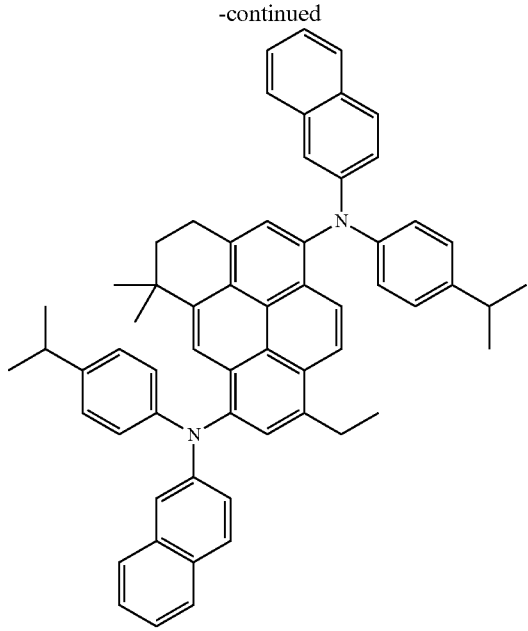
-continued
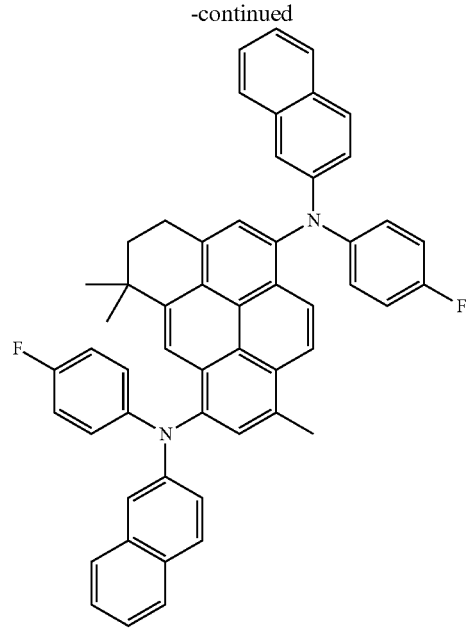
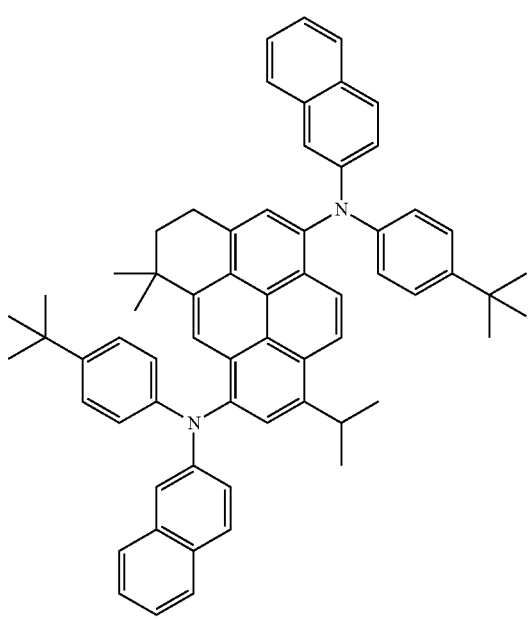
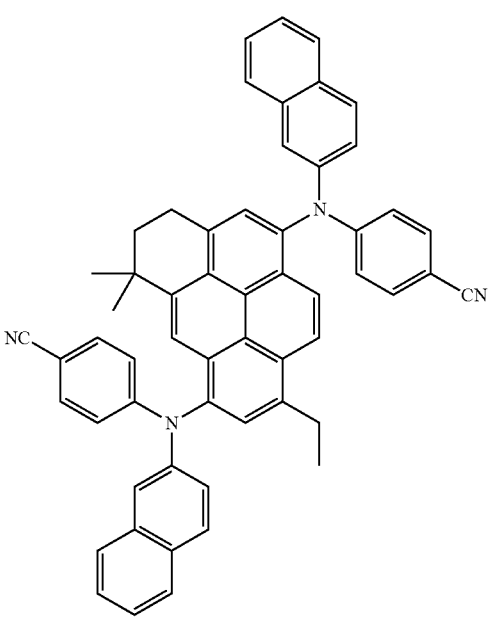

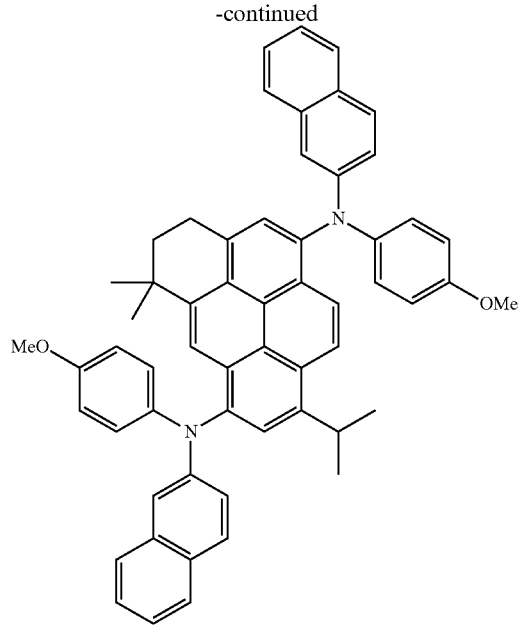
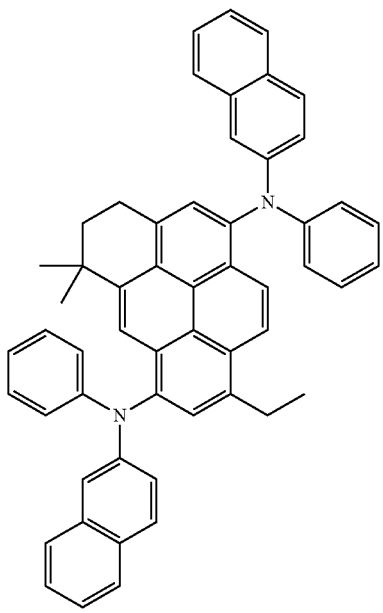
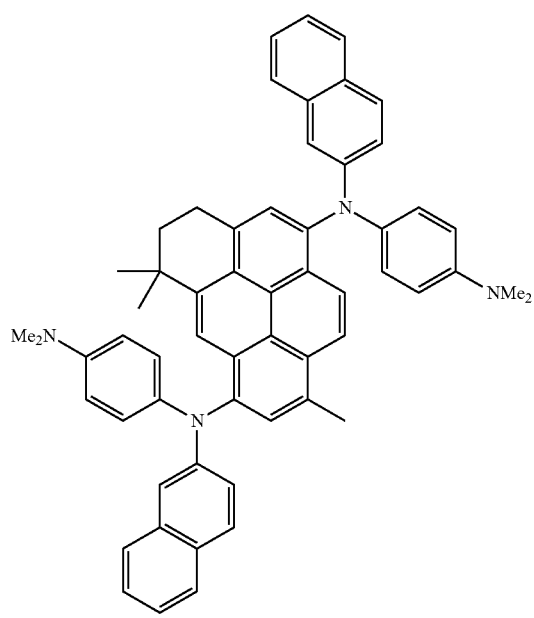

47
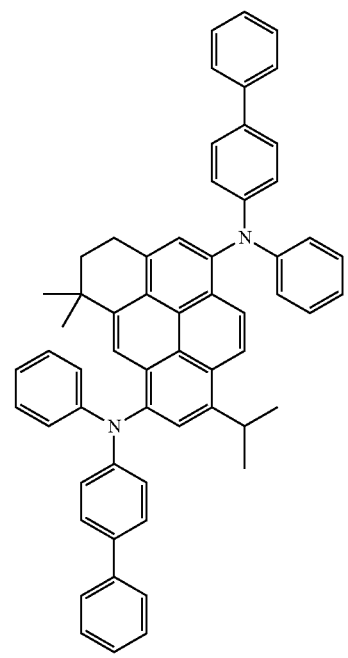
48
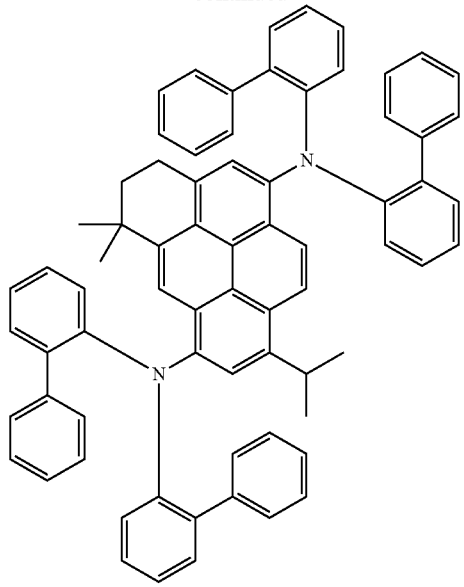 [SMILES: CC(C)c1cc(N(c2ccccc2-c2ccccc2)c2ccccc2-c2ccccc2)c2cc3c4c(cc(N(c5ccccc5-c5ccccc5)c5ccccc5-c5ccccc5)c5ccc1c2c54)CCC3(C)C]
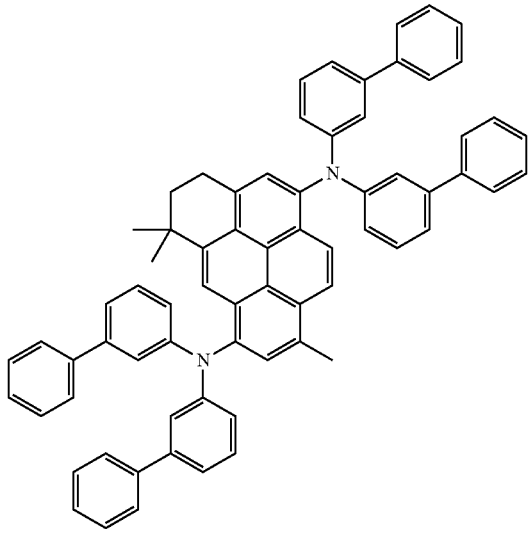
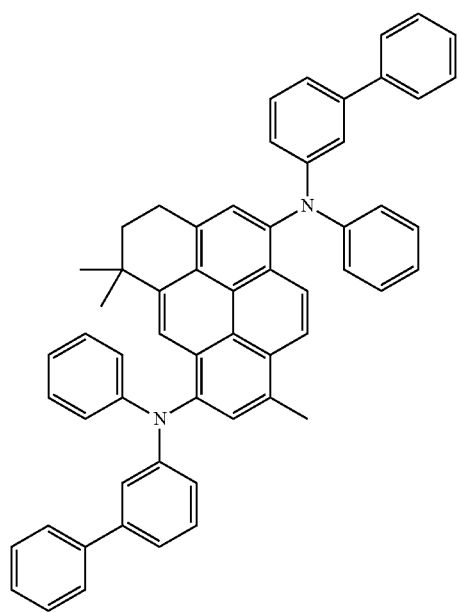
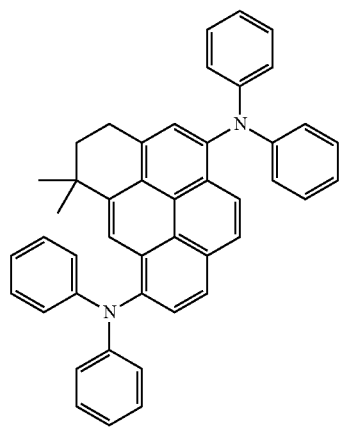

-continued
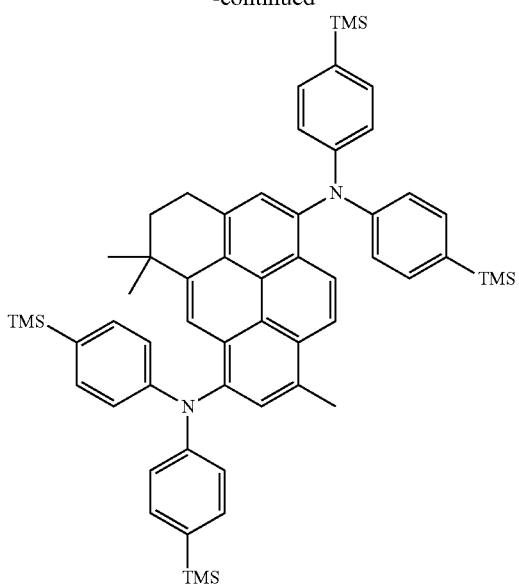
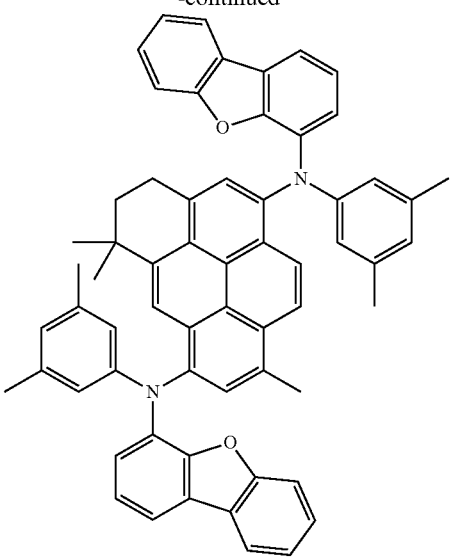
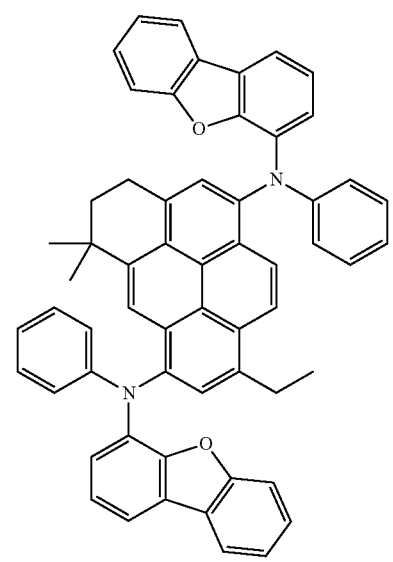
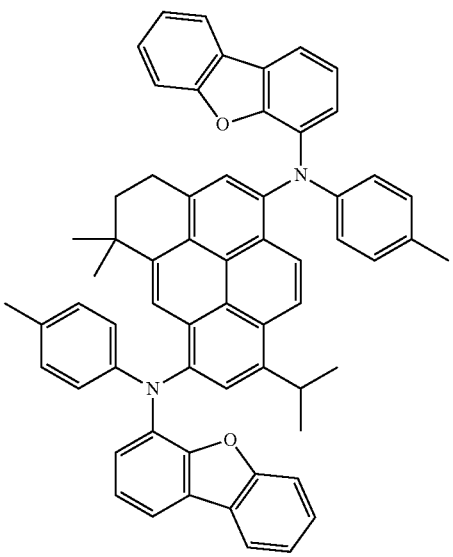
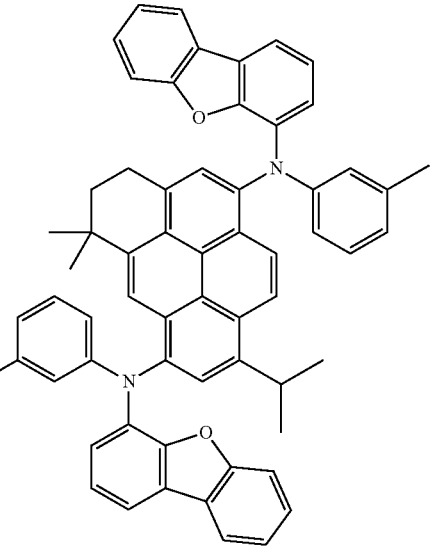
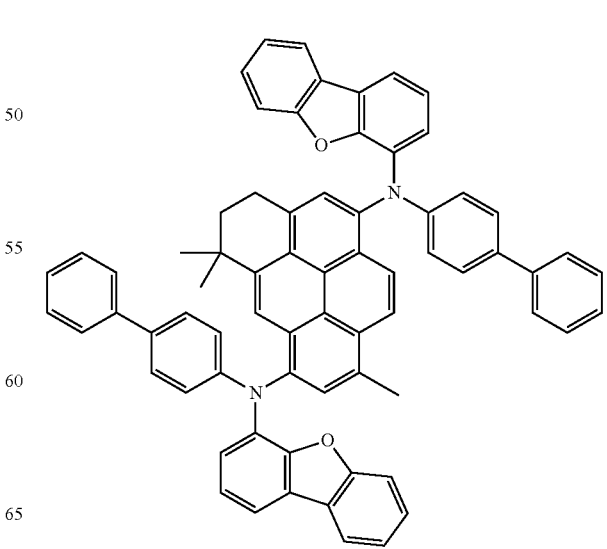

51
-continued
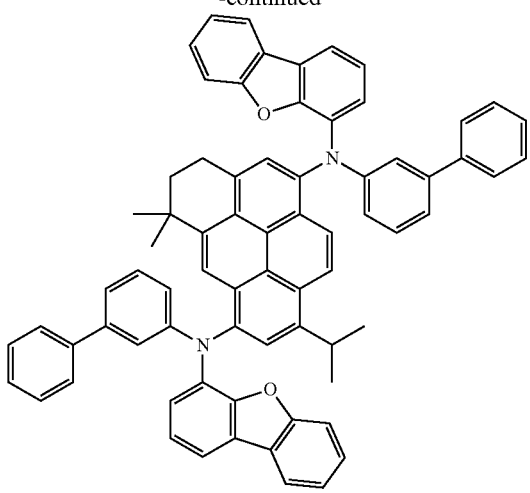
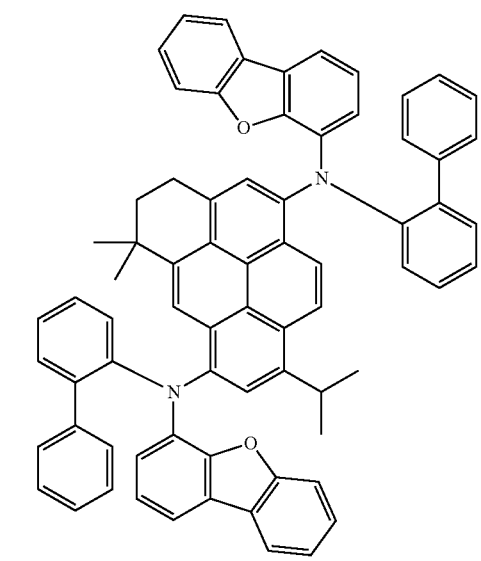
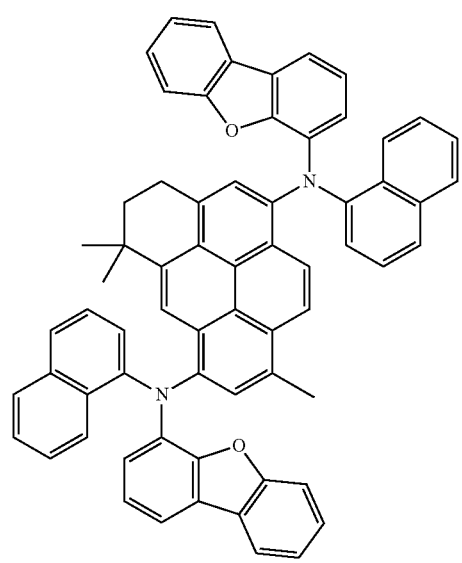
52
-continued
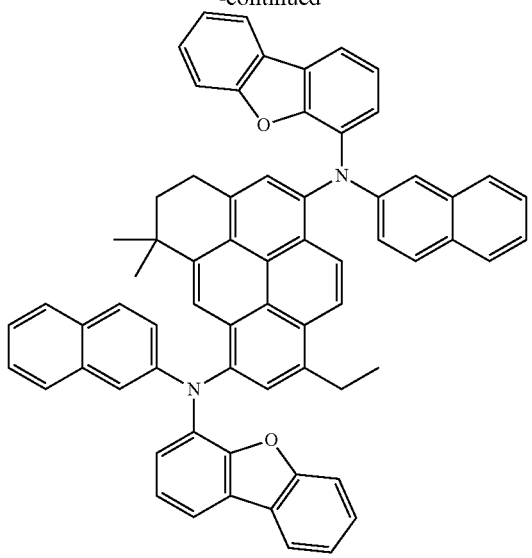
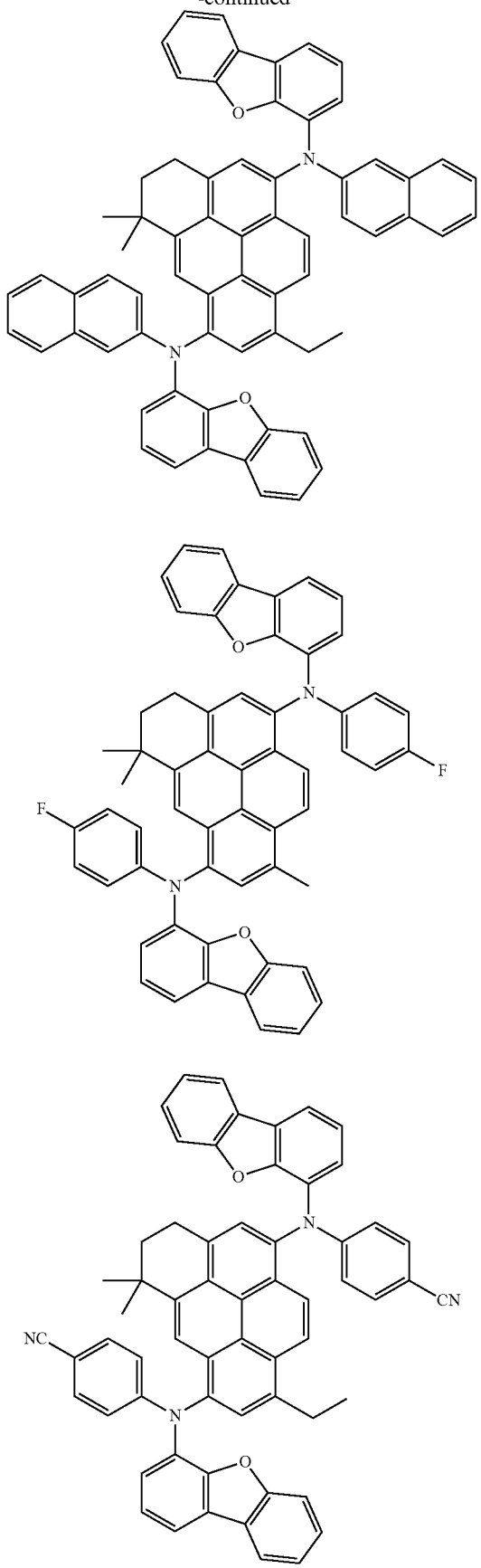

53
-continued

54
-continued

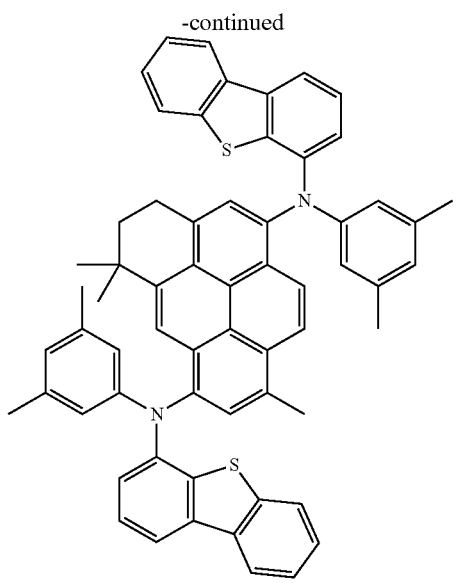
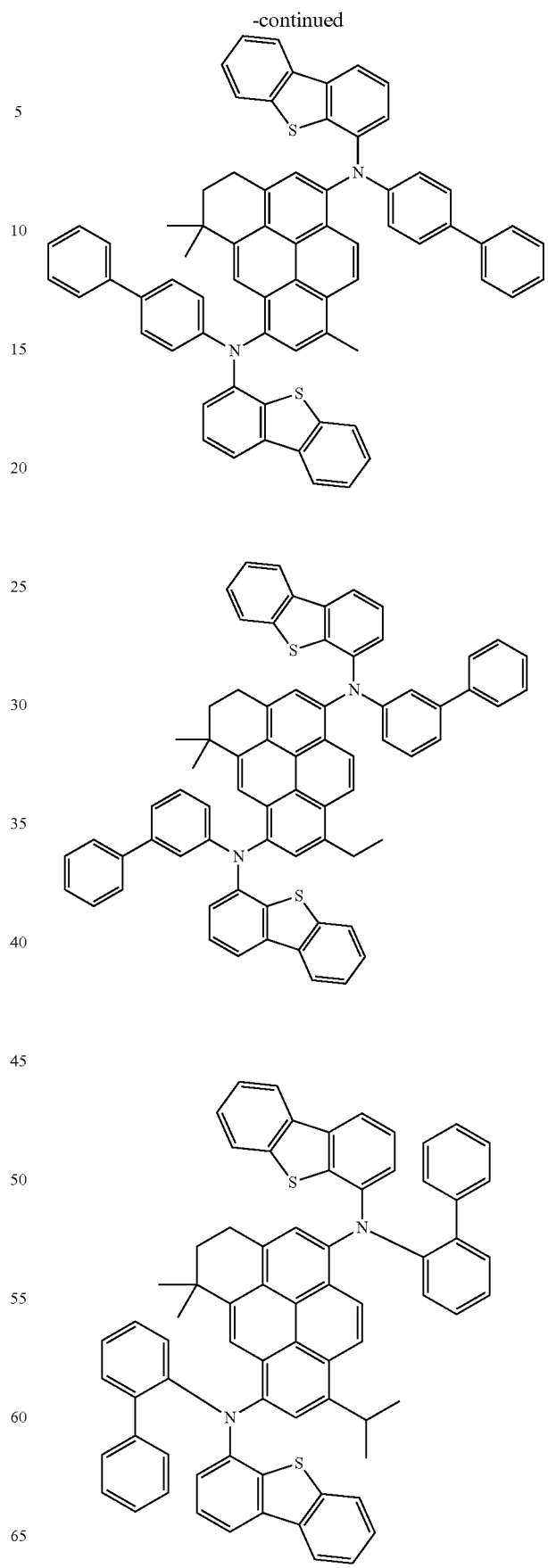

-continued
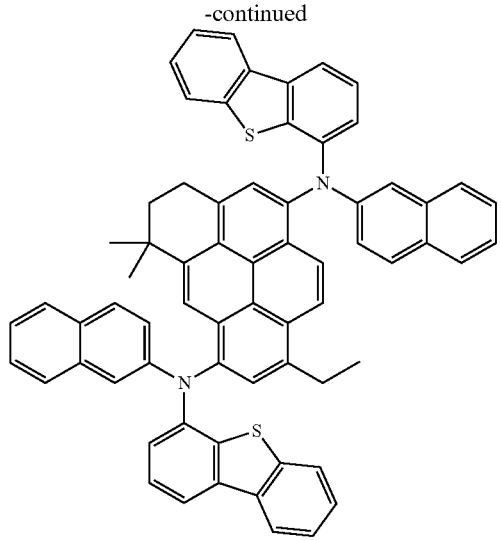
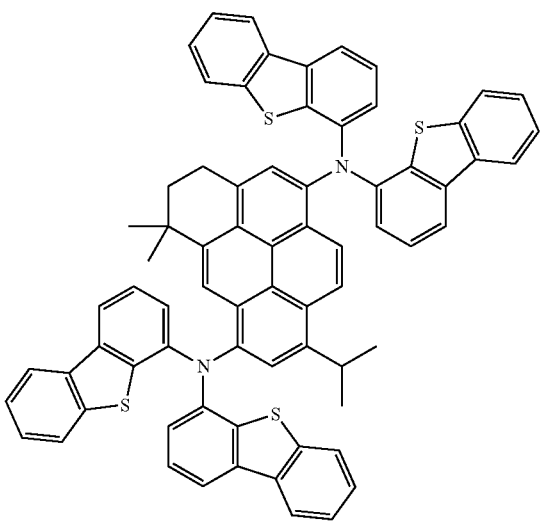
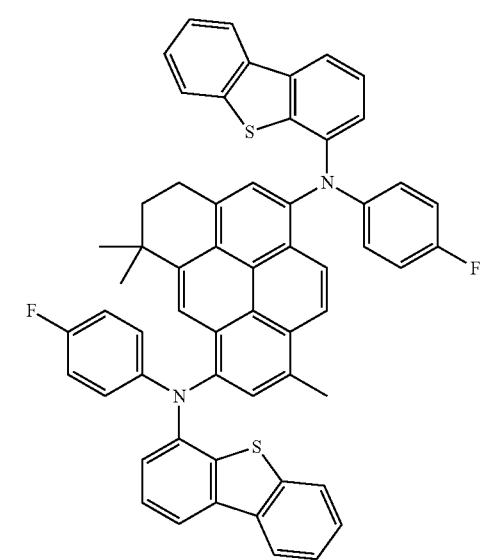
-continued
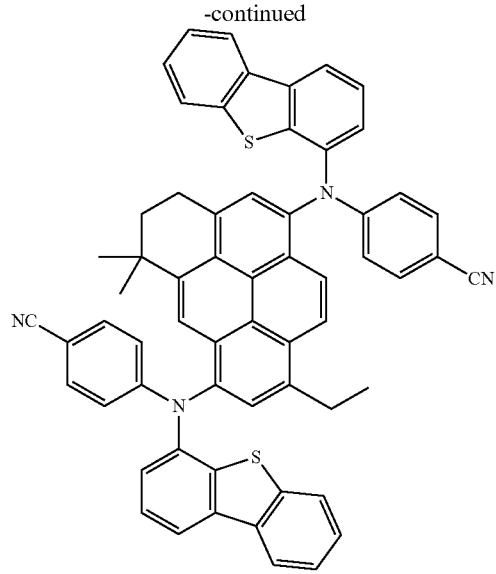
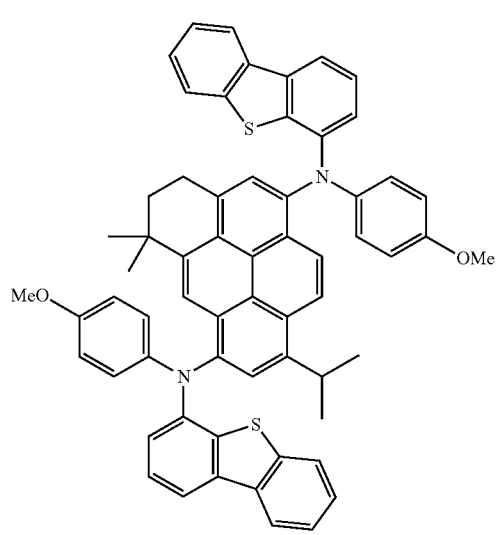
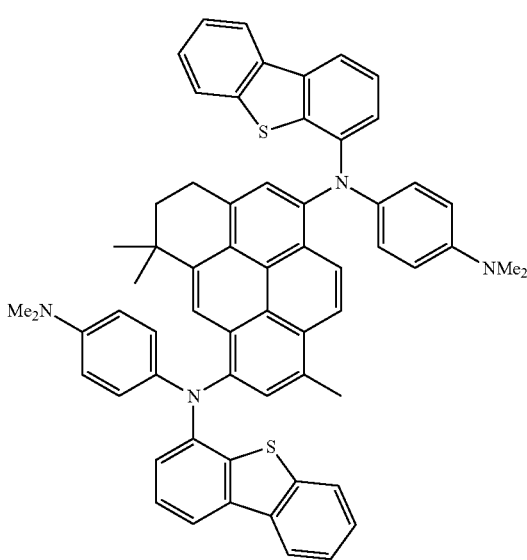

59
-continued
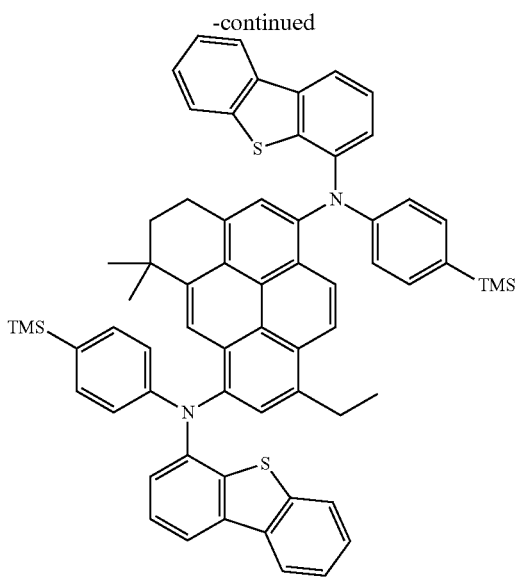
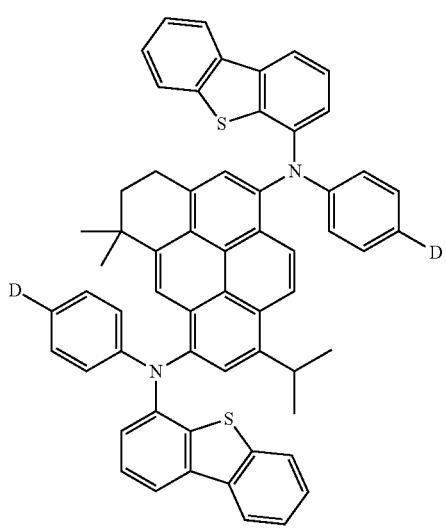
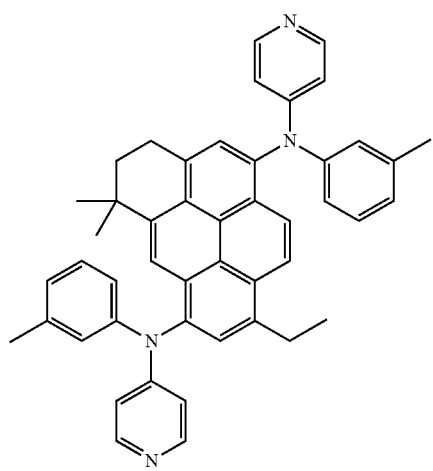
60
-continued
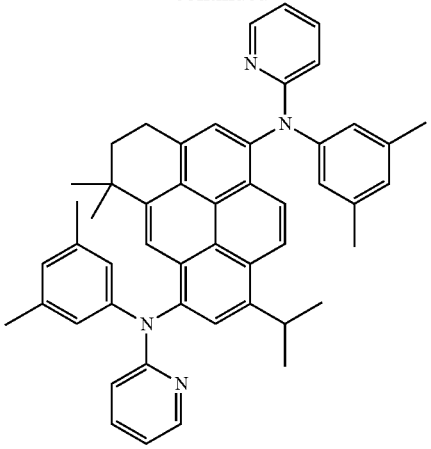
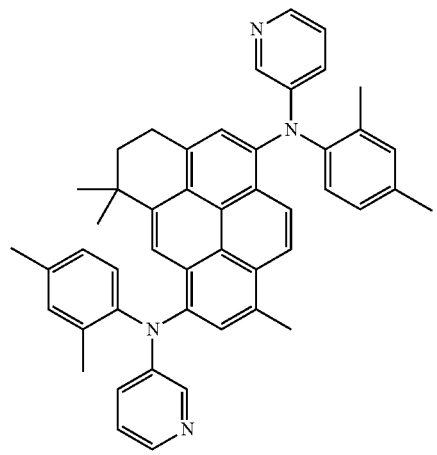
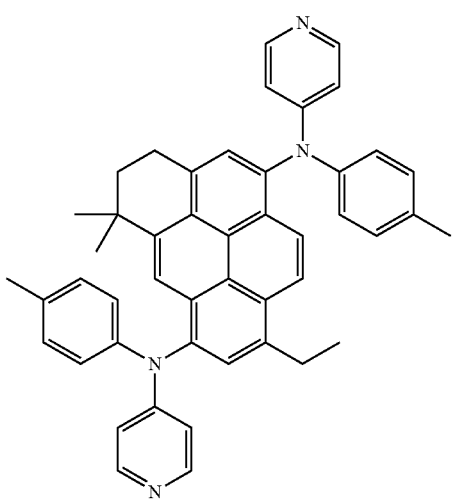

61
-continued
62
-continued
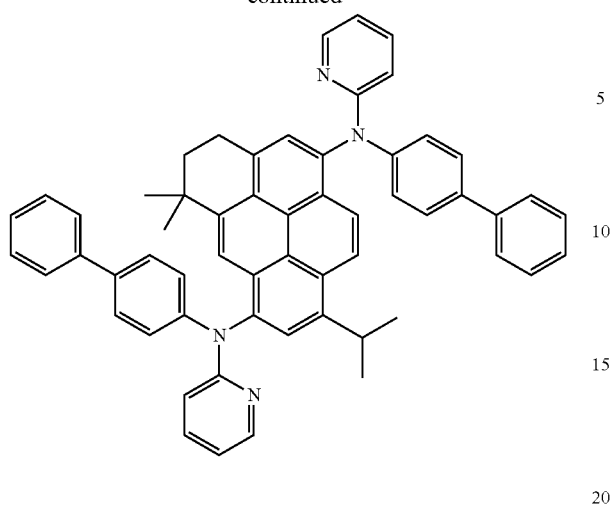
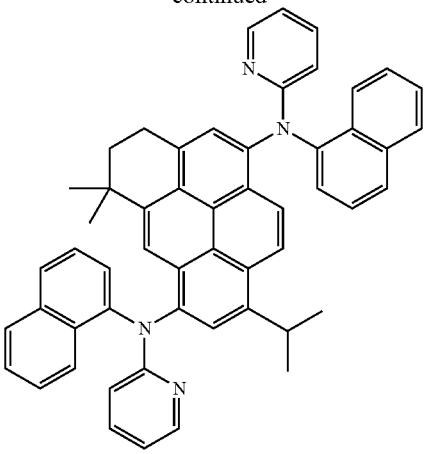
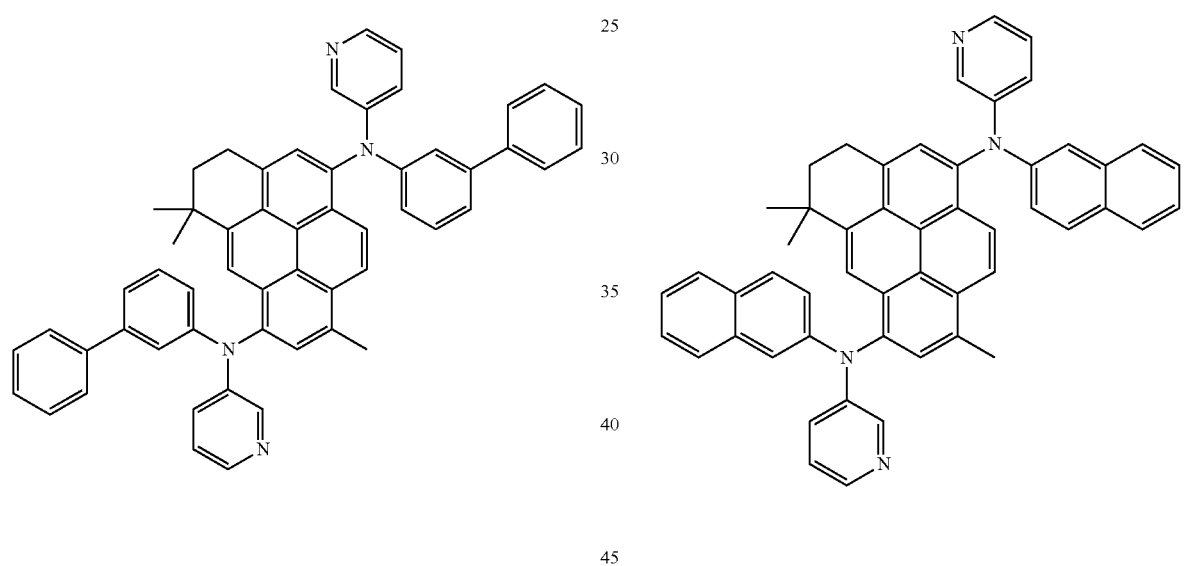
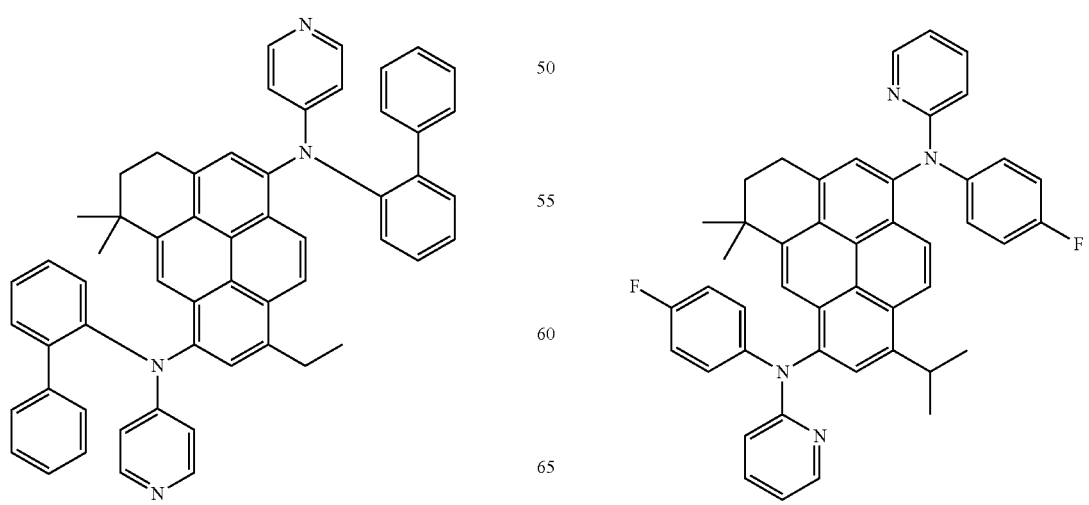

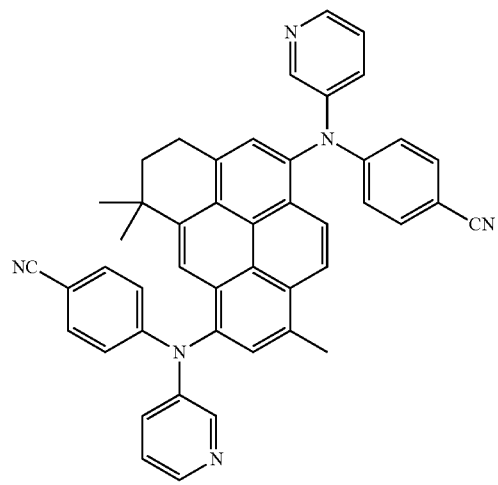
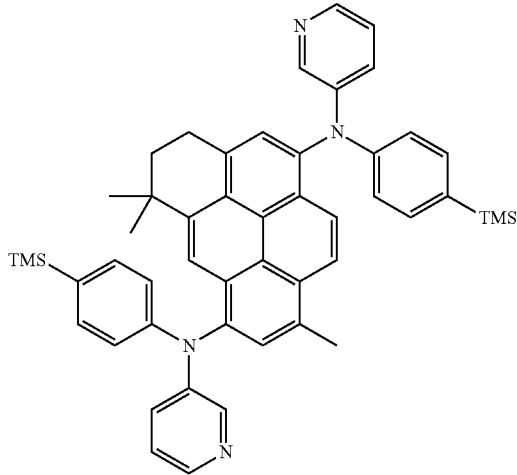
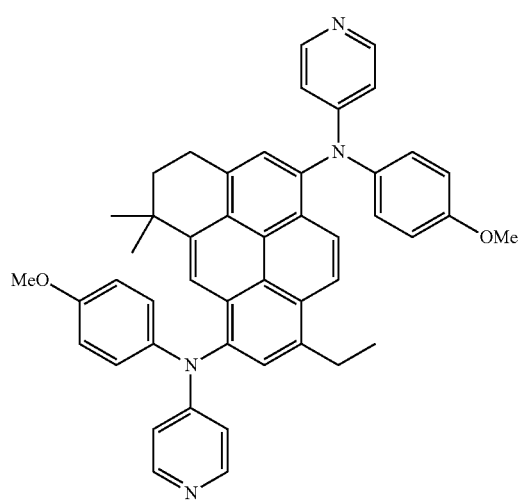
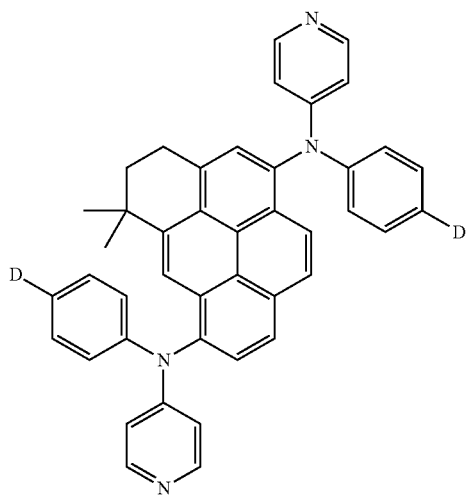
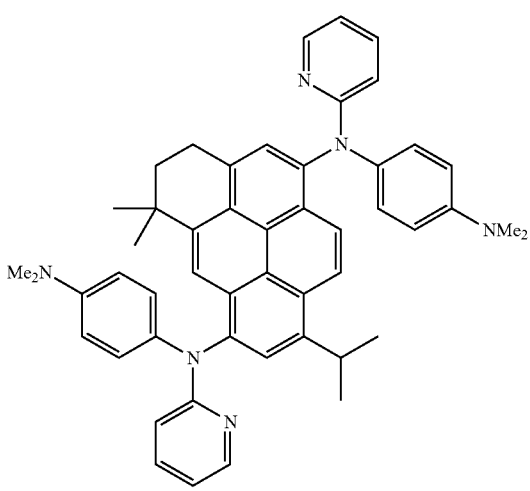
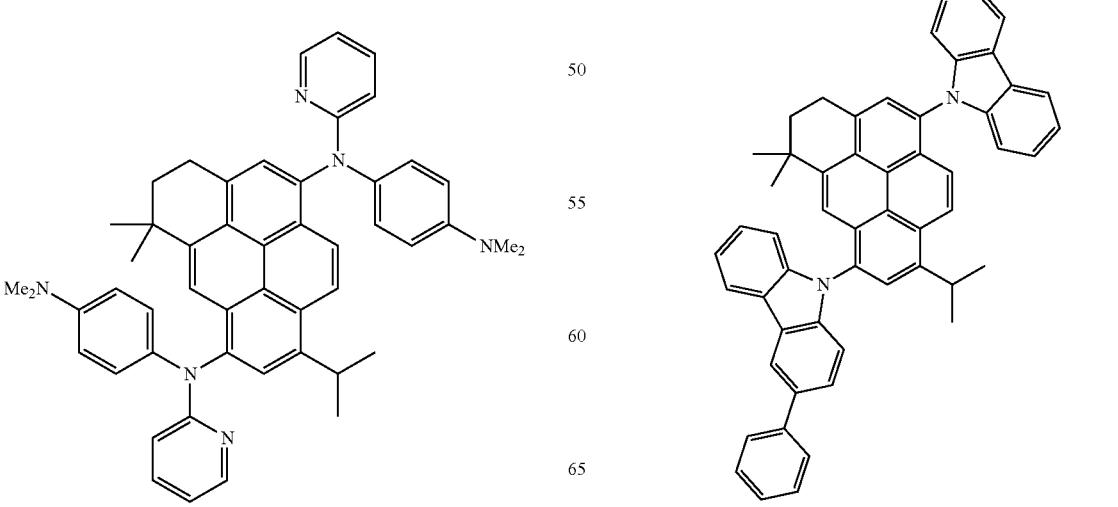

65
-continued
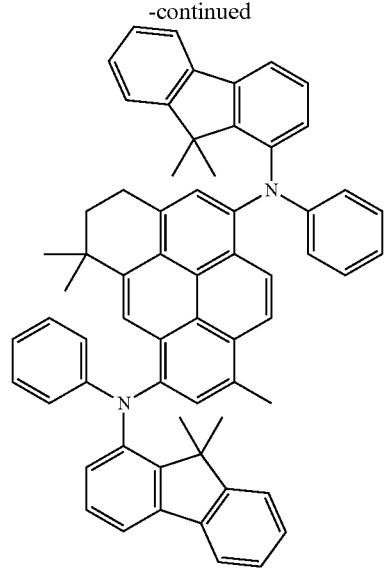
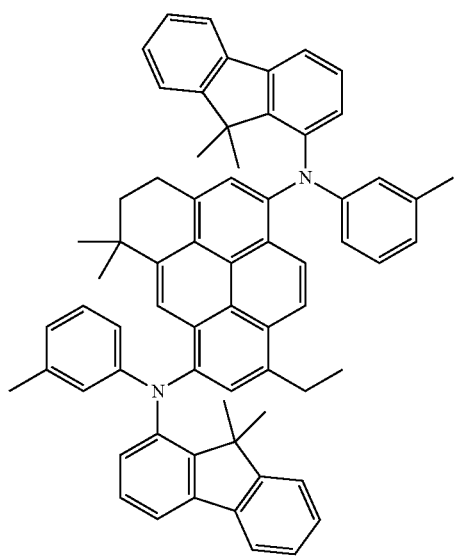
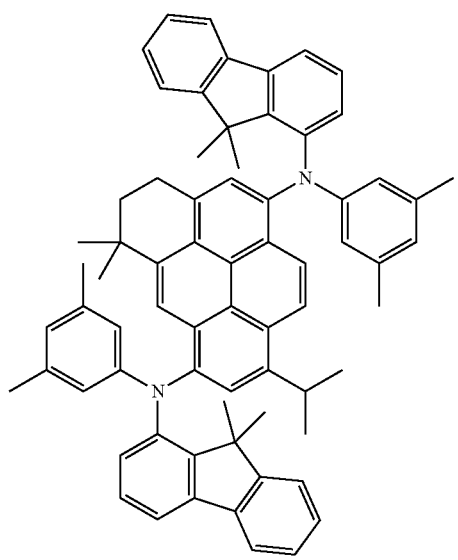
66
-continued
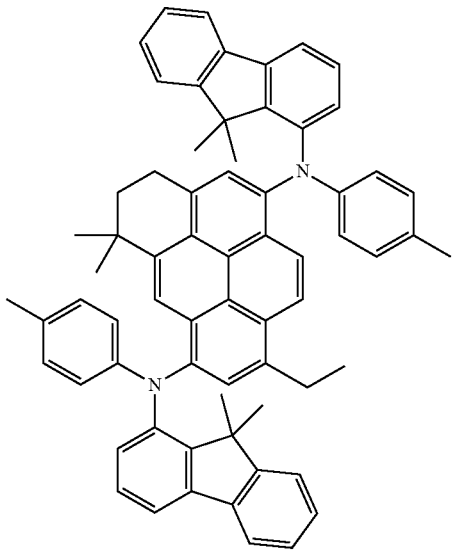
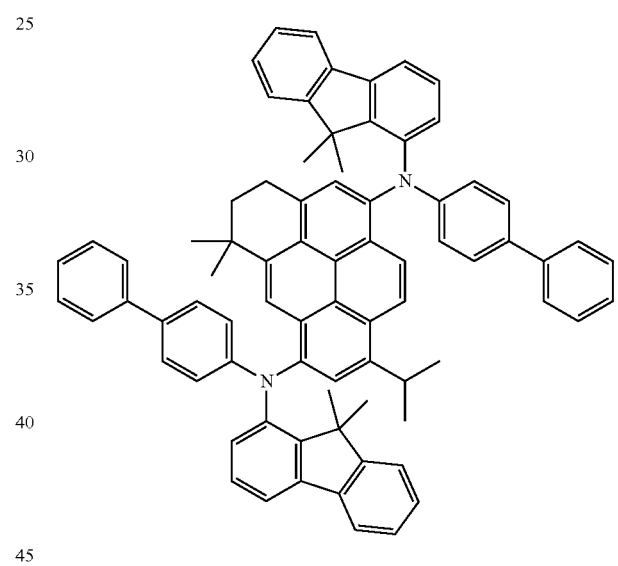
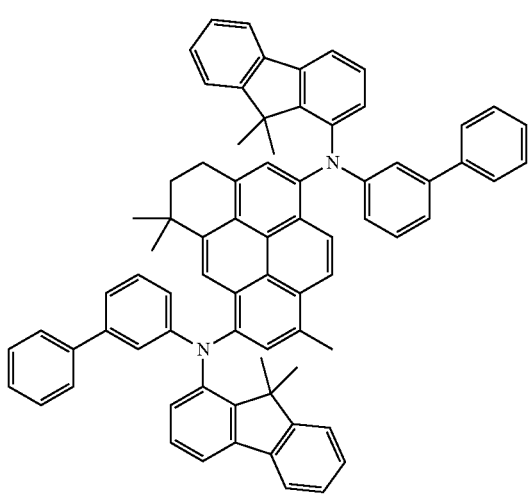

-continued
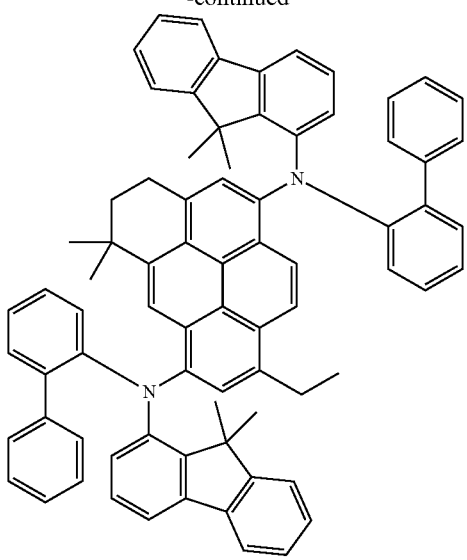
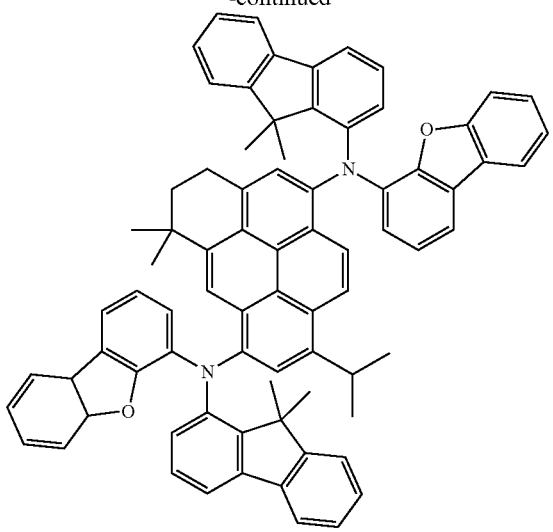
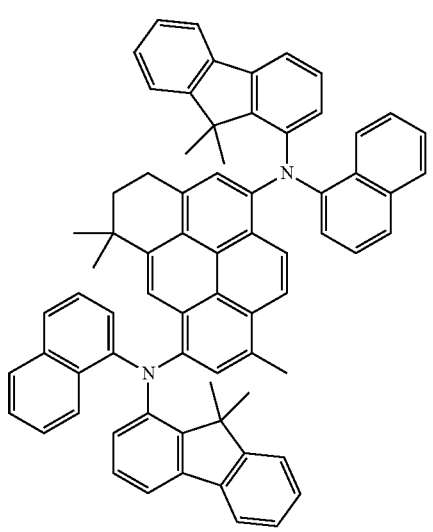
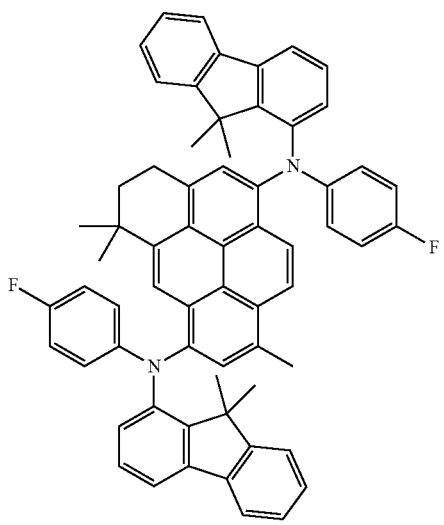
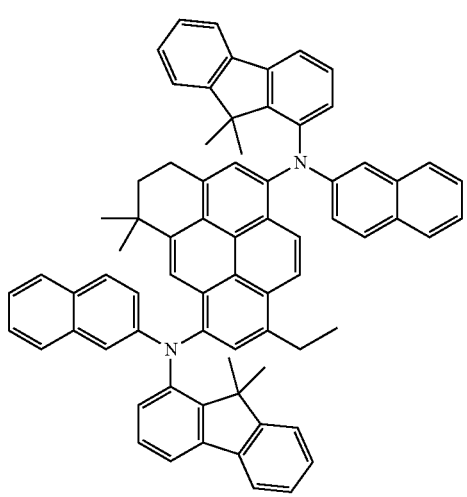
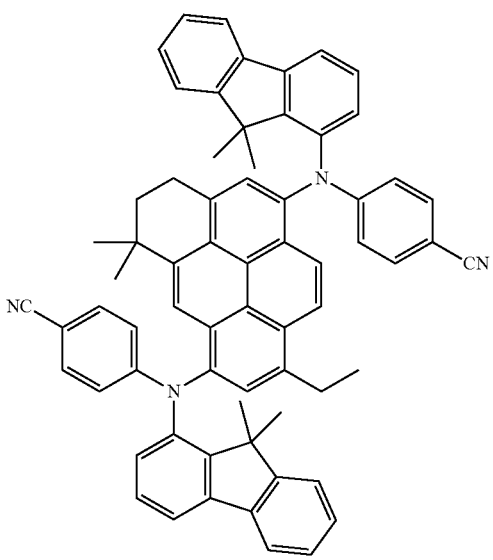

69
-continued
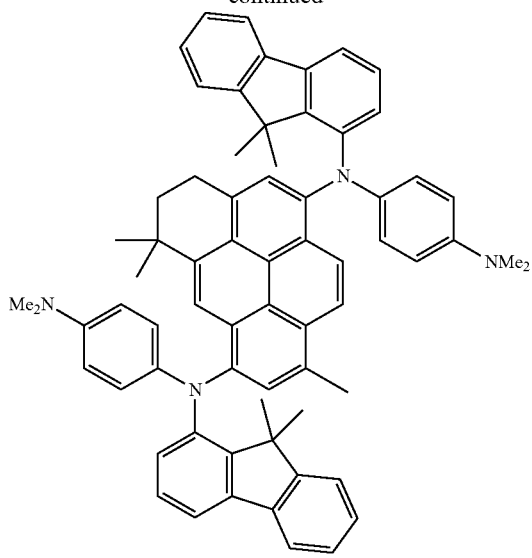
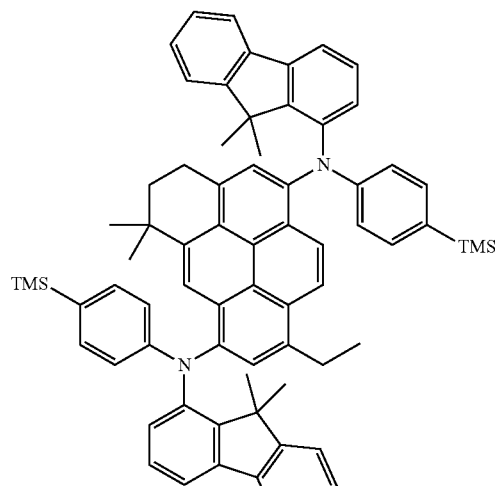
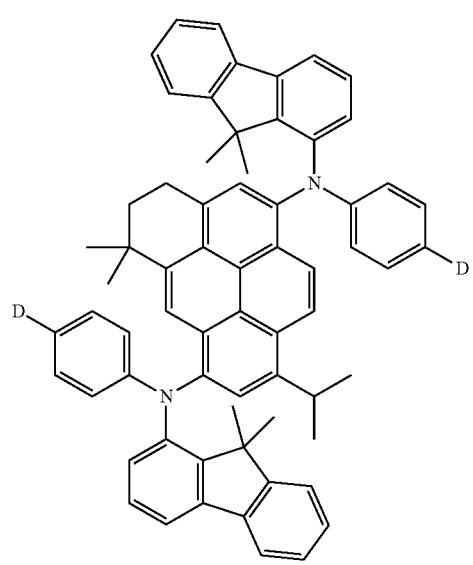
70
-continued
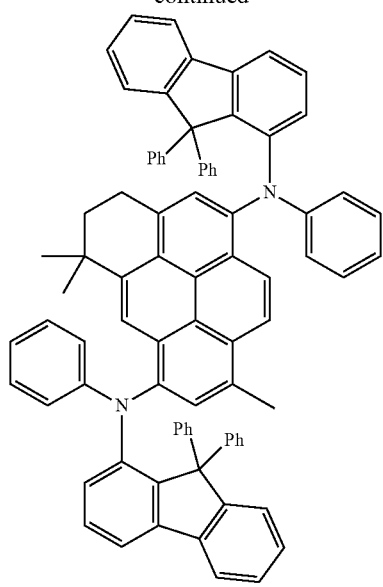
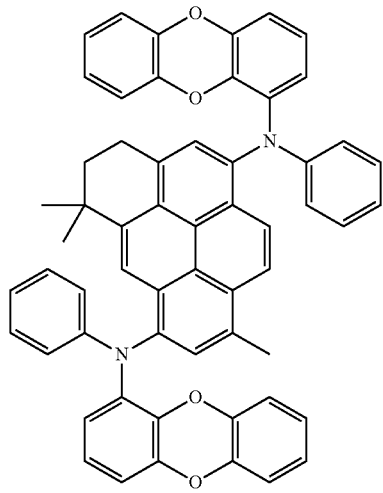
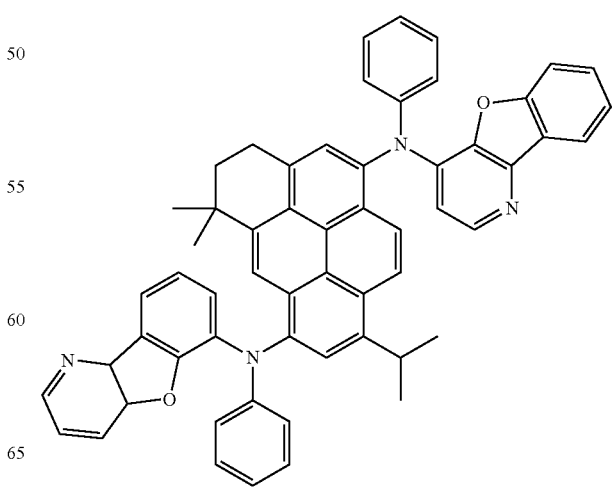

71
-continued
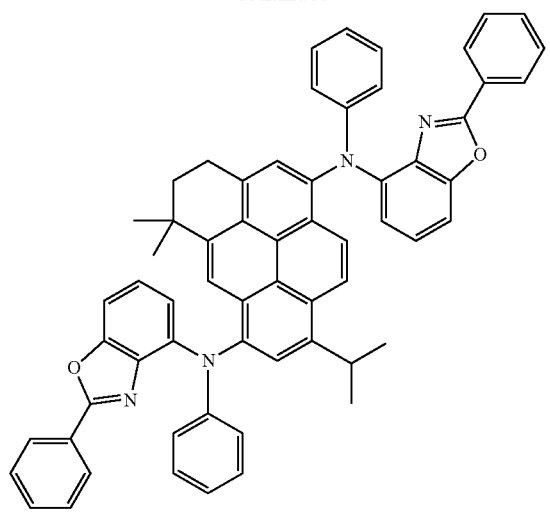
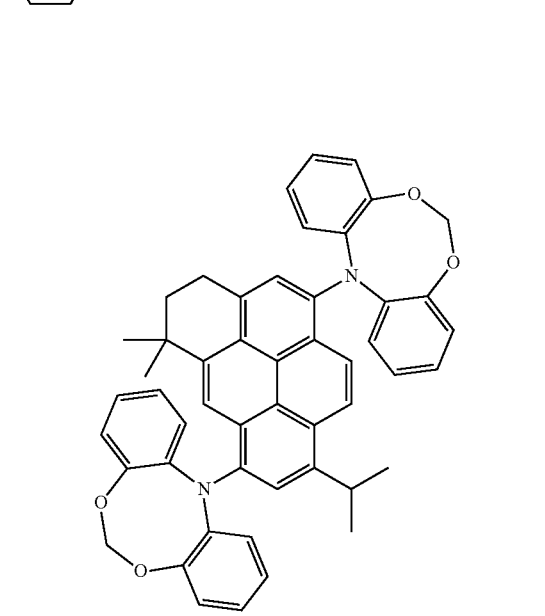
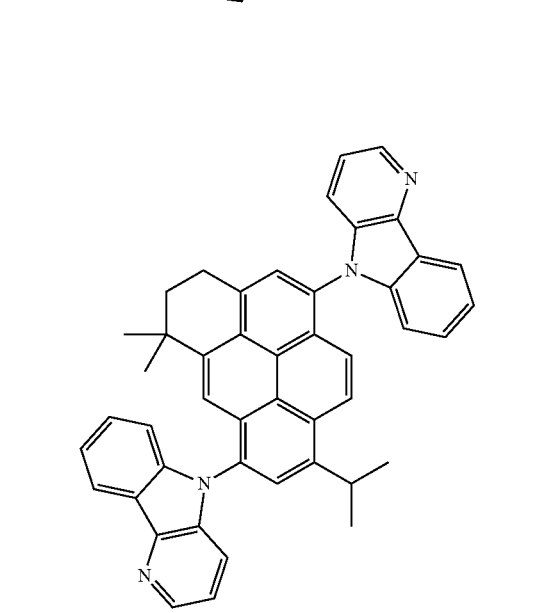
72
-continued
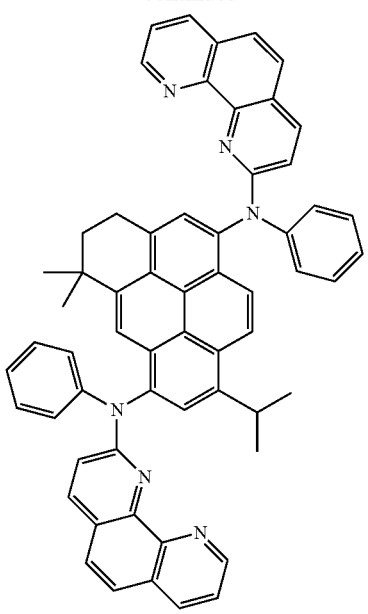
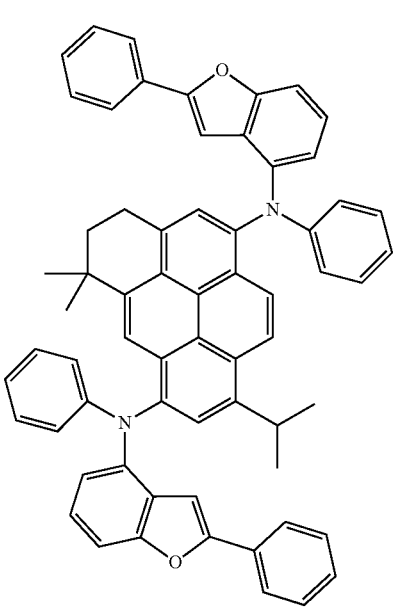 [SMILES: CC(C)c1cc(N(c2ccccc2)c2cccc3oc(-c4ccccc4)cc23)c2cc3c4c(cc(N(c5ccccc5)c5cccc6oc(-c7ccccc7)cc56)c5ccc1c2c54)CCC3(C)C]

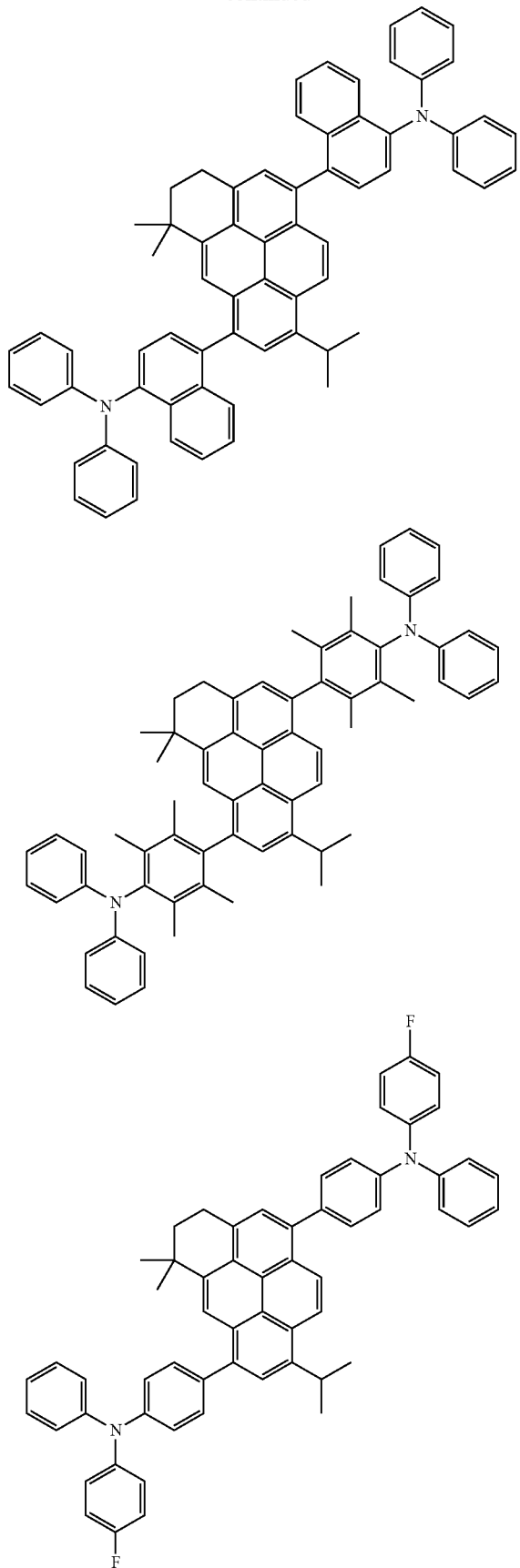

The organic compound according to Formula 1 of the present invention may be used as a blue dopant material. Specifically, the organic compound as a blue dopant material allows the shift of an emission wavelength toward a 7-nm or more shorter wavelength than a conventional blue dopant, and therefore a deep blue host/dopant system suitable for an AM-OLED is provided.

The organic compound according to Formula 1 of the present invention interrupts the formation of an excimer of the dopant by introducing an alkyl group of the ring compound in a pyrene molecular core, and increases the efficiency and lifespan of the diode by increasing the electron density of the core and the stability of the dopant.

The organic compound according to Formula 1 of the present invention facilitates the manufacture of an OLED by a solution process, and reduces production costs due to excellent solubility in a solution.

In an exemplary embodiment of the present invention, a material for forming an EML including the organic compound of Formula 1 is provided. The material for forming the EML may include conventionally added materials, for example, known dopant and host materials.

In an exemplary embodiment of the present invention, the host material may be one or more selected from the group consisting of naphthalene, anthracene, pyrene, phenanthrene, fluoranthene, chrysene, perylene, naphthacene and pentacene.

In an exemplary embodiment of the present invention, the dopant may be a material for a blue dopant.

Another exemplary embodiment of the present invention relates to an OLED in which an organic thin film layer formed of one layer or a plurality of layers and including at least an EML is stacked between a cathode and an anode, and particularly, to an OLED in which the EML contains the organic compound represented by Formula 1 alone or in combination of two or more thereof.

The OLED of the present invention may have a structure in which an anode (hole injection electrode), a HIL, a HTL, an EML and a cathode (electron injection electrode) are sequentially stacked, and preferably, further includes an EBL between the anode and the EML, and an ETL and an EIL between the cathode and the EML. In addition, the OLED may further include a HBL between the cathode and the EML. Hereinafter, the OLED of the present invention will be exemplified. However, the following details do not limit the OLED of the present invention.

According to a method for manufacturing an OLED according to the present invention, first, an anode is formed by coating a substrate surface with a material for an anode by a conventional method. Here, the substrate used herein is preferably a glass substrate or transparent plastic substrate with excellent transparency, surface smoothness, handleability and water repellency. In addition, as a material for an anode, indium tin oxide (ITO), indium zinc oxide (IZO), tin oxide ($SnO_2$), or zinc oxide (ZnO), which is transparent and has excellent conductivity, may be used.

Afterward, a HIL is formed by coating the anode surface with a HIL material by a conventional method, for example, vacuum thermal deposition or spin coating. As such a HIL material, copper phthalocyanine (CuPc), 4,4',4"-tris(3-methylphenylamino)triphenylamine (m-MTDATA), 4,4',4"-tris(3-methylphenylamino)phenoxybenzene (m-MTDAPB), a starburst-type amine such as 4,4',4"-tri(N-carbazolyl)triphenylamine (TCTA) or 4,4',4"-tris(N-(2-naphthyl)-N-phenylamino)-triphenylamine (2-TNATA) or IDE406 commercially available from Idemitsu may be used.

A HTL is formed by coating the HIL surface with a HTL material by a conventional method such as vacuum thermal deposition or spin coating. Here, as a HTL material, bis(N-(1-naphthyl-n-phenyl))benzidine (α-NPD), N,N'-di(naphthalene-1-yl)-N,N'-biphenyl-benzidine (NPB) or N,N'-biphenyl-N,N'-bis(3-methylphenyl)-1,1'-biphenyl-4,4'-diamine (TPD) may be used.

An EML is formed by coating the HTL surface with an EML material by a conventional method such as vacuum thermal deposition or spin coating. Here, when a single light emitting material or light emitting host material of the EML materials used herein is green, tris(8-hydroxyquinolinolato)aluminum ($Alq_3$) may be used, and when blue, 8-hydroxyquinoline beryllium salt (Balq), a 4,4'-bis(2,2-biphenylethenyl)-1,1'-biphenyl (DPVBi) material, a spiro material, a spiro-4,4'-bis(2,2-biphenylethenyl)-1,1'-biphenyl (spiro-DPVBi) material, a 2-(2-benzoxazolyl)-phenol lithium salt (LiPBO), bis(biphenylvinyl)benzene, an aluminum-quinoline metal complex, or a metal complex of imidazole, thiazole or oxazole may be used.

Among the EML materials, a dopant that can be used with a light emitting host is a blue fluorescent dopant, and as the blue fluorescent dopant, the compound of the present invention is preferably used. A different fluorescent dopant may be IDE102 or IDE105, which is commercially available from Idemitsu, and a phosphorescent dopant may be tris(2-phenylpyridine)iridium(III) (Ir(ppy)3), iridium(III) bis[(4,6-difluorophenyl)pyridinato-N,C-2']picolinate (FIrpic) (Reference: [Chihaya Adachi et al., Appl. Phys. Lett., 2001, 79, 3082-3084]), platinum(II) octaethylporphyrin (PtOEP), or TBE002 (Corbion).

Optionally, an EBL may be further formed between the HTL and the EML.

An ETL is formed by coating the EML surface with an ETL material by a conventional method such as vacuum thermal deposition or spin coating. Here, the ETL material used herein may be, but is not particularly limited to, tris(8-hydroxyquinolinolato)aluminum (Alq3).

Optionally, a HBL may be further formed between the EML and the ETL, and a phosphorescent dopant is also used in the EML. Therefore, the diffusion of triplet excitons or holes into the ETL may be prevented.

The phosphorescent dopant may be an organic compound represented by Formula 1 or 2.

The HBL may be formed through vacuum thermal deposition and spin coating of a HBL material according to a conventional method, and a HBL material may be, but is not particularly limited to, (8-hydroxyquinolinolato)lithium (Liq), bis(8-hydroxy-2-methyl quinolinolato)-aluminum biphenoxide (BAlq), bathocuproine (BCP), or LiF.

An EIL is formed by coating the ETL surface with an EIL material by a conventional method such as vacuum thermal deposition or spin coating. Here, as the EIL material used herein, LiF, Liq, $Li_2O$, BaO, NaCl or CsF may be used.

A cathode is formed by coating the EIL surface with a cathode material by a conventional method such as vacuum thermal deposition.

Here, as the cathode material used herein, lithium (Li), aluminum (Al), aluminum-lithium (Al—Li), calcium (Ca), magnesium (Mg), magnesium-indium (Mg—In), or magnesium-silver (Mg—Ag) may be used. In addition, in the case of a top-emission OLED, a light-permeable transparent cathode may be formed using ITO or IZO.

A capping layer (CPL) may be formed of a composition for forming a capping layer of the present invention on a surface of the cathode.

EXAMPLES

Hereinafter, synthesis methods for the compounds will be described with reference to representative examples. However, the synthesis methods for the compounds of the present invention are not limited to the following methods below, and the compounds of the present invention may be prepared by methods exemplified below and methods known in the art.

Synthesis Examples

Synthesis of Intermediate A

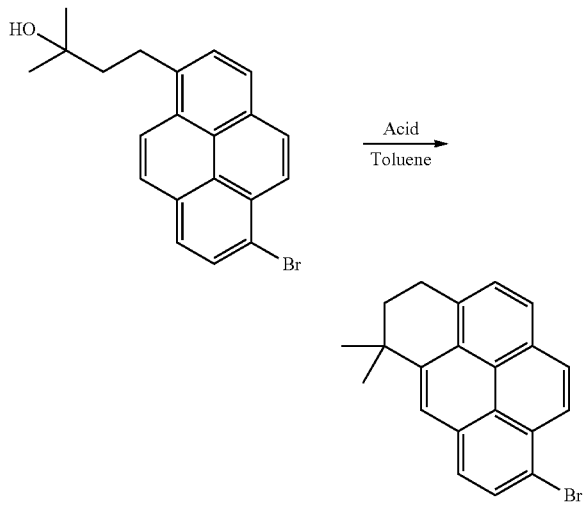

288.4 g (1 mol) of 2-methyl-4-(pyrene-1-yl)butane-2-ol was dissolved in 2.8 L of toluene, and 10 wt % of an acid was added. The mixture was dehydrated using a Dean-Stark apparatus, and stirred for 12 hours while heating/refluxing. After the reaction was completed, 10 L of water was added, and the toluene layer was extracted and extracted again with 1 L of water. The extracted solution was treated with $MgSO_4$ to remove remaining moisture and dried in a vacuum oven. Hereinafter, column purification was performed using n-hexane, thereby obtaining 192.0 g of Compound A with a yield of 71%.

Synthesis Example 1

Synthesis of Compound 1

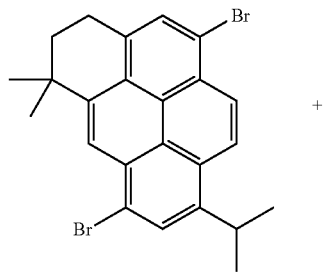

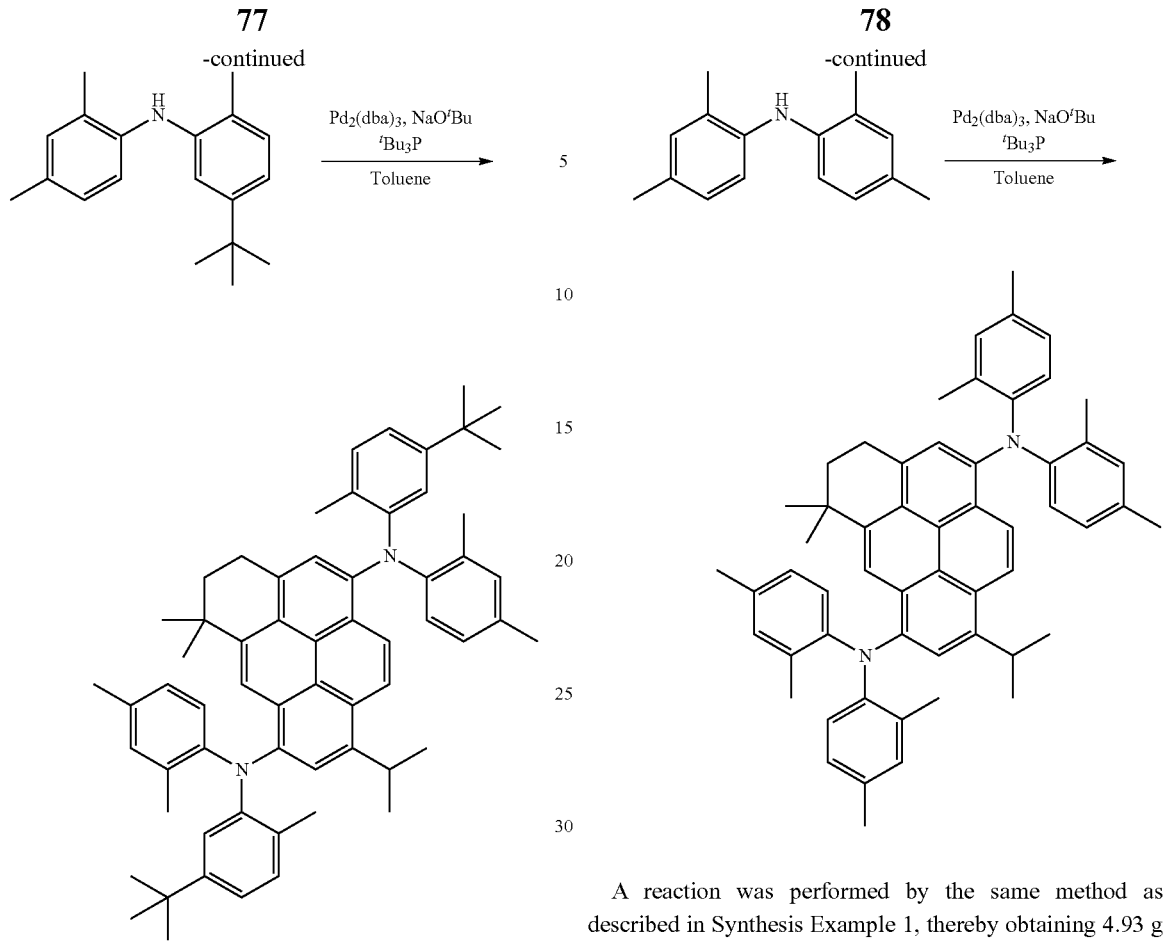

After 4.70 g (10.0 mmol) of 1,7-dibromo-9-isopropyl-5,5-dimethyl-4,5-dihydro-3H-benzo[cd]pyrene and 8.02 g (30 mmol) of N-(5-(tert-butyl)-2-methylphenyl)-2,4-dimethylaniline were dissolved in 100 ml of toluene, 5.76 g (60.0 mmol) of NaOtBu, 0.46 g (0.5 mmol) of Pd$_2$(dba)$_3$, and 0.2 g (1.0 mmol) of tBu$_3$P were added, and the mixture was stirred for 6 hours while heating/refluxing. After the reaction was completed, the toluene layer was extracted by adding 100 ml of water, and then extracted again by adding 50 ml of water. The extracted solution was treated with MgSO$_4$ to remove remaining moisture, and then dried in a vacuum oven. Afterward, column purification was performed using n-hexane/MC, thereby obtaining 5.06 g of Compound 1 with a yield of 60%.

Synthesis Example 2

Synthesis of Compound 2

A reaction was performed by the same method as described in Synthesis Example 1, thereby obtaining 4.93 g of Compound 2 with a yield of 65%, except that 4.70 g (10.0 mmol) of 1,7-dibromo-9-isopropyl-5,5-dimethyl-4,5-dihydro-3H-benzo[cd]pyrene and 6.76 g (30 mmol) of bis(2,4-dimethylphenyl)amine were used.

Synthesis Example 3

Synthesis of Compound 3

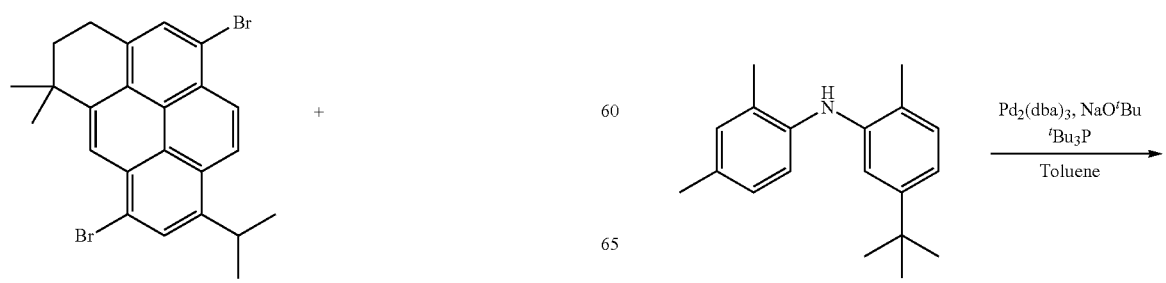

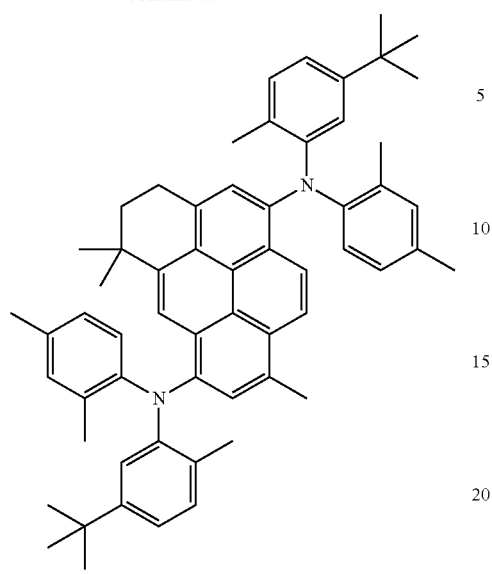

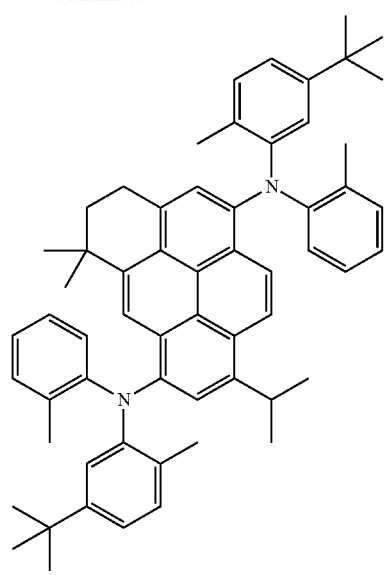

A reaction was performed by the same method as described in Synthesis Example 1, thereby obtaining 5.05 g of Compound 3 with a yield of 62%, except that 4.42 g (10.0 mmol) of 1,7-dibromo-5,5,9-trimethyl-4,5-dihydro-3H-benzo[cd]pyrene and 8.02 g (30 mmol) of N-(5-(tert-butyl)-2-methylphenyl)-2,4-dimethylaniline were used.

A reaction was performed by the same method as described in Synthesis Example 1, thereby obtaining 4.64 g of Compound 4 with a yield of 57%, except that 4.70 g (10.0 mmol) of 1,7-dibromo-9-isopropyl-5,5-dimethyl-4,5-dihydro-3H-benzo[cd]pyrene and 7.60 g (30 mmol) of 5-(tert-butyl)-2-methyl-N-(o-tolyl)aniline were used.

Synthesis Example 4

Synthesis of Compound 4

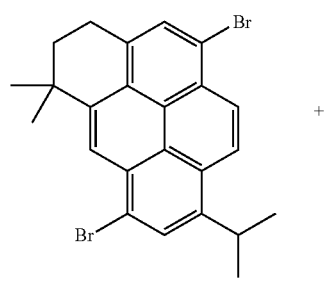

Synthesis Example 5

Synthesis of Compound 5

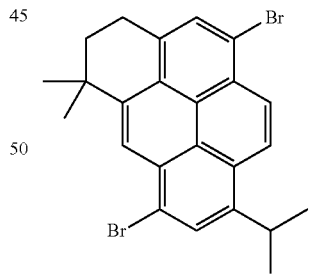

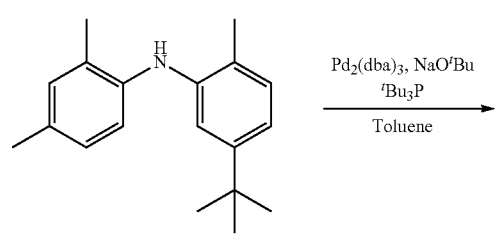

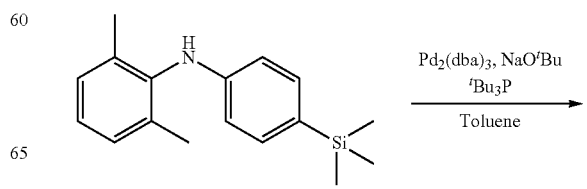

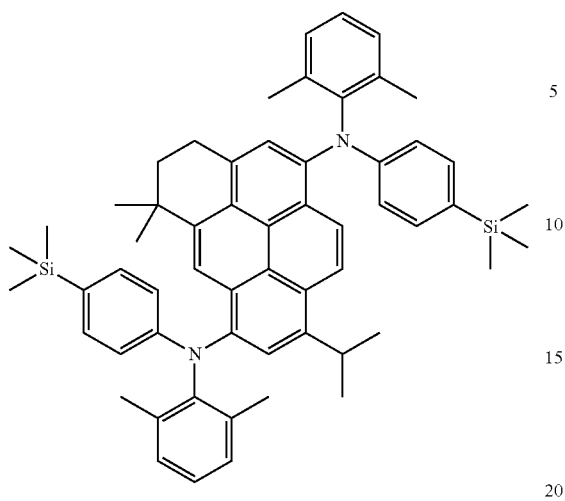

A reaction was performed by the same method as described in Synthesis Example 1, thereby obtaining 6.35 g of Compound 5 with a yield of 75%, except that 4.70 g (10.0 mmol) of 1,7-dibromo-9-isopropyl-5,5-dimethyl-4,5-dihydro-3H-benzo[cd]pyrene and 8.08 g (30 mmol) of 2,6-dimethyl-N-(4-(methyltrimethylsilyl)phenyl)aniline were used.

Synthesis Example 6

Synthesis of Compound 6

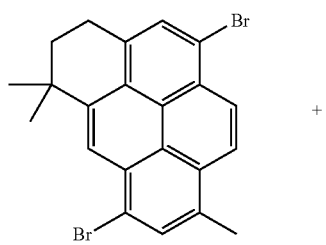

+

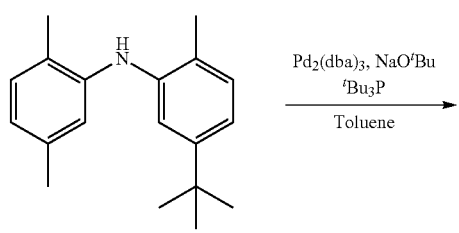

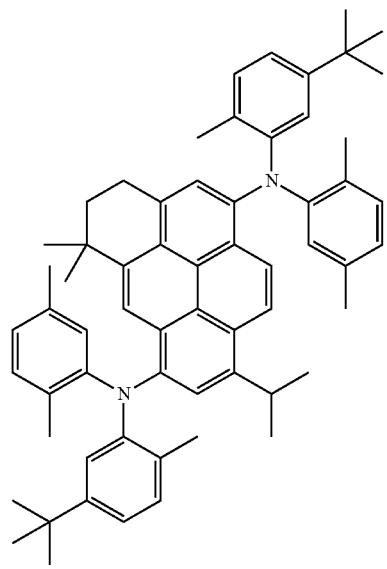

A reaction was performed by the same method as described in Synthesis Example 1, thereby obtaining 5.30 g of Compound 6 with a yield of 65%, except that 4.42 g (10.0 mmol) of 1,7-dibromo-5,5,9-methyltrimethyl-4,5-dihydro-3H-benzo[cd]pyrene and 8.02 g (30 mmol) of 5-(tert-butyl)-N-(2,5-dimethylphenyl)-2-methylaniline were used.

Synthesis Example 7

Synthesis of Compound 7

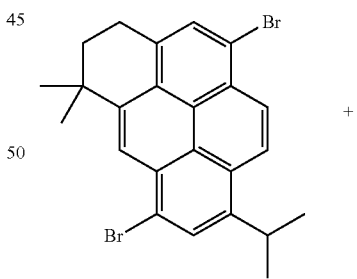

+

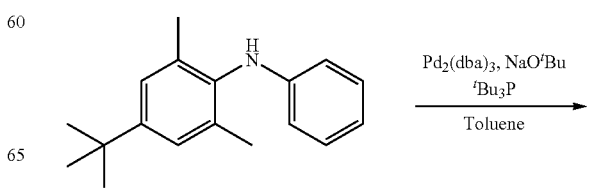

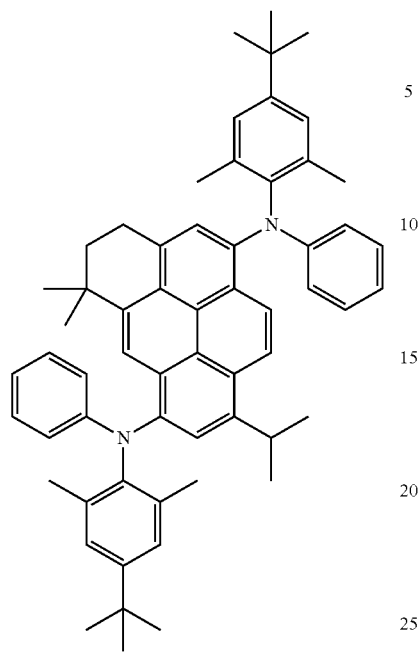

A reaction was performed by the same method as described in Synthesis Example 1, thereby obtaining 4.64 g of Compound 7 with a yield of 57%, except that 4.70 g (10.0 mmol) of 1,7-dibromo-9-isopropyl-5,5-dimethyl-4,5-dihydro-3H-benzo[cd]pyrene and 7.60 g (30 mmol) of 4-(tert-butyl)-2,6-dimethyl-N-phenylaniline were used.

Synthesis Example 8

Synthesis of Compound 8

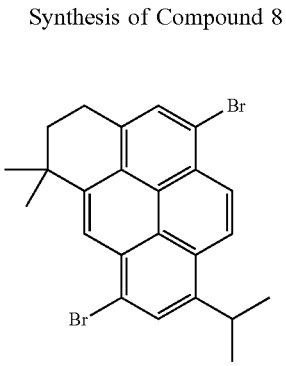

+

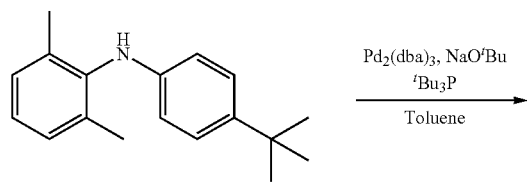

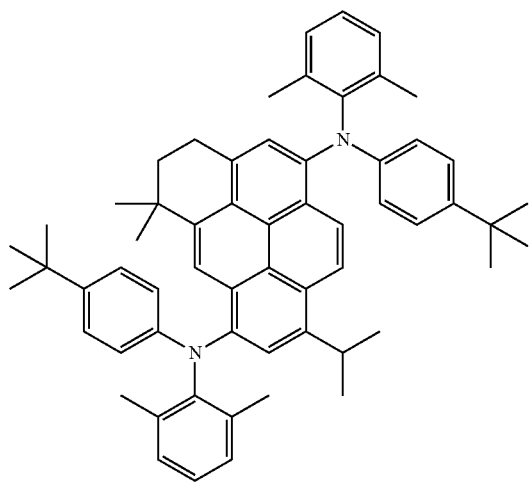

A reaction was performed by the same method as described in Synthesis Example 1, thereby obtaining 4.97 g of Compound 8 with a yield of 61%, except that 4.70 g (10.0 mmol) of 1,7-dibromo-9-isopropyl-5,5-dimethyl-4,5-dihydro-3H-benzo[cd]pyrene and 7.60 g (30 mmol) of N-(4-(tert-butyl)phenyl)-2,6-dimethylaniline were used.

Synthesis Example 9

Synthesis of Compound 9

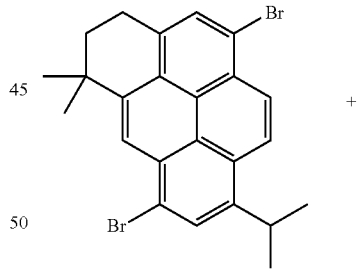

+

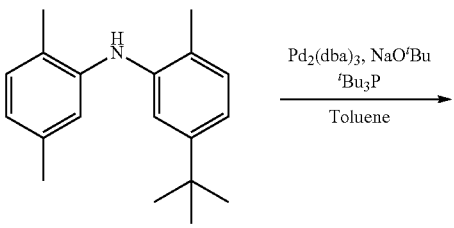

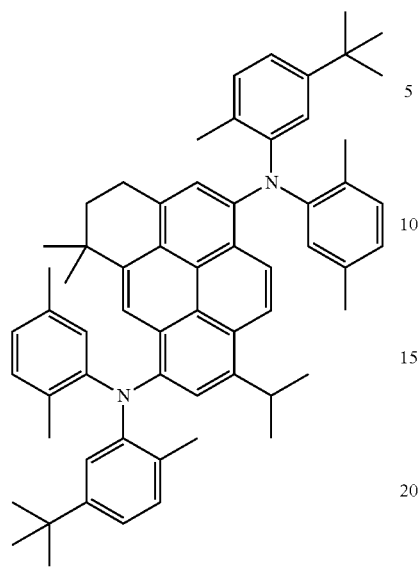
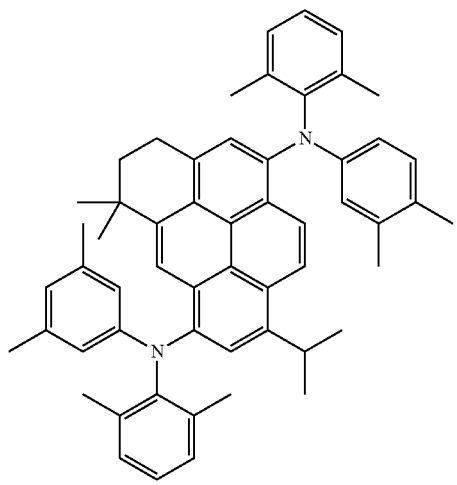

A reaction was performed by the same method as described in Synthesis Example 1, thereby obtaining 5.56 g of Compound 9 with a yield of 66%, except that 4.70 g (10.0 mmol) of 1,7-dibromo-9-isopropyl-5,5-dimethyl-4,5-dihydro-3H-benzo[cd]pyrene and 8.02 g (30 mmol) of 5-(tert-butyl)-N-(2,5-dimethylphenyl)-2-methylaniline were used.

A reaction was performed by the same method as described in Synthesis Example 1, thereby obtaining 4.48 g of Compound 10 with a yield of 59%, except that 4.70 g (10.0 mmol) of 1,7-dibromo-9-isopropyl-5,5-dimethyl-4,5-dihydro-3H-benzo[cd]pyrene and 6.76 g (30 mmol) of N-(3,5-dimethylphenyl)-2,6-dimethylaniline were used.

Synthesis Example 10

Synthesis of Compound 10

Synthesis Example 11

Synthesis of Compound 11

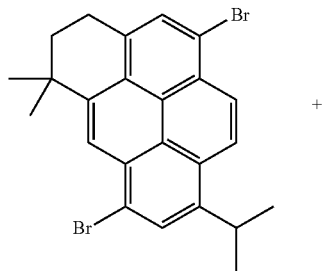
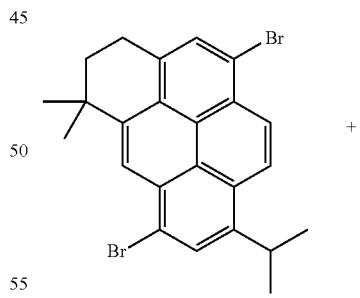
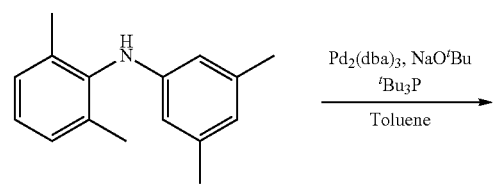
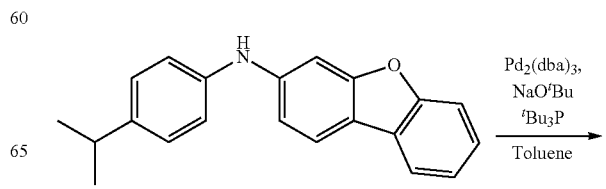

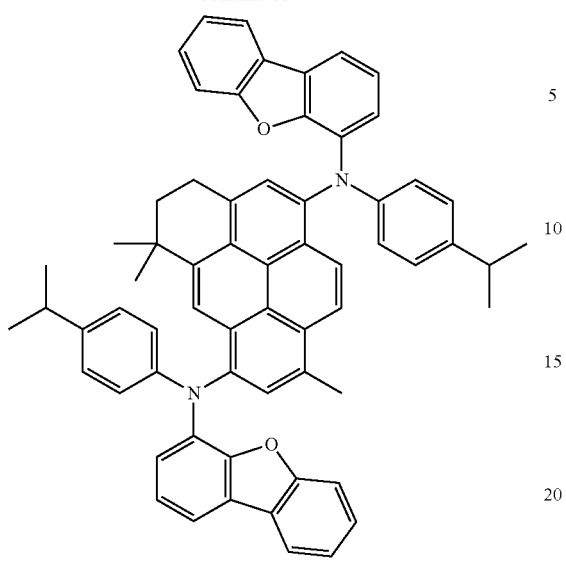

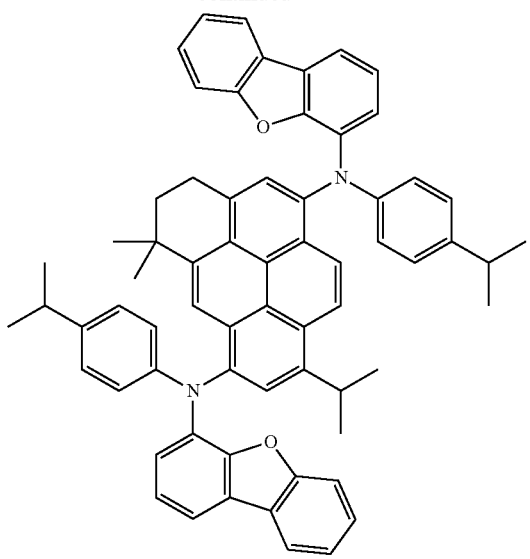

A reaction was performed by the same method as described in Synthesis Example 1, thereby obtaining 5.74 g of Compound 11 with a yield of 65%, except that 4.42 g (10.0 mmol) of 1,7-dibromo-5,5,9-methyltrimethyl-4,5-dihydro-3H-benzo[cd]pyrene and 9.04 g (30 mmol) of N-(4-isopropylphenyl)dibenzo[b,d]furan-3-amine were used.

A reaction was performed by the same method as described in Synthesis Example 1, thereby obtaining 6.38 g of Compound 12 with a yield of 70%, except that 4.70 g (10.0 mmol) of 1,7-dibromo-9-isopropyl-5,5-dimethyl-4,5-dihydro-3H-benzo[cd]pyrene and 9.04 g (30 mmol) of N-(4-isopropylphenyl)dibenzo[b,d]furan-3-amine were used.

Synthesis Example 12

Synthesis of Compound 12

Synthesis Example 13

Synthesis of Compound 13

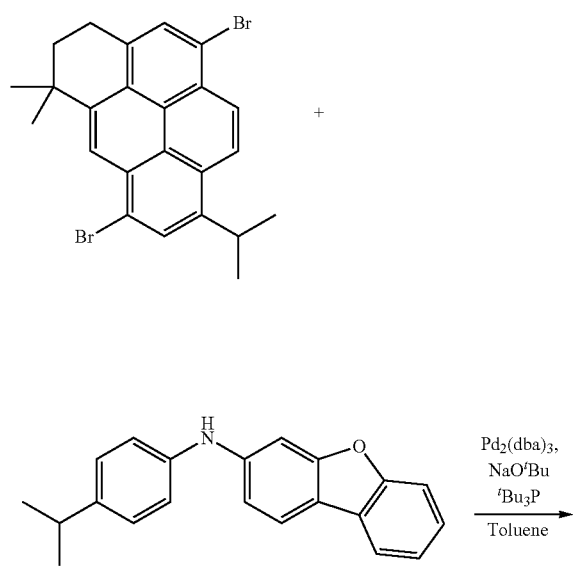

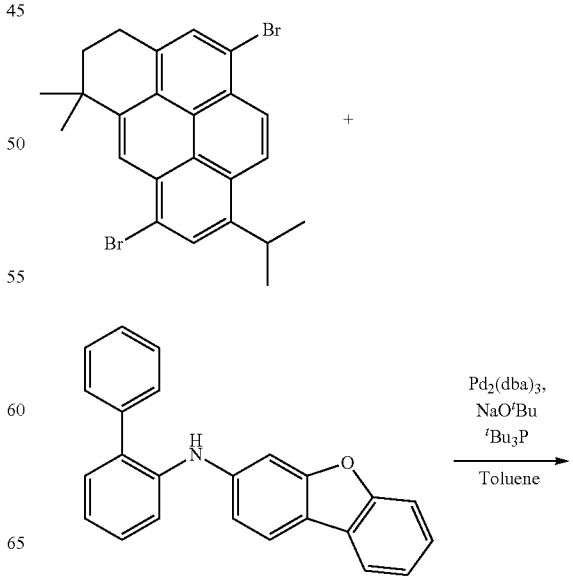

89
-continued

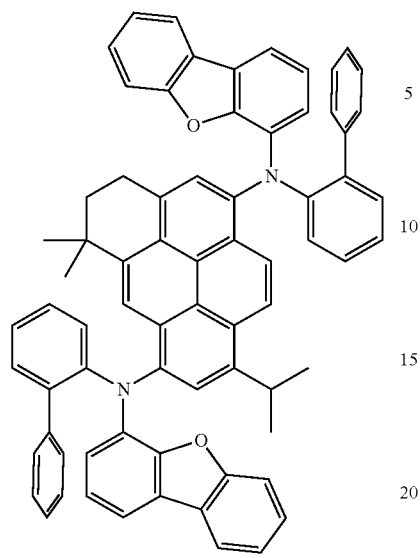

A reaction was performed by the same method as described in Synthesis Example 1, thereby obtaining 5.09 g of Compound 13 with a yield of 52%, except that 4.70 g (10.0 mmol) of 1,7-dibromo-9-isopropyl-5,5-dimethyl-4,5-dihydro-3H-benzo[cd]pyrene and 9.46 g (30 mmol) of N-(1,1'-biphenyl]-2-yl)dibenzo[b,d]furan-3-amine were used.

90
-continued

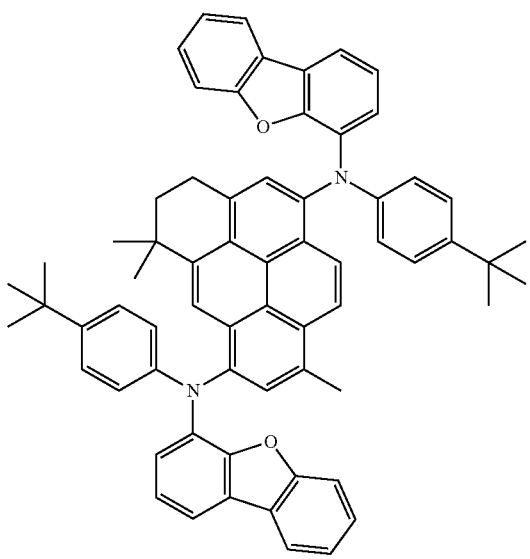

A reaction was performed by the same method as described in Synthesis Example 1, thereby obtaining 6.01 g of Compound 14 with a yield of 66%, except that 4.42 g (10.0 mmol) of 1,7-dibromo-5,5,9-methyltrimethyl-4,5-dihydro-3H-benzo[cd]pyrene and 9.46 g (30 mmol) of N-(4-(tert-butyl)phenyl)dibenzo[b,d]furan-3-amine were used.

Synthesis Example 14

Synthesis of Compound 14

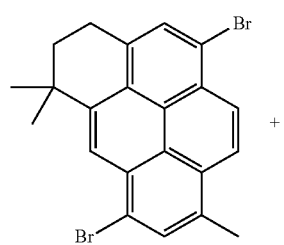

Synthesis Example 15

Synthesis of Compound 15

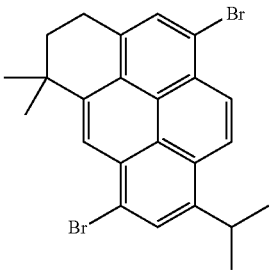

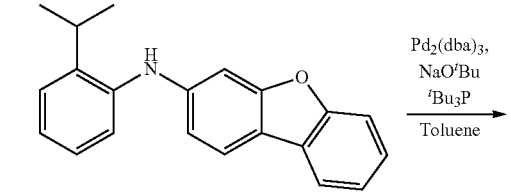

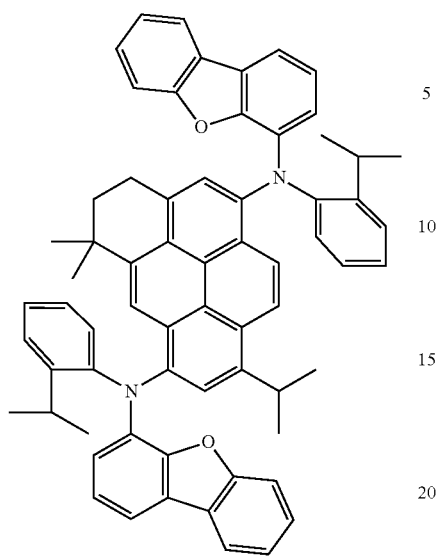

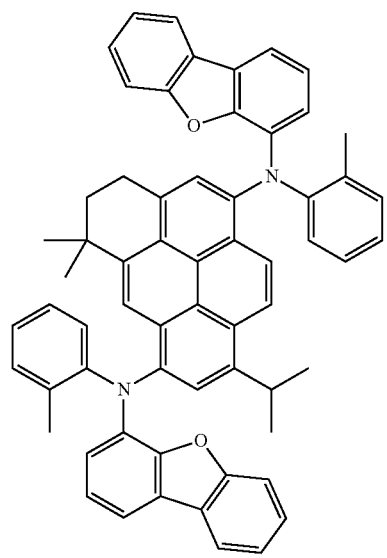

A reaction was performed by the same method as described in Synthesis Example 1, thereby obtaining 4.10 g of Compound 15 with a yield of 45%, except that 4.70 g (10.0 mmol) of 1,7-dibromo-9-isopropyl-5,5-dimethyl-4,5-dihydro-3H-benzo[cd]pyrene and 9.04 g (30 mmol) of N-(2-isopropylphenyl)dibenzo[b,d]furan-3-amine were used.

A reaction was performed by the same method as described in Synthesis Example 1, thereby obtaining 4.70 g of Compound 16 with a yield of 55%, except that 4.70 g (10.0 mmol) of 1,7-dibromo-9-isopropyl-5,5-dimethyl-4,5-dihydro-3H-benzo[cd]pyrene and 8.32 g (30 mmol) of N-(o-tolyl)dibenzo[b,d]furan-3-amine were used.

Synthesis Example 16

Synthesis of Compound 16

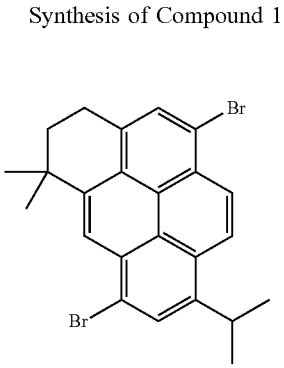

+

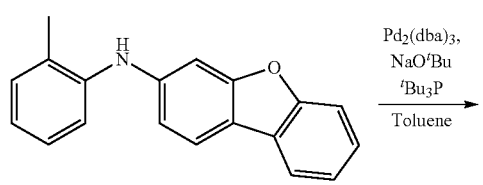

Synthesis Example 17

Synthesis of Compound 17

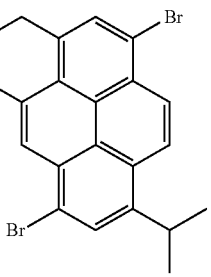

+

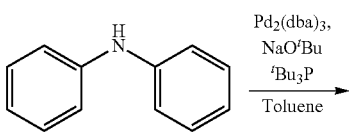

93

-continued

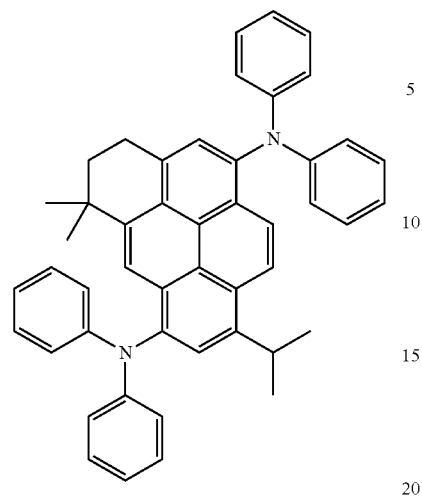

A reaction was performed by the same method as described in Synthesis Example 1, thereby obtaining 4.98 g of Compound 17 with a yield of 77%, except that 4.70 g (10.0 mmol) of 1,7-dibromo-9-isopropyl-5,5-dimethyl-4,5-dihydro-3H-benzo[cd]pyrene and 5.08 g (30 mmol) of diphenylamine were used.

Synthesis Example 18

Synthesis of Compound 18

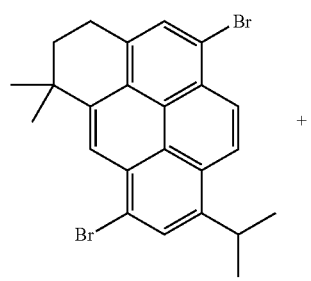

94

-continued

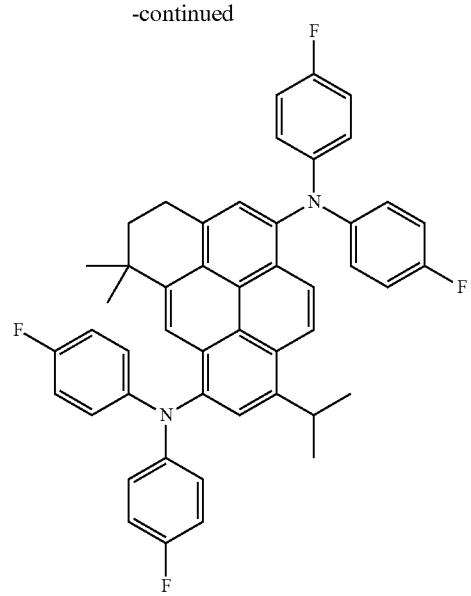

A reaction was performed by the same method as described in Synthesis Example 1, thereby obtaining 4.74 g of Compound 18 with a yield of 66%, except that 4.70 g (10.0 mmol) of 1,7-dibromo-9-isopropyl-5,5-dimethyl-4,5-dihydro-3H-benzo[cd]pyrene and 6.16 g (30 mmol) of bis(4-fluorophenyl)amine were used.

Synthesis Example 19

Synthesis of Compound 19

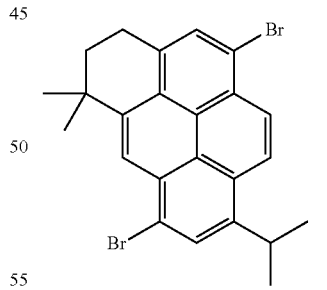

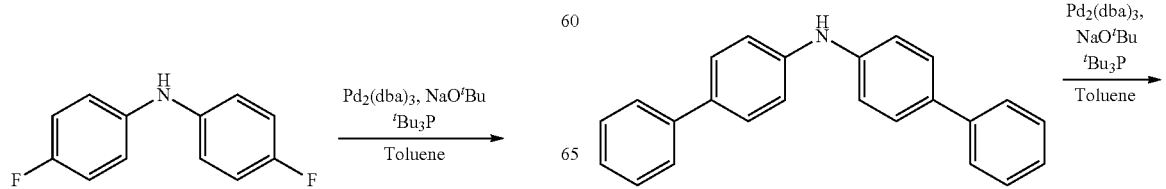

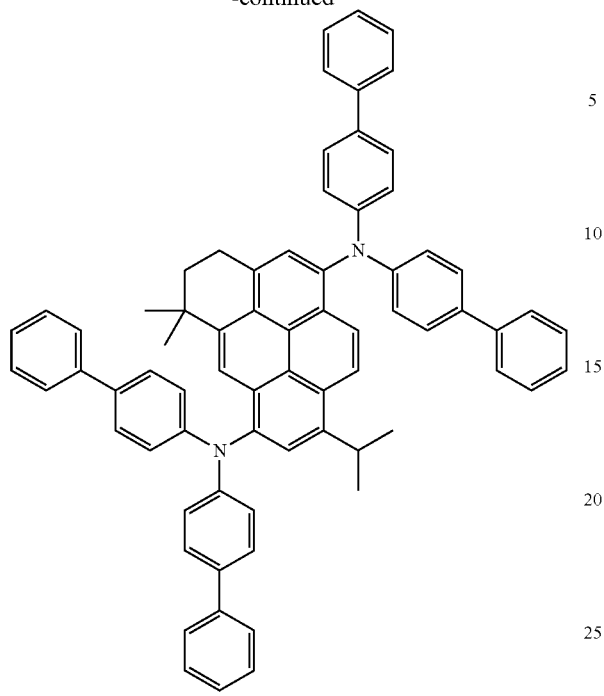

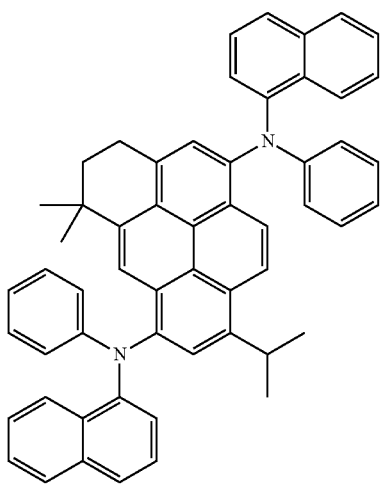

A reaction was performed by the same method as described in Synthesis Example 1, thereby obtaining 3.14 g of Compound 30 with a yield of 42%, except that 4.70 g (10.0 mmol) of 1,7-dibromo-9-isopropyl-5,5-dimethyl-4,5-dihydro-3H-benzo[cd]pyrene and 8.08 g (30 mmol) of di(naphthalene-1-yl)amine were used.

A reaction was performed by the same method as described in Synthesis Example 1, thereby obtaining 5.99 g of Compound 19 with a yield of 63%, except that 4.70 g (10.0 mmol) of 1,7-dibromo-9-isopropyl-5,5-dimethyl-4,5-dihydro-3H-benzo[cd]pyrene and 9.64 g (30 mmol) of di([1,1'-biphenyl]-4-yl)amine were used.

Synthesis Example 21

Synthesis of Compound 21

Synthesis Example 20

Synthesis of Compound 20

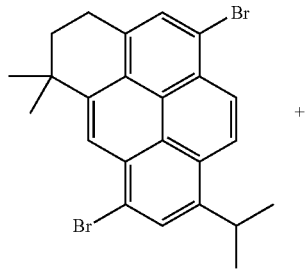

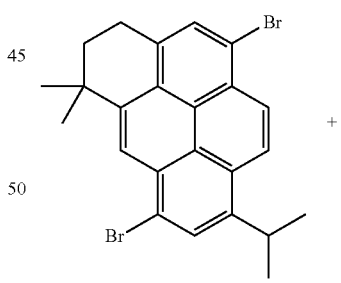

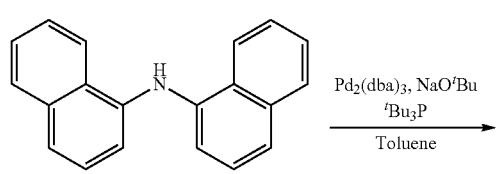

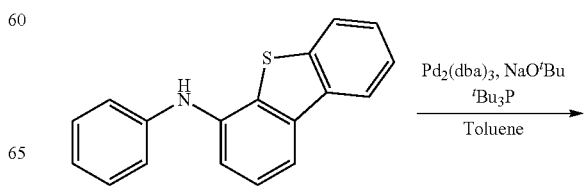

-continued

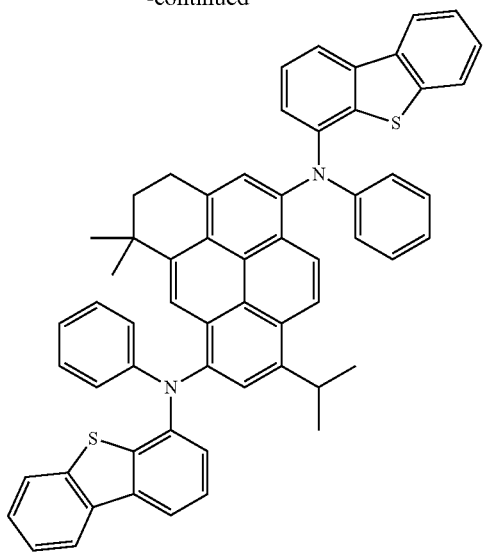

A reaction was performed by the same method as described in Synthesis Example 1, thereby obtaining 5.50 g of Compound 21 with a yield of 64%, except that 4.70 g (10.0 mmol) of 1,7-dibromo-9-isopropyl-5,5-dimethyl-4,5-dihydro-3H-benzo[cd]pyrene and 8.26 g (30 mmol) of N-phenyl dibenzo[b,d]thiophen-4-amine were used.

Synthesis Example 22

Synthesis of Compound 22

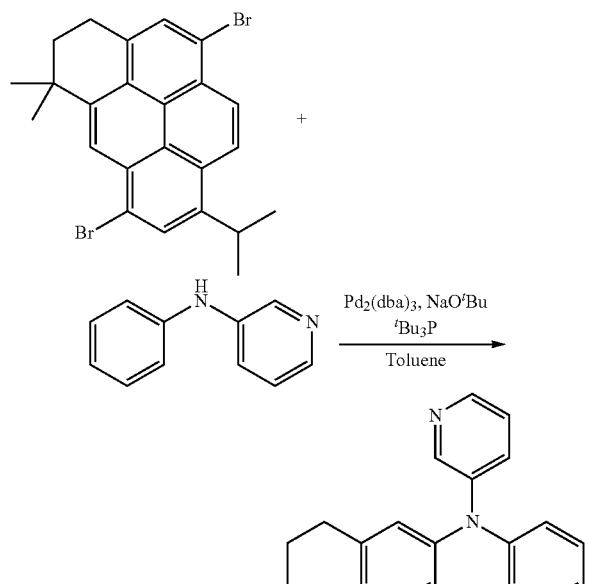

A reaction was performed by the same method as described in Synthesis Example 1, thereby obtaining 2.14 g of Compound 22 with a yield of 33%, except that 4.70 g (10.0 mmol) of 1,7-dibromo-9-isopropyl-5,5-dimethyl-4,5-dihydro-3H-benzo[cd]pyrene and 5.11 g (30 mmol) of N-phenylpyridin-3-amine were used.

Synthesis Example 23

Synthesis of Compound 23

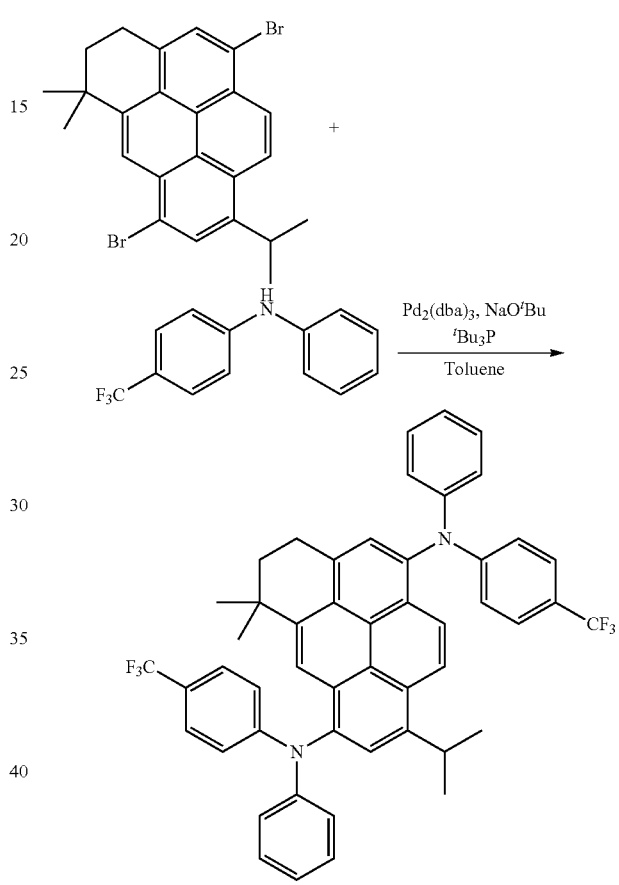

A reaction was performed by the same method as described in Synthesis Example 1, thereby obtaining 3.52 g of Compound 23 with a yield of 45%, except that 4.70 g (10.0 mmol) of 1,7-dibromo-9-isopropyl-5,5-dimethyl-4,5-dihydro-3H-benzo[cd]pyrene and 7.12 g (30 mmol) of N-phenyl-4-(trifluoromethyl)aniline were used.

Synthesis Example 24

Synthesis of Compound 24

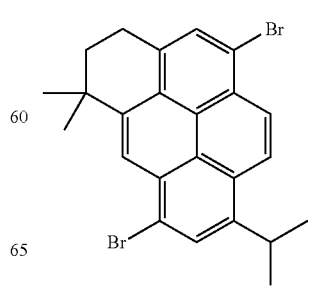

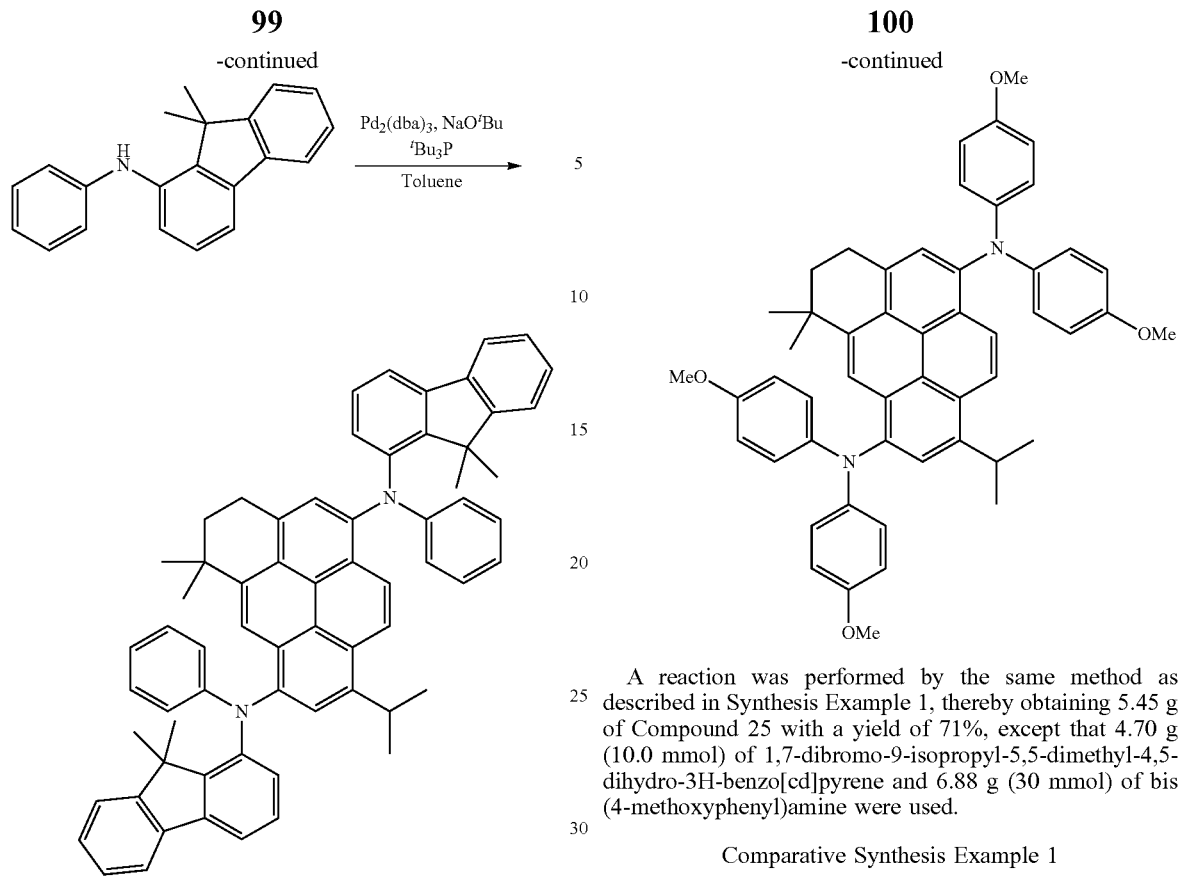

A reaction was performed by the same method as described in Synthesis Example 1, thereby obtaining 5.28 g of Compound 24 with a yield of 60%, except that 4.70 g (10.0 mmol) of 1,7-dibromo-9-isopropyl-5,5-dimethyl-4,5-dihydro-3H-benzo[cd]pyrene and 8.56 g (30 mmol) of 9,9-dimethyl-N-phenyl-9H-fluoren-1-amine were used.

Synthesis Example 25

Synthesis of Compound 25

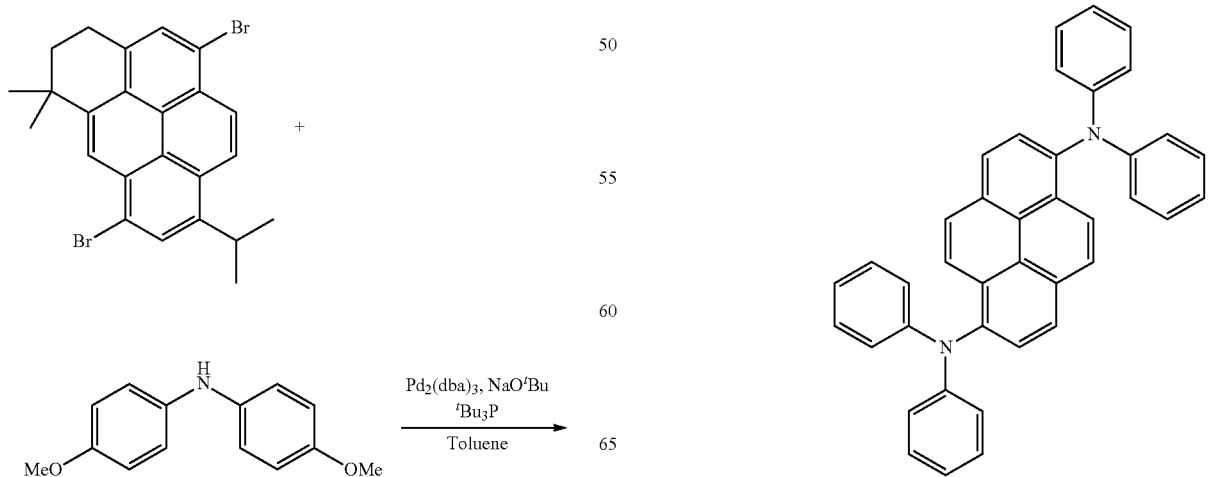

A reaction was performed by the same method as described in Synthesis Example 1, thereby obtaining 5.45 g of Compound 25 with a yield of 71%, except that 4.70 g (10.0 mmol) of 1,7-dibromo-9-isopropyl-5,5-dimethyl-4,5-dihydro-3H-benzo[cd]pyrene and 6.88 g (30 mmol) of bis(4-methoxyphenyl)amine were used.

Comparative Synthesis Example 1

Synthesis of Compound 1-A

A reaction was performed by the same method as described in Synthesis Example 1, thereby obtaining 3.86 g of Compound 1-A with a yield of 72%, except that 3.60 g (10.0 mmol) of 1,6-dibromopyrene and 5.08 g (30 mmol) of diphenylamine were used.

Comparative Synthesis Example 2

Synthesis of Compound 1-B

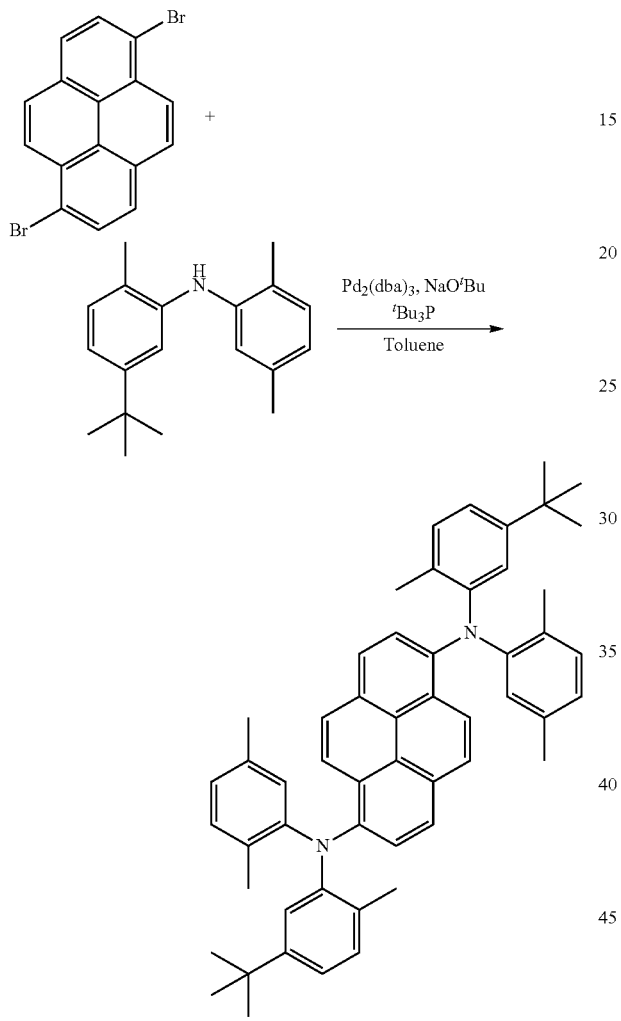

A reaction was performed by the same method as described in Synthesis Example 1, thereby obtaining 4.76 g of Compound 1-B with a yield of 65%, except that 3.60 g (10.0 mmol) of 1,6-dibromopyrene and 8.02 g (30 mmol) of 5-(tert-butyl)-N-(2,5-dimethylphenyl)-2-methylaniline were used.

Comparative Synthesis Example 3

Synthesis of Compound 1-C

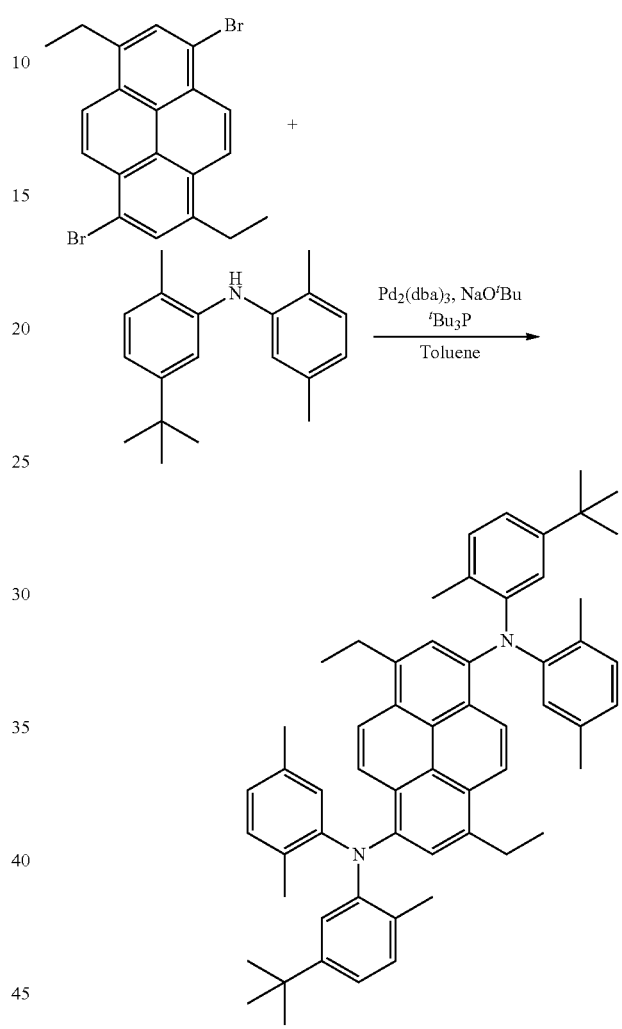

A reaction was performed by the same method as described in Synthesis Example 1, thereby obtaining 4.73 g of Compound 1-C with a yield of 60%, except that 4.16 g (10.0 mmol) of 1,6-dibromo-3,8-diethylpyrene and 8.02 g (30 mmol) of 5-(tert-butyl)-N-(2,5-dimethylphenyl)-2-methylaniline were used.

TABLE 1

| Material No. | $^1$H NMR (400 MHz, ppm) |
|---|---|
| A | CDCl$_3$: δ = 8.38 (d, J = 9.2 Hz, 1H), 8.20 (d, J = 8.0 Hz, 1H), 8.16 (d, J = 7.6 Hz, 1H), 8.14 (d, J = 9.2 Hz, 1H), 7.98 (s, 1H), 7.96 (d, J = 8.0 Hz, 1H), 7.87 (d, J = 7.6 Hz, 1H), 3.43 (t, J = 6.4 Hz, 2H), 2.06 (t, J = 6.8 Hz, 2H), 1.53 (s, 6H) |
| 1 | C$_6$D$_6$: δ = 8.30-8.20 (m, 1H), 8.15-8.05 (m, 1H), 7.96-7.88 (m, 1H), 7.78-7.71 (m, 1H), 7.63-7.57 (m, 1H), 7.38-7.30 (m, 2H), 7.24-7.12 (m, 2H), 7.11-6.94 (m, 4H), 6.92-6.83 (m, 2H), 6.84-6.75 (m, 1H), 6.71-6.56 (m, 2H), 6.71-6.56 (m, 2H), 3.67-3.52 (m, 1H), 2.91-2.73 (m, 2H), 2.91-2.73 (m, 2H), 2.32-1.87 (m, 18H), 1.66-1.55 (m, 2H), 1.24-1.12 (m, 24H), 0.91-0.87 (m, 6H) |

Caption for NMR results table: NMR results for Compounds of Synthesis Examples and Comparative Synthesis Examples TABLE 1-continued NMR results for Compounds of Synthesis Examples and Comparative Synthesis Examples

| Material No. | $^1$H NMR (400 MHz, ppm) |
|---|---|
| 2 | $C_6D_6$: δ = 8.27 (d, 1H), 8.13 (s, 1H), 7.93 (d, 1H), 7.70 (s, 1H), 7.53 (s, 1H), 7.11 (t, 2H), 7.00 (s, 2H), 6.97-6.68 (m, 4H), 8.82 (d, 1H), 6.79 (d, 1H), 6.67 (t, 2H), 3.59 (m, 1H), 2.83 (t, 2H), 2.30 (s, 6H), 2.16 (s, 3H), 2.14 (s, 3H), 2.12 (s, 3H), 2.10 (s, 3H), 2.02 (s, 3H), 1.96 (s, 3H), 1.59 (t, 2H), 1.22 (s, 6H), 1.13 (d, 6H) |
| 3 | $C_6D_6$: δ = 8.28-8.18 (m, 1H), 8.17-8.05 (m, 1H), 7.80-7.71 (m, 1H), 7.63-7.58 (m, 2H), 7.36-7.30 (m, 1H), 7.22-6.97 (m, 7H), 6.92-6.73 (m, 3H) 6.75-6.58 (m, 1H), 2.90-2.73 (m, 2H), 2.40-1.90 (m, 21H), 1.66-1.55 (m, 2H), 1.25-1.16 (m, 18H), 0.91-0.87 (m, 6H) |
| 4 | $C_6D_6$: δ = 8.26 (d, 1H), 8.24 (d, 1H), 8.12 (s, 1H), 8.10 (d, 1H), 7.93 (d, 3H), 7.72 (s, 2H), 7.70 (d, 1H) 7.58 (s, 2H), 7.30 (m, 4H), 6.97 (d, 2H), 3.62-3.56 (m, 1H), 2.83-2.71 (m, 2H), 2.27-2.21 (m, 6H), 1.99-1.85 (m, 6H), 1.65-1.57 (m, 2H), 1.27-1.13 (m, 24H), 0.89-0.86 (m, 6H) |
| 5 | $CDCl_3$: δ = 8.11-7.77 (m, 5H), 7.45 (s, 1H), 7.25-7.13 (m, 9H), 6.70-6.50 (m, 4H), 3.86 (m, 1H), 3.14 (t, 2H), 2.11 (d, 12H), 1.85 (t, 2H), 1.27 (d, 6H), 1.08 (s, 6H), 0.20 (d, 18H) ppm. |
| 6 | $C_6D_6$: δ = 8.30-8.18 (m, 2H), 7.79-7.62 (m, 3H), 7.37-7.32 (m, 1H), 7.22-7.00 (m, 7H), 6.88-6.72 (m, 4H), 2.90-2.75 (m, 2H), 2.38-2.33 (m, 3H), 2.29-2.21 (m, 6H), 2.20-1.87 (m, 9H), 1.67-1.53 (m, 5H), 1.26-1.13 (m, 18H), 0.91-0.85 (m, 6H) |
| 7 | $C_6D_6$: δ = 8.34 (d, 1H), 8.23 (s, 1H), 7.85 (d, 1H), 7.78 (s, 1H), 7.56 (s, 1H), 7.26 (s, 2H), 7.23 (s, 2H), 7.07-6.99 (m, 4H), 6.84-6.73 (m, 6H), 3.59 (m, 1H), 2.77 (t, 2H), 2.30 (s, 6H), 2.26 (s, 6H), 1.61 (t, 2H), 1.32 (s, 9H), 1.30 (s, 9H), 1.19 (s, 6H), 1.15 (d, 6H) |
| 8 | $C_6D_6$: δ = 8.34 (d, 1H), 8.18 (s, 1H), 7.76 (d, 1H), 7.69 (s, 1H), 7.55 (s, 1H), 7.18-7.14 (m, 2H), 7.12-7.06 (m, 8H), 6.83 (d, 2H), 6.75 (d, 2H), 3.51 (m, 1H), 2.84 (t, 2H), 2.26 (s, 6H), 2.23 (s, 6H), 1.62 (t, 2H), 1.25 (s, 9H), 1.23 (s, 9H), 1.14 (s, 6H), 1.12 (d, 6H) |
| 9 | $C_6D_6$: δ = 8.31-8.00 (m, 2H), 7.96-7.94 (m, 1H), 7.90-7.73 (m, 1H), 7.65 (t, 1H) 7.38-7.32 (m, 1H), 6.94-7.24 (m, 7H) 6.72-6.90 (m, 4H), 3.65-3.53 (m, 1H), 2.95-2.75 (m, 2H), 230-2.21 (m, 6H), 2.02-1.82 (m, 9H), 1.68-1.53 (m, 5H), 1.24-1.01 (m, 24H), 0.90-0.84 (m, 6H) |
| 10 | $C_6D_6$: δ = 8.39 (d, 1H), 8.26 (s, 1H), 7.86 (d, 1H), 7.75 (s, 1H), 7.58 (s, 1H), 7.08 (s, 2H), 7.70 (s, 4H), 7.63 (d, 4H), 6.48-6.44 (m, 2H), 3.60 (m, 1H), 2.86 (t, 2H), 2.29 (s, 6H), 2.25 (s, 6H), 1.92 (s, 12H), 1.64 (t, 2H), 1.20 (s, 6H), 1.17 (d, 6H) |
| 11 | $CDCl_3$: δ = 8.25 (d, 1H), 8.15 (s, 1H), 7.97 (t, 3H), 7.80 (s, 1H), 7.72 (s, 1H), 7.68 (d, 2H), 7.44-7.37 (m, 4H), 7.33 (t, 2H), 7.16 (m, 2H), 7.10 (t, 2H), 7.03 (t, 4H), 6.83 (d, 2H), 6.77 (d, 2H), 3.21 (t, 2H), 2.86 (m, 2H), 2.79 (s, 3H), 1.83 (t, 2H), 1.23 (d, 12H), 1.07 (s, 6H) ppm. |
| 12 | $CDCl_3$: δ = 8.25 (d, 1H), 8.17 (s, 1H), 8.13 (d, 1H), 7.97 (s, 2H), 7.95 (m, 1H), 7.71 (s, 1H), 7.68 (d, 2H), 7.45-7.30 (m, 6H), 7.20-7.00 (m, 8H), 6.83 (d, 2H), 6.77 (d, 2H), 3.91 (m, 1H), 3.20 (t, 2H), 2.86 (m, 2H), 1.82 (t, 2H), 1.36 (d, 6H), 1.23 (d, 12H), 1.07 (s, 6H) ppm. |
| 13 | $CDCl_3$: δ = 7.94-7.87 (m, 3H), 7.85-7.78 (m, 2H), 7.56-7.07 (m, 23H), 7.02-6.94 (m, 2H), 6.77-6.63 (m, 6H), 6.62-6.56 (m, 1H), 3.73 (m, 1H), 3.03 (t, 2H), 1.73 (t, 2H), 1.21 (d, 6H), 0.95 (s, 6H) ppm. |
| 14 | $CDCl_3$: δ = 8.28 (d, 1H), 8.15 (s, 1H), 8.00 (d, 1H), 7.98 (d, 2H), 7.81 (s, 1H), 7.73-7.67 (m, 3H), 7.45-7.30 (m, 6H), 7.22-7.14 (m, 8H), 6.84 (d, 2H), 6.78 (d, 2H), 3.20 (t, 2H), 2.78 (s, 3H), 1.82 (t, 2H), 1.29 (s, 18H), 1.06 (s, 6H) ppm |
| 15 | $CDCl_3$: δ = 8.10-7.91 (m, 2H), 7.93 (d, 2H), 7.60 (m, 2H), 7.52 (s, 1H), 7.42 (d, 2H), 7.39-7.25 (m, 8H), 7.24-7.20 (m, 2H), 7.18-7.02 (m, 6H), 6.78 (m, 2H), 3.82 (m, 1H), 3.51 (m, 1H), 3.38 (m, 1H), 3.09 (t, 2H), 1.78 (t, 2H), 1.54 (s, 6H), 1.23 (d, 6H), 1.02 (d, 6H), 0.94 (s, 6H) ppm. |
| 16 | $CDCl_3$: δ = 8.05 (d, 2H), 7.73 (s, 1H), 7.91 (d, 2H), 7.65-7.60 (m, 2H), 7.57 (s, 1H), 7.37 (s, 1H), 7.35-7.20 (m, 9H), 7.20-6.93 (m, 7H), 6.87 (d, 1H), 6.76 (s, 1H), 3.81 (m, 1H), 3.11 (t, 2H), 2.11 (d, 6H), 1.80 (t, 2H), 1.18 (d, 6H), 1.03 (s, 6H) ppm. |
| 17 | $CD_2Cl_2$,: δ = 8.20 (d, 1H), 8.14 (d, 1H), 8.05 (s, 1H), 7.82 (s, 1H), 7.62 (s, 1H), 7.23 (d, 4H), 7.20 (d, 4H), 7.10 (d, 4H), 7.07 (d, 4H), 6.94 (t, 4H), 3.98-3.91 (m, 1H), 3.26 (t, 2H), 1.90 (t, 2H), 1.38 (s, 3H), 1.36 (s, 3H), 1.20 (s, 6H) ppm. |
| 18 | $C_6D_6$: δ = 8.27 (d, 1H), 8.18 (s, 1H), 8.01 (d, 1H), 7.81 (s, 1H), 7.55 (s, 1H), 6.88-6.81 (m, 8H), 6.76-6.68 (m, 8H), 3.67 (m, 1H), 2.94 (t, 2H), 1.66 (t, 2H), 1.21 (s, 6H), 1.19 (d, 6H) |
| 19 | $C_6D_6$: δ = 8.51 (d, 1H), 8.40 (s, 1H), 8.09 (s, 1H), 8.03 (d, 1H), 7.79 (s, 1H), 7.52-7.41 (m, 16H), 7.34 (t, 8H), 7.24-7.16 (m, 8H) 7.14-7.06 (m, 4H), 3.67 (m, 1H), 2.93 (t, 2H), 1.65 (t, 2H), 1.23 (s, 6H), 1.20 (d, 6H) |
| 20 | $C_6D_6$: δ = 8.60 (d, 1H), 8.55 (d, 1H), 8.43 (s, 1H), 8.09 (s, 1H), 7.89 (d, 1H), 7.76 (s, 1H), 7.70 (d, 2H), 7.56 (d, 1H), 7.51 (d, 1H), 7.45-7.43 (m, 5H), 7.39 (d, 2H), 7.33 (d, 1H), 7.24-7.17 (m, 7H), 7.11-7.03 (m, 2H), 7.01 (d, 2H), 3.56 (m, 1H), 2.73 (t, 2H), 1.48 (t, 2H), 1.13 (d, 6H), 0.99 (s, 6H) |
| 21 | $^1$H NMR ($CD_2Cl_2$, 400 MHz): ? = 8.19-8.17 (t, 4H), 8.06 (s, 1H), 7.98 (t, 2H), 7.85 (s, 1H), 7.71 (t, 2H), 7.61 (s, 1H), 7.47-7.38 (m, 6H), 7.26-7.19 (m, 6H), 6.98 (m, 4H), 6.91 (d, 2H), 3.89 (t, 1H), 3.16 (t, 2H), 1.81 (t, 2H), 1.32 (s, 3H), 1.30 (s, 3H), 1.04 (s, 6H) ppm. |
| 22 | $CDCl_3$: δ = 8.44-8.38 (m, 3H), 8.21-8.11 (m, 4H), 8.02 (s, 1H), 7.80 (s, 1H), 7.62 (s, 1H), 7.27-7.23 (m, 4H), 7.29-7.20 (m, 6H), 7.03-6.98 (m, 3H), 3.96 (m, 1H), 3.26 (t, 2H), 1.91 (t, 2H), 1.38 (s, 3H), 1.37 (s, 3H), 1.21 (s, 6H) ppm. |
| 23 | $CDCl_3$: δ = 8.23 (d, 1H), 8.11 (d, 1H), 8.00 (s, 1H), 7.82 (s, 1H), 7.63 (s, 1H), 7.42-7.38 (m, 4H), 7.30-7.27 (m, 4H), 7.27 (d, 4H), 7.09-7.04 (m, 4H), 7.00 (d, 2H), 3.98-3.92 (m, 1H), 3.26 (t, 2H), 1.91 (t, 2H), 1.39 (d, 6H), 1.20 (s, 6H) ppm. |

TABLE 1-continued

NMR results for Compounds of Synthesis Examples and Comparative Synthesis Examples

| Material No. | $^1$H NMR (400 MHz, ppm) |
|---|---|
| 24 | $C_6D_6$: δ = 8.49 (d, 1H), 8.40 (1H, s), 8.06 (s, 1H), 7.98 (d, 1H), 7.79 (s, 1H), 7.53~7.57 (m, 2H), 7.50-7.43 (m, 4H), 7.32-7.26 (m, 4H), 7.24-7.08 (M, 12H), 6.90-6.83 (m, 2H), 3.64 (m, 1H), 2.91 (t, 2H), 1.59 (t, 2H), 1.24 (s, 6H), 1.22 (s, 6H), 1.17 (d, 6H), 1.16 (s, 6H) |
| 25 | $C_6D_6$: δ = 8.50 (d, 1H), 8.41 (s, 1H), 8.01 (d, 1H), 7.99 (s, 1H), 7.73 (s, 1H), 7.18-7.14 (m, 8H), 6.76-6.73 (m, 8H), 3.67 (m, 1H), 3.30 (s, 6H), 3.29 (s, 6H), 2.95 (t, 2H), 1.66 (t, 2H), 1.26 (s, 6H), 1.22 (s, 3H), 1.20 (s, 3H) |
| 1-B | $CDCl_3$: δ = 7.95-7.69 (m, 6H), 7.45 (t, 2H), 7.15 (t, 1H), 7.13-6.97 (m, 6H), 6.90 (d, 2H), 6.75 (m, 2H), 6.44 (s, 1H), 2.25 (s, 3H), 2.03 (s, 6H), 2.02 (s, 6H), 1.74 (s, 3H), 1.22 (s, 14H), 0.98 (s, 4H) |

TABLE 2

| | Compound | Maximum emission wavelength (nm) |
|---|---|---|
| Synthesis Example 1 | Compound 1 | 456 |
| Synthesis Example 2 | Compound 2 | 456 |
| Synthesis Example 4 | Compound 4 | 452 |
| Synthesis Example 5 | Compound 5 | 456 |
| Synthesis Example 6 | Compound 6 | 456 |
| Synthesis Example 7 | Compound 7 | 454 |
| Synthesis Example 9 | Compound 9 | 453 |
| Synthesis Example 10 | Compound 10 | 455 |
| Synthesis Example 11 | Compound 11 | 454 |
| Synthesis Example 12 | Compound 12 | 454 |
| Synthesis Example 13 | Compound 13 | 454 |
| Synthesis Example 14 | Compound 14 | 454 |
| Synthesis Example 15 | Compound 15 | 451 |
| Synthesis Example 16 | Compound 16 | 449 |
| Synthesis Example 17 | Compound 17 | 453 |
| Synthesis Example 18 | Compound 18 | 453 |
| Synthesis Example 21 | Compound 21 | 454 |
| Synthesis Example 22 | Compound 22 | 448 |
| Synthesis Example 23 | Compound 23 | 446 |
| Comparative Synthesis Example 1 | Compound 1-A | 456 |
| Comparative Synthesis Example 2 | Compound 1-B | 456 |
| Comparative Synthesis Example 3 | Compound 1-C | 456 |

As shown in Table 2, as a result of comparing the maximum emission wavelengths between the compounds of the present invention and the compounds of the comparative synthesis examples, the maximum emission wavelengths of the compounds according to the present invention were the same or shorter wavelengths than those of the compounds of the comparative synthesis examples.

The compounds according to the present invention may be used as a dopant, particularly, a blue dopant, and have shorter emission wavelengths than those of the conventional compounds, and therefore the compounds may exhibit a deep blue color.

Evaluation of Solubility of Organic Compound

The solubility in hexane, toluene and dichloromethane was measured for the compounds of Synthesis Example 9, and Comparative Synthesis Examples 2 and 3. The measurement of solubility was carried out at room temperature, and the results are shown in the following table.

TABLE 3

| Comparison of solubility | Compound 9 (Synthesis Example 9) | Compound 1-B (Comparative Synthesis Example 2) | Compound 1-C (Comparative Synthesis Example 3) |
|---|---|---|---|
| Hexane | 1 g/10 ml | Insoluble | Insoluble |
| Toluene | 1 g/8 ml | 1 g/20,000 ml | 1 g/18,000 mL |
| Dichloromethane | 1 g/5 ml | 1 g/2,000 mL | 1 g/1,800 ml |

As shown in Table 3, Compound 1-B and Compound 1-C conventionally used as a blue dopant exhibited significantly lower solubility than Compound 9.

Example 1: Manufacture of OLED

A substrate on which an Ag alloy as a light reflection layer and ITO (10 nm) as an anode of an OLED were sequentially stacked was patterned into cathode and anode areas and an insulation layer through photolithography, and surface-treated with UV ozone and O2:N2 plasma for an increase in the work function of the anode (ITO) and descumming. Thereon, 1,4,5,8,9,11-hexaazatriphenylene-hexacarbonitrile (HAT-CN) as a HIL was formed to have a thickness of 100 Å. Subsequently, a HTL was formed on the HIL to a thickness of 1000 Å by performing vacuum-deposition of N4,N4,N4',N4'-tetra([1,1'-biphenyl]-4-yl)-[1,1'-biphenyl]-4,4'-diamine. N-phenyl-N-(4-(spiro[benzo[de]anthracene-7,9'-fluorene]-2'-yl)phenyl)dibenzo[b,d]furan-4-amine as an EBL was formed on the HTL to have a thickness of 150 Å, and while α,β-ADN was deposited as a host material capable of forming a blue EML as an EML on the EBL, 4% doping with Compound 1 as a dopant was performed, resulting in formation of an EML to a thickness of 200 Å.

On the EML, 2-(4-(9,10-di(naphthalene-2-yl)anthracene-2-yl)phenyl)-1-phenyl-1H-benzo[d]imidazole and LiQ were mixed at a weight ratio of 1:1 and deposited, thereby forming an ETL to a thickness of 360 Å, and as a cathode, magnesium (Mg) and silver (Ag) were mixed at 9:1 and deposited to a thickness of 160 Å. As a capping layer (CPL), N4,N4'-diphenyl-N4,N4'-bis(4-(9-phenyl-9H-carbazole-3-yl)phenyl)-[1,1'-biphenyl]-4,4'-diamine was deposited on the cathode to have a thickness of 63 to 65 nm. As a UV-curable adhesive, a seal cap was laminated on the capping layer (CPL) to protect an OLED from $O_2$ or moisture in air, and therefore, an OLED was obtained.

Examples 2 to 9: Manufacture of OLED

An OLED was manufactured by the same method as described in Example 1, except that, instead of Compound 1, each of Compounds 4 and 5, and Compounds 11 to 16 was used as a dopant, and a doping amount of the dopant was adjusted.

Comparative Example 1: Manufacture of OLED

An OLED was manufactured by the same method as described in Example 1, except that, instead of Compound 1, Compound 1-A was used as a dopant.

Analysis of Properties of OLED

Properties of the OLEDs manufactured in Examples 1 to 9 and Comparative Example 1 were compared at a luminance of 1000 cd/m², and results are shown in Table 4 below.

TABLE 4

| Classification | Compound | Volt | lm/W | Cd/A | CIEx | CIEy | EQE (%) |
|---|---|---|---|---|---|---|---|
| Comparative Example 1 | 1-A | 4.0 | 3.8 | 4.8 | 0.136 | 0.055 | 8.7 |
| Example 1 | 1 | 4.1 | 3.9 | 5.2 | 0.136 | 0.054 | 9.4 |
| Example 2 | 4 | 3.9 | 4.5 | 5.6 | 0.140 | 0.054 | 10.3 |
| Example 3 | 5 | 3.9 | 5.4 | 6.7 | 0.134 | 0.056 | 11.6 |
| Example 4 | 11 | 3.9 | 5.4 | 6.7 | 0.128 | 0.081 | 9.2 |
| Example 5 | 12 | 4.0 | 4.7 | 5.9 | 0.137 | 0.050 | 11.6 |
| Example 6 | 13 | 4.0 | 4.3 | 5.5 | 0.138 | 0.050 | 10.5 |
| Example 7 | 14 | 4.0 | 4.7 | 5.9 | 0.138 | 0.049 | 11.7 |
| Example 8 | 15 | 3.9 | 5.1 | 6.4 | 0.135 | 0.056 | 11.6 |
| Example 9 | 16 | 4.0 | 4.6 | 5.9 | 0.135 | 0.058 | 10.5 |

Referring to Table 4, when the compound according to the present invention is used as a dopant, it can be confirmed that emission efficiency (Cd/A) is improved, compared with the conventionally used compounds.

INDUSTRIAL APPLICABILITY

The present invention relates to a novel organic compound used in an OLED and an OLED including the same. Particularly, the present invention relates to a novel pyrene-based organic compound and an OLED using the same.

The invention claimed is:

1. An organic compound represented by Formula 2 below:

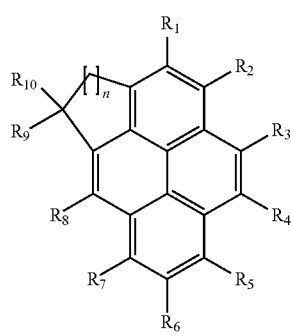

[Formula 2]

wherein n is an integer of 2 forming a saturated ring having 6 carbon atoms, and R₁ to R₈ are the same or different, and each independently selected from the group consisting of hydrogen, deuterium, a halogen, a nitro group, a cyano group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted cycloalkyl group having 3 to 30 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 6 to 30 carbon atoms, a substituted or unsubstituted heteroarylalkyl group having 6 to 30 carbon atoms, a substituted or unsubstituted alkylsilyl group having 1 to 30 carbon atoms, a substituted or unsubstituted arylsilyl group having 6 to 30 carbon atoms and a substituted or unsubstituted aryloxy group having 6 to 30 carbon atoms, and the substituents of R₁ to R₈ may be the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms, wherein any one of R₁ to R₈ is represented by Formula 3 below:

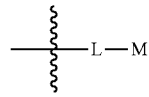

[Formula 3]

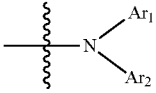

[Formula 4]

wherein L is a single bond, a substituted or unsubstituted arylene group having 6 to 18 carbon atoms, or a substituted or unsubstituted heteroarylene group having 6 to 18 carbon atoms, M is hydrogen, deuterium or a functional group represented by Formula 4, and Ar₁ and Ar₂ are each independently selected from the group consisting of hydrogen, deuterium, a halogen, a cyano group, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 6 to 30 carbon atoms, a substituted or unsubstituted alkylsilyl group having 1 to 30 carbon atoms and a substituted or unsubstituted arylsilyl group having 6 to 30 carbon atoms, Ar₁ and Ar₂ are connected to each other, forming any one of 6- to 18-membered rings including one or more N, O or S, and R₉ and R₁₀ are the same or different, and each independently selected from the group consisting of hydrogen, a substituted or unsubstituted alkyl group having 1 to 10 carbon atoms, a substituted or unsubstituted cycloalkyl group having 3 to 12 carbon atoms, a substituted or unsubstituted alkoxy group having 1 to 10 carbon atoms, a halogen, a cyano group, a substituted or unsubstituted alkylsilyl group having 1 to 30 carbon atoms and a substituted or unsubstituted an arylsilyl group having 6 to 30 carbon atoms, and the substituents of R₉ and R₁₀ are the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms and a heteroalkyl group having 2 to 30 carbon atoms, and the substituents of L, Ar₁ and Ar₂ are the same or different, and each independently deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms; with the proviso that when R9 and R10 is hydrogen, R8 cannot be an alkyl group and when R1-R8 is hydrogen R9 and R10 cannot be hydrogen.

2. The organic compound of claim 1, wherein Ar₁ and Ar₂ are substituents selected from the group consisting of compounds represented by Formulas 5 to 10:

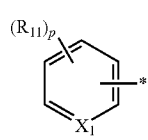

[Formula 5]

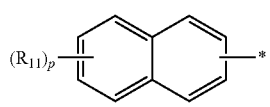

[Formula 6]

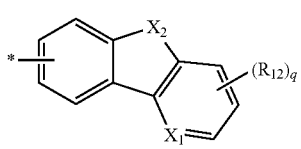

[Formula 7]

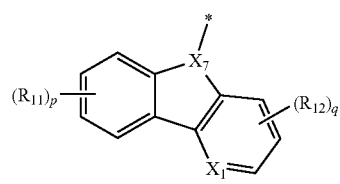

[Formula 8]

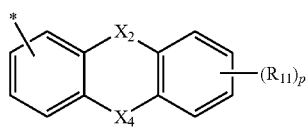

[Formula 9]

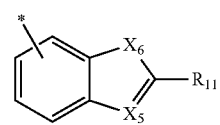

[Formula 10]

wherein * is a site where a bond is formed, p is an integer of 0 to 4, q is an integer of 0 to 3, $X_1$ is selected from the group consisting of $C(R_{13})$, N, S and O, $X_2$, $X_3$, $X_4$ and $X_6$ are the same or different, and each independently selected from the group consisting of $C(R_{13})(R_{14})$, $N(R_{13})$, S and O, $X_5$ and $X_7$ are the same or different, and each independently $C(R_{13})$ or N, $R_{11}$ to $R_{14}$ are the same or different, and each independently selected from the group consisting of hydrogen, deuterium, a halogen, a cyano group, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 6 to 30 carbon atoms, a substituted or unsubstituted alkylsilyl group having 1 to 30 carbon atoms and a substituted or unsubstituted arylsilyl group having 6 to 30 carbon atoms, and the substituents of $R_{19}$ to $R_{21}$ are the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms.

3. The organic compound of claim 1, wherein $Ar_1$ and $Ar_2$ are linked with N of M, forming a ring, and the resulting compound is represented by Formula 11 or 12:

[Formula 11]

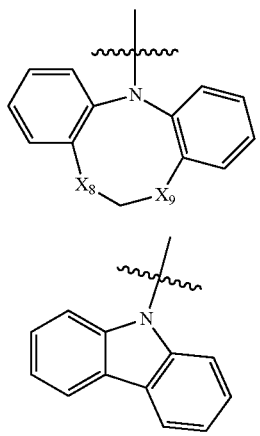

[Formula 12]

wherein $X_8$ and $X_9$ are the same or different, and each independently selected from the group consisting of $C(R_{15})(R_{16})$, $N(R_{15})$, S and O, $R_{15}$ and $R_{16}$ are the same or different, and each independently selected from the group consisting of hydrogen, deuterium, a halogen, a cyano group, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, a substituted or unsubstituted heteroarylalkyl group having 6 to 30 carbon atoms, a substituted or unsubstituted alkylsilyl group having 1 to 30 carbon atoms and a substituted or unsubstituted arylsilyl group having 6 to 30 carbon atoms, and substituents of $R_{15}$ and $R_{16}$ are the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms.

4. The organic compound of claim 1, wherein the compound of Formula 1 is selected from the group consisting of the following compounds:

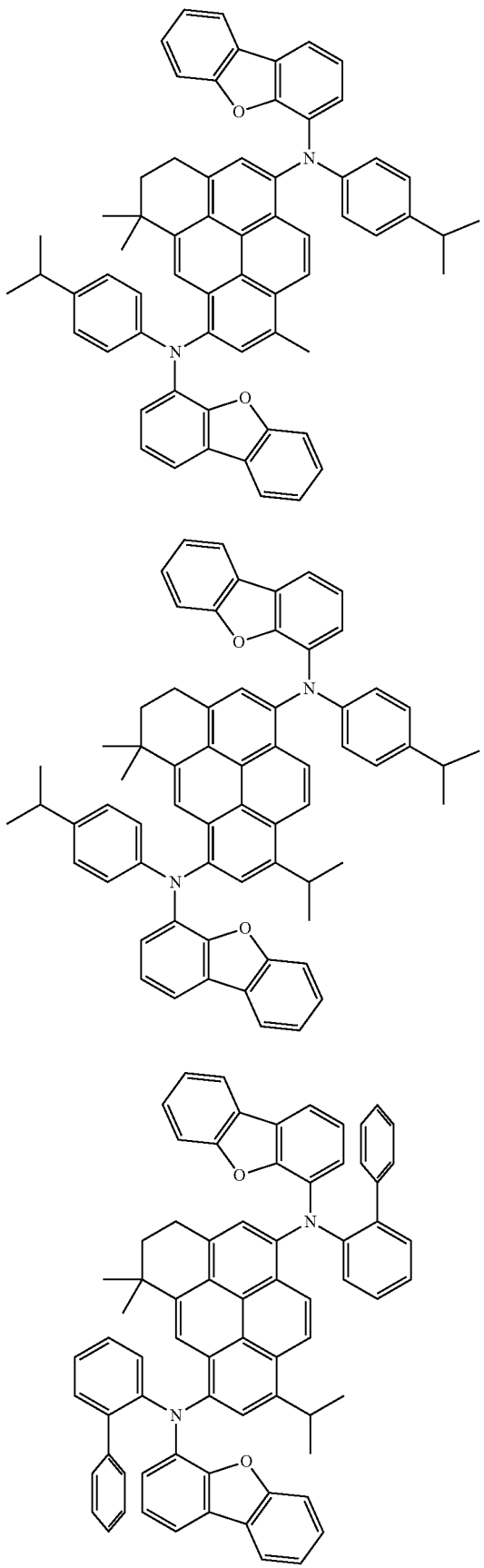

113
-continued
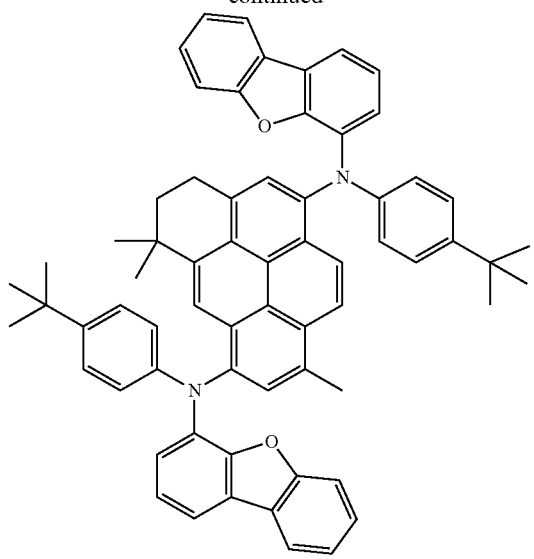
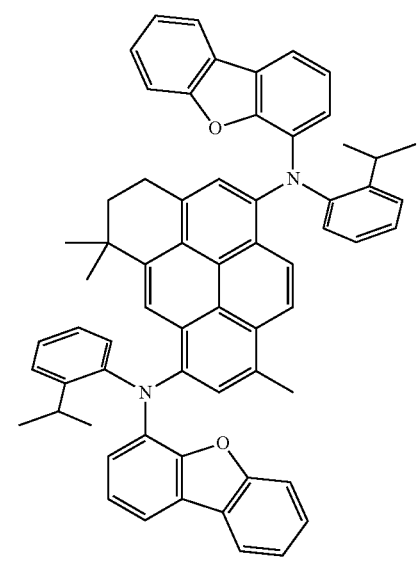
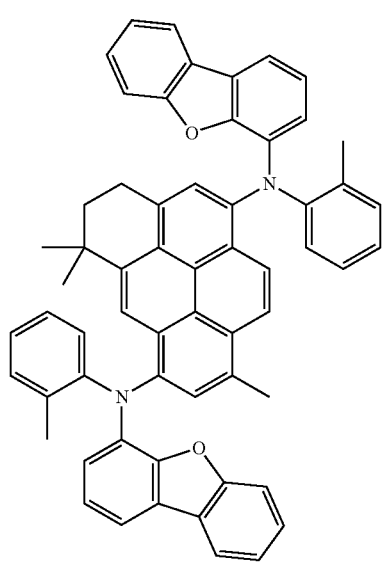
114
-continued
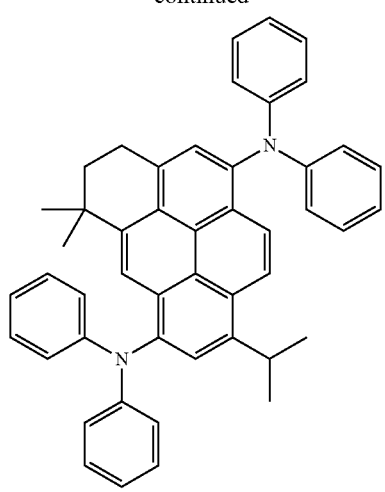
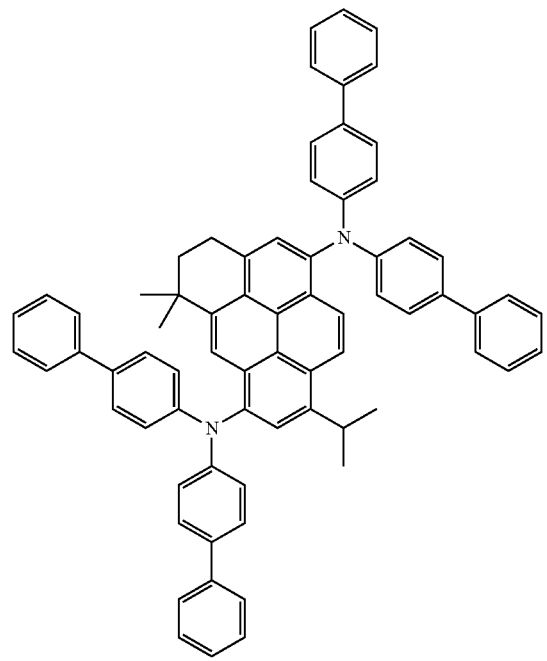
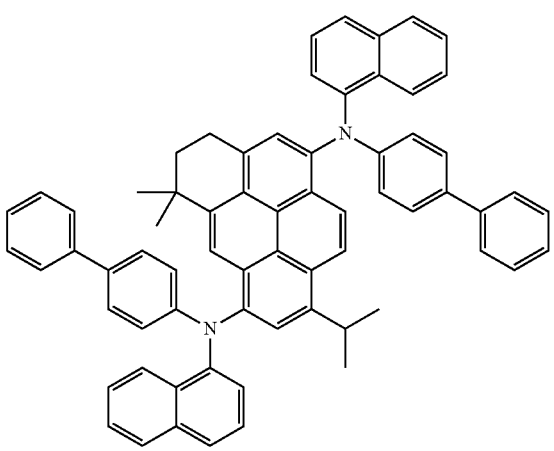

115
-continued
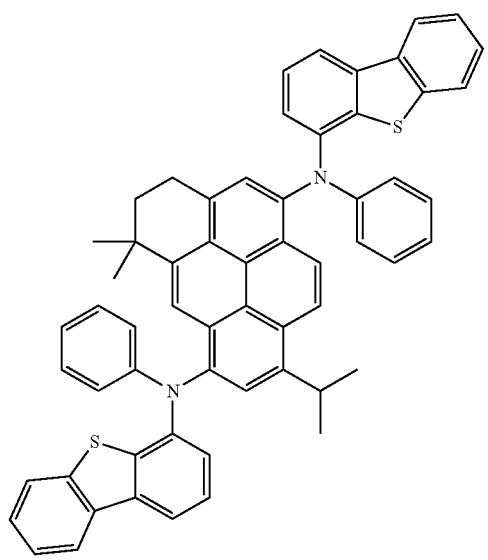
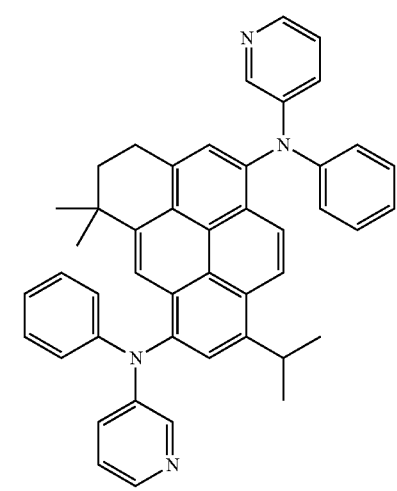
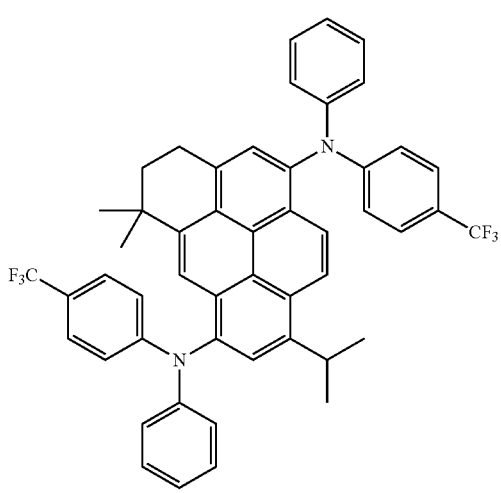
116
-continued
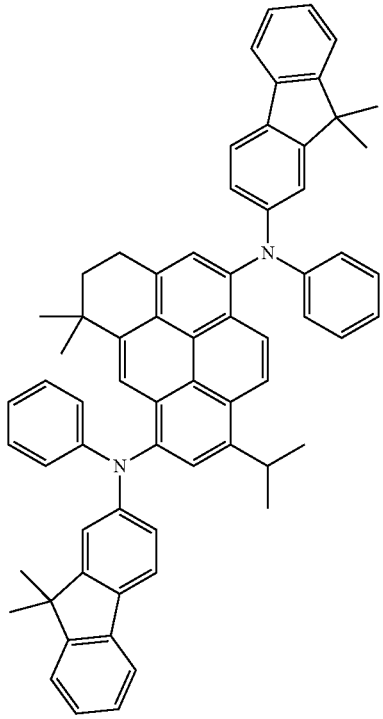
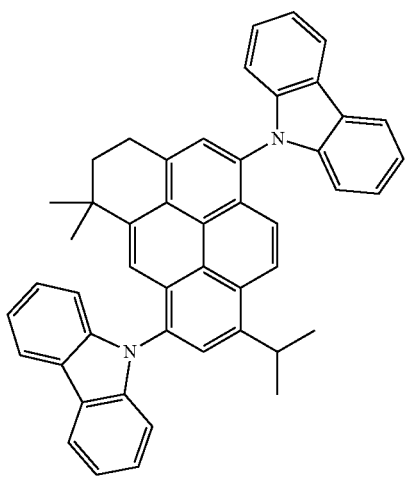
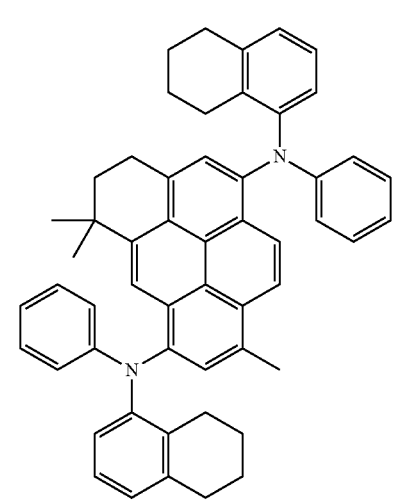

117
-continued
118
-continued
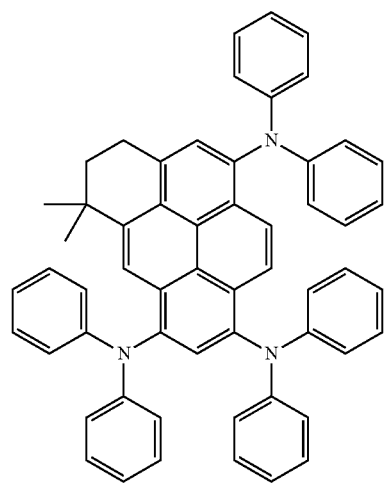
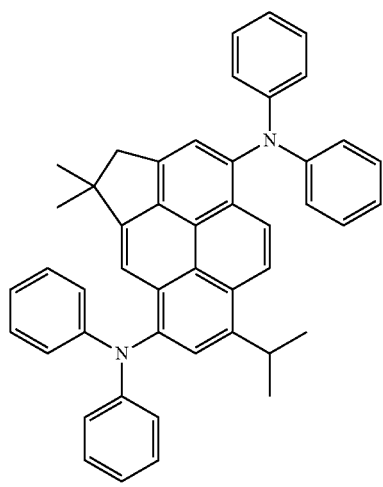
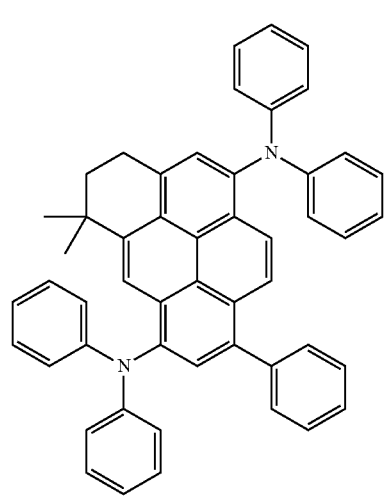
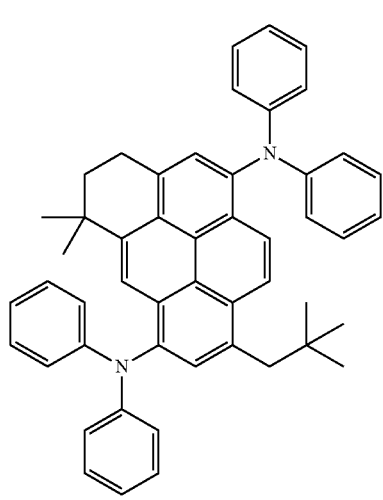
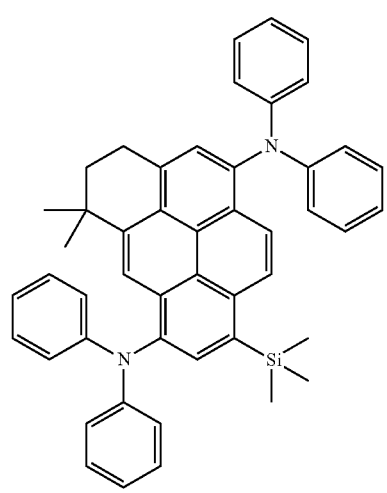
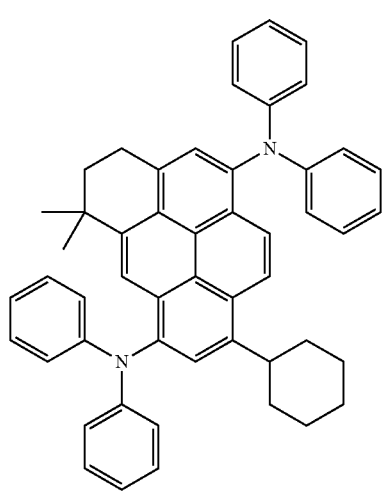

119
-continued
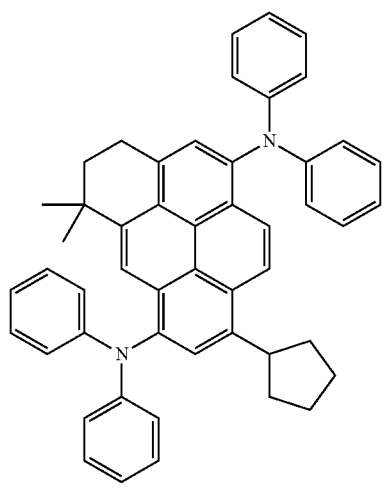
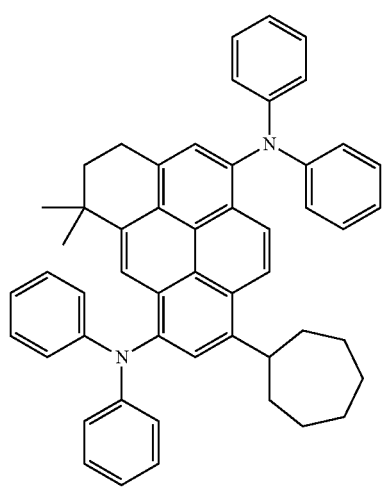
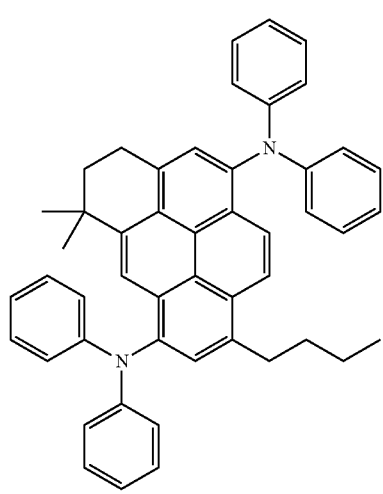
120
-continued
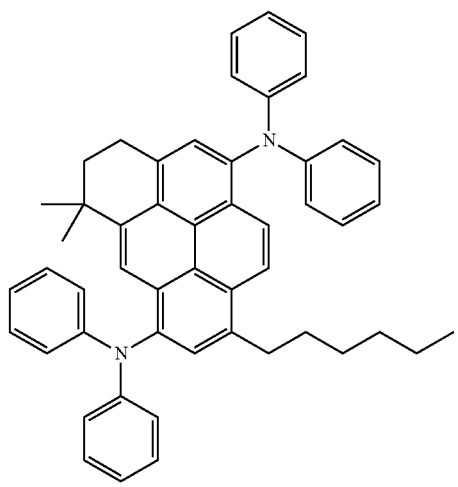
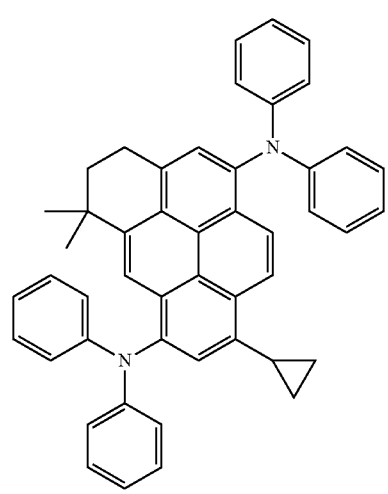
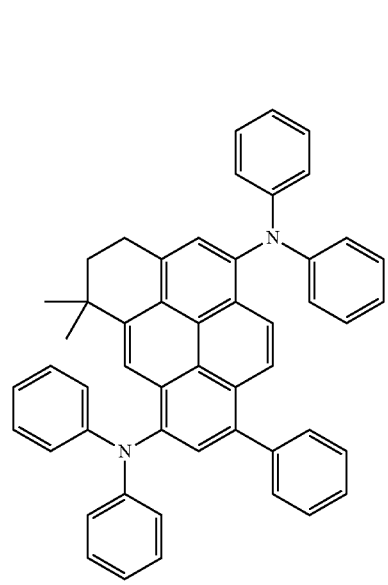

121
-continued
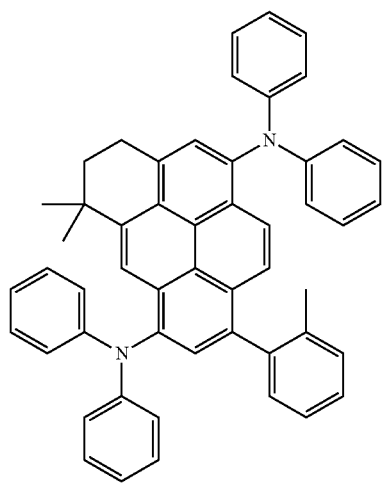
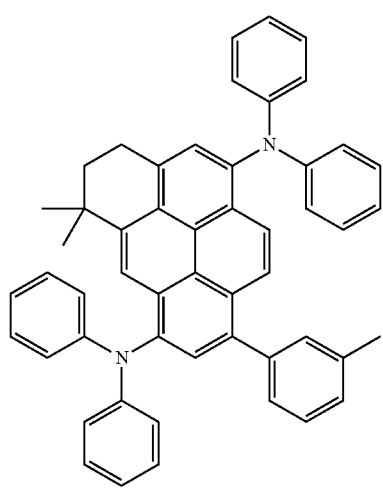
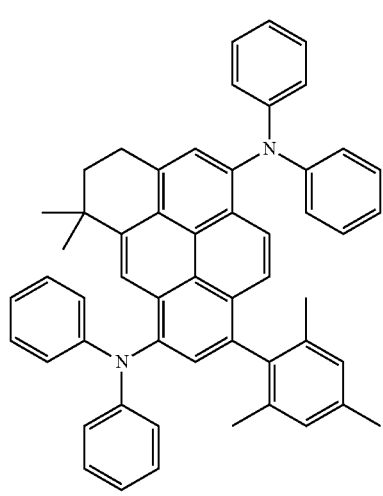
122
-continued
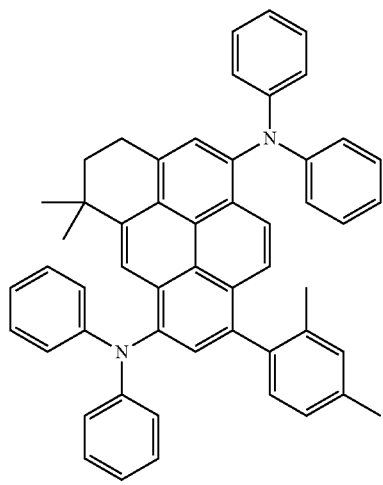
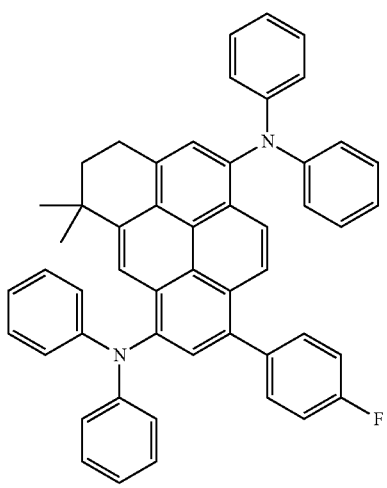
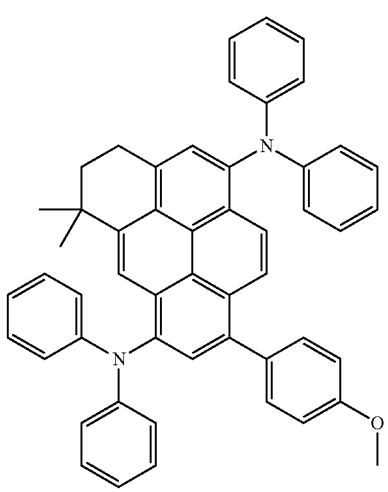

123
-continued
124
-continued
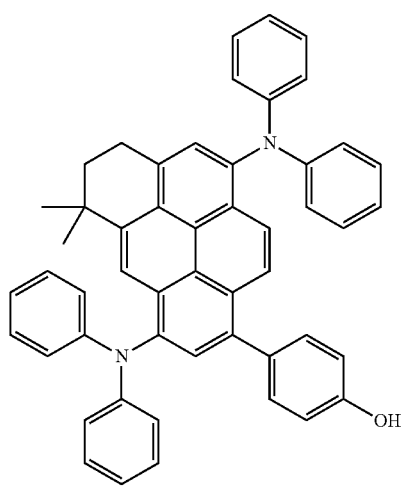
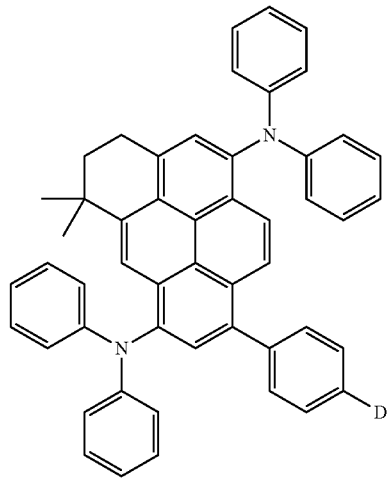
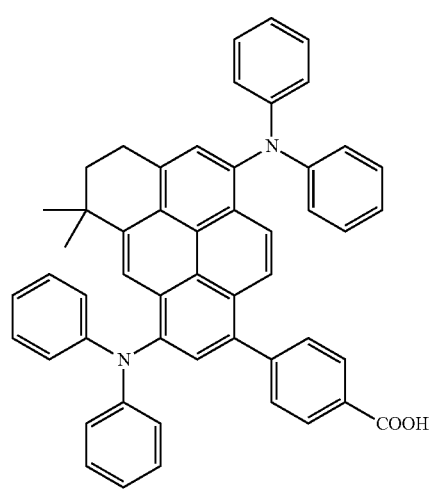
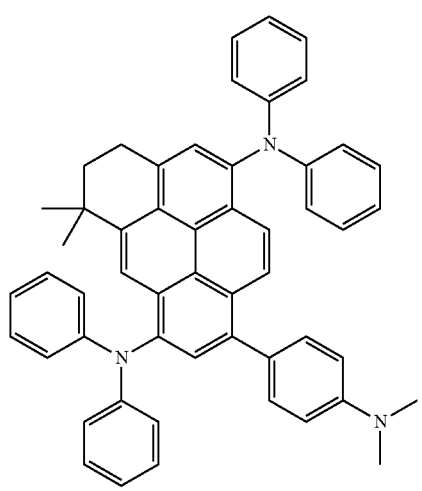
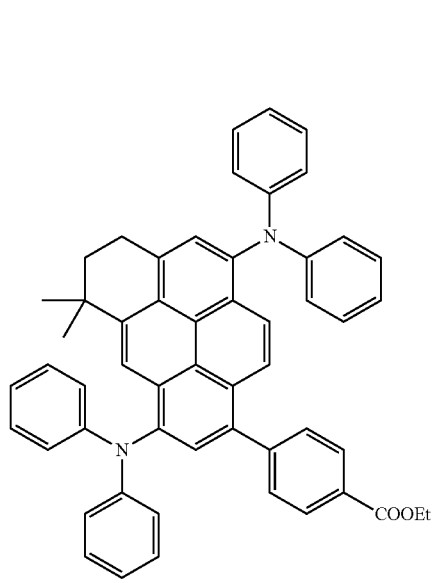
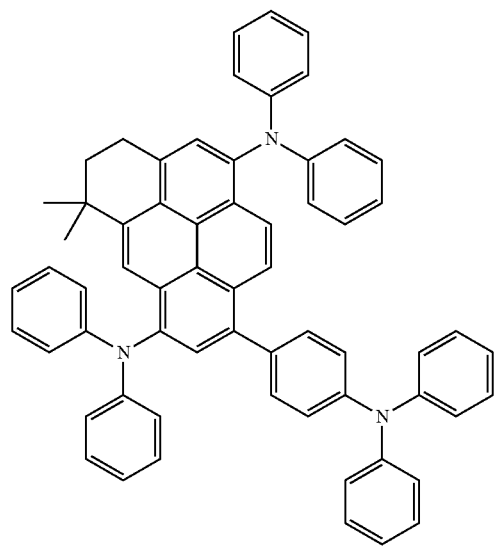

125
-continued
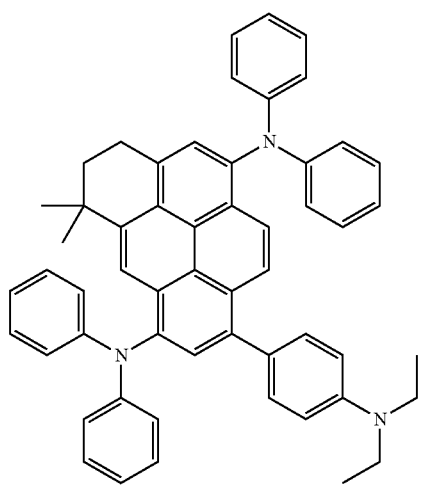
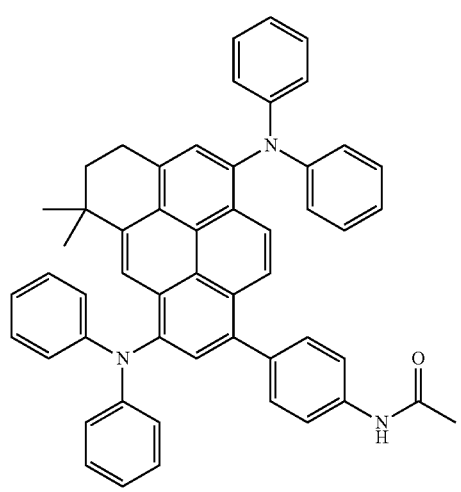
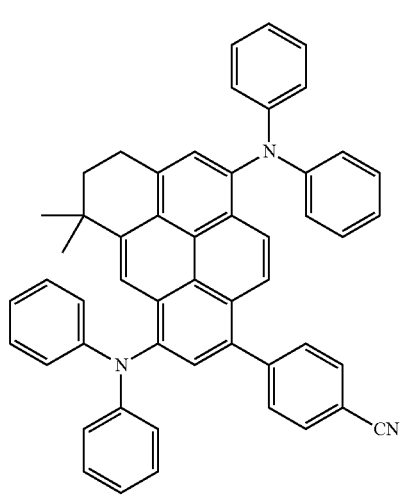
126
-continued
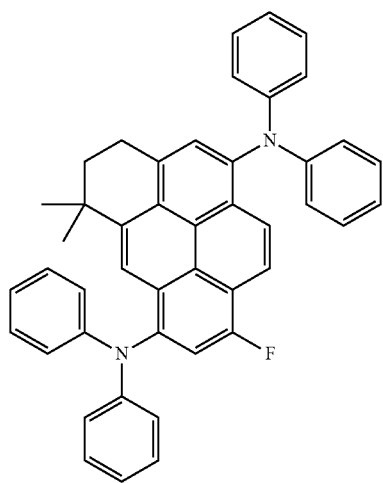
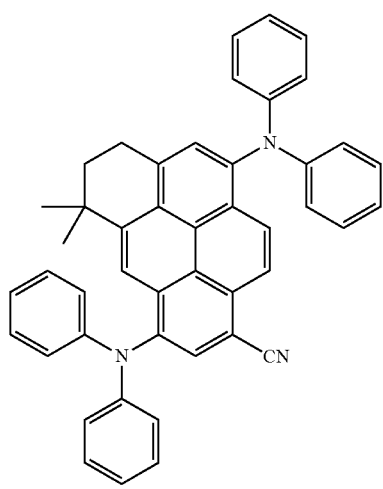
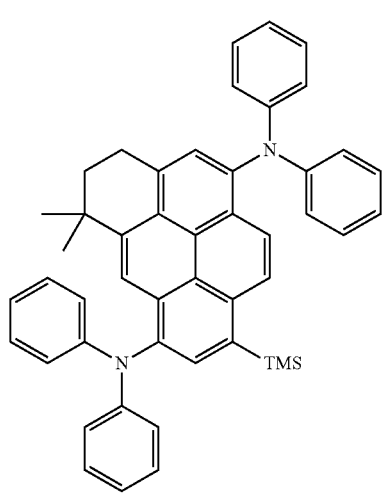

127
-continued
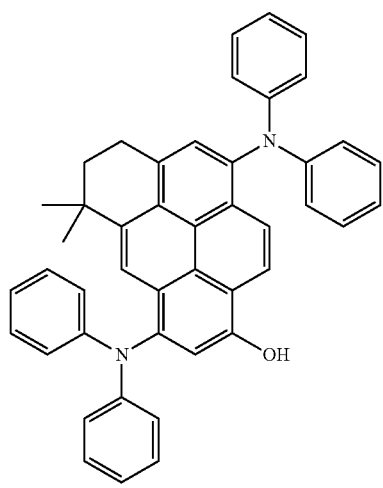
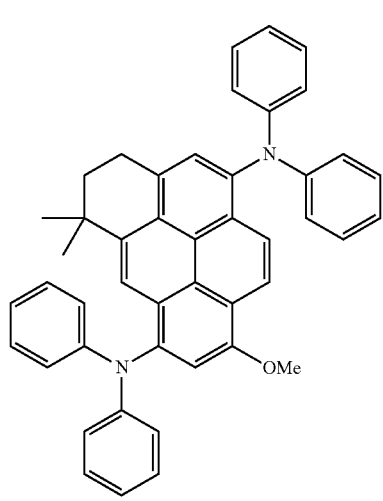
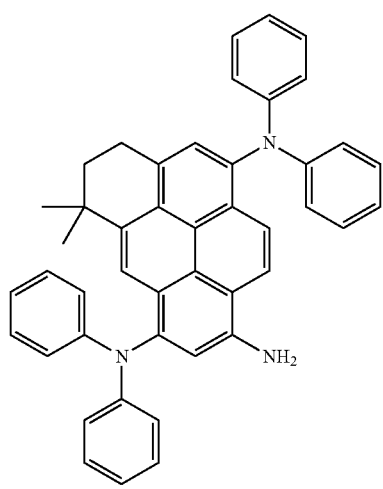
128
-continued
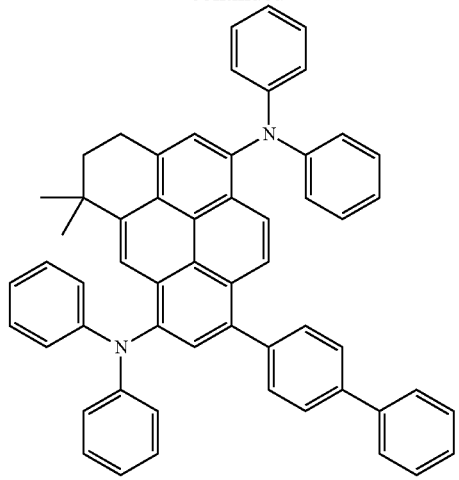
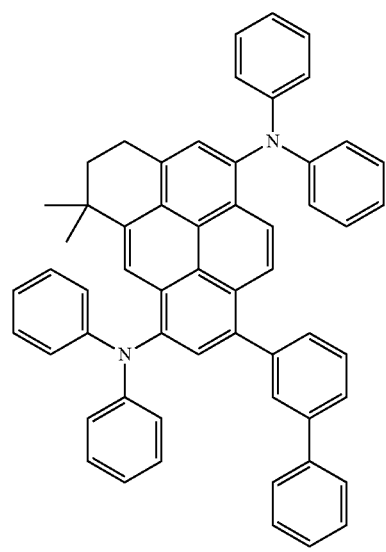
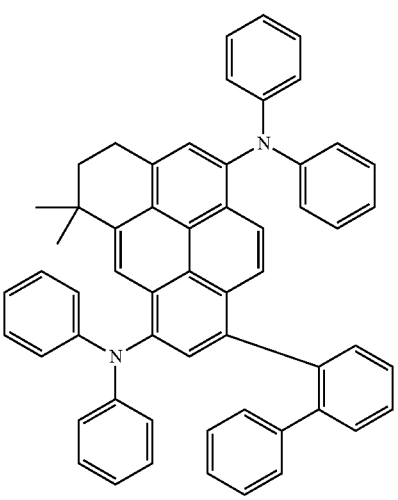

129
-continued
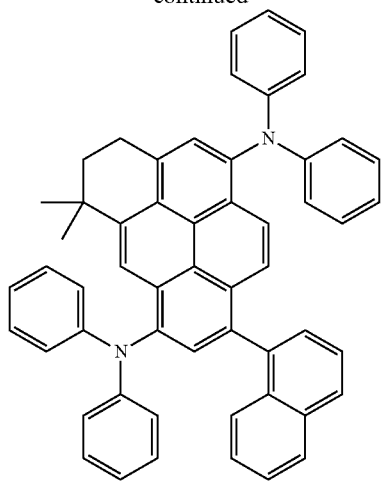
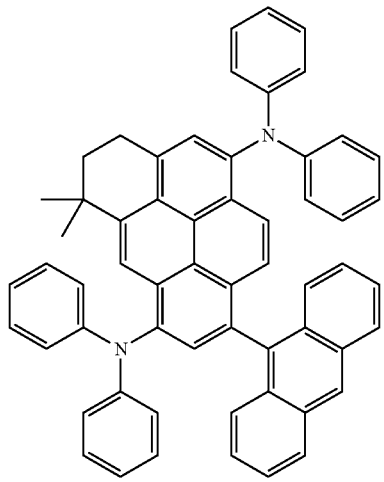
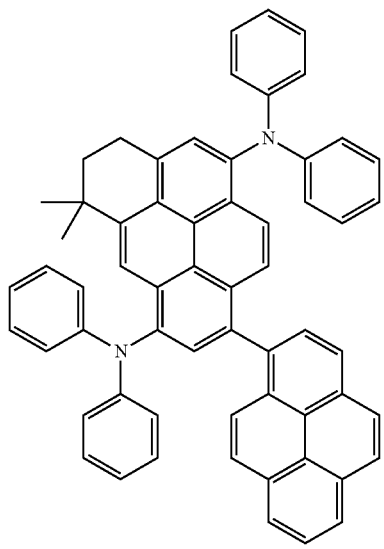
130
-continued
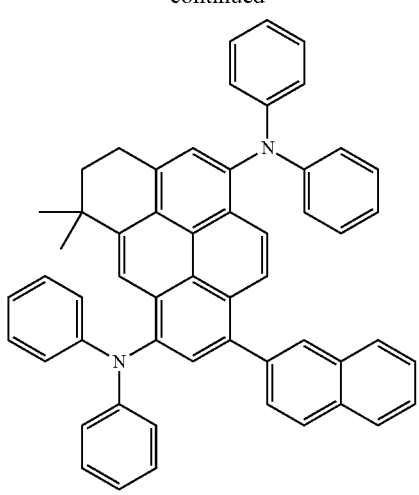
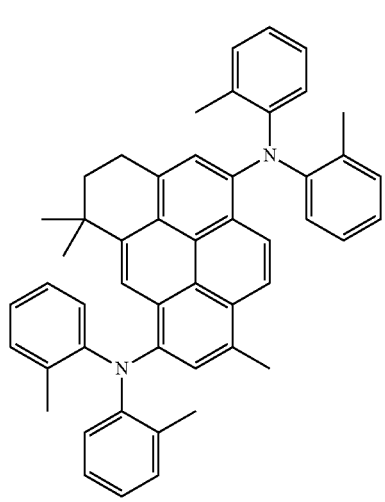
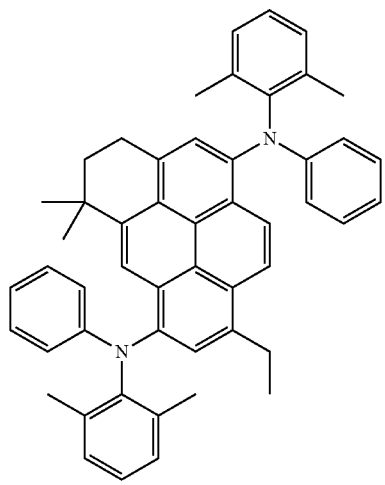

131
-continued
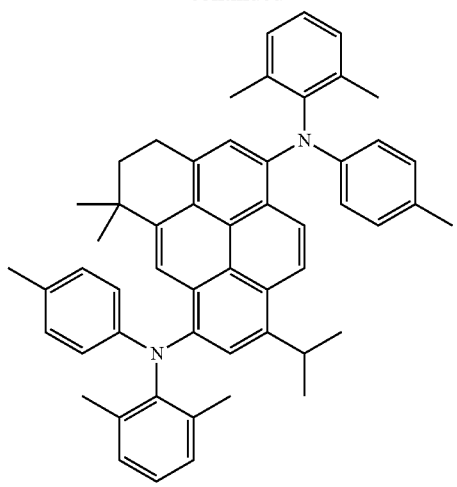
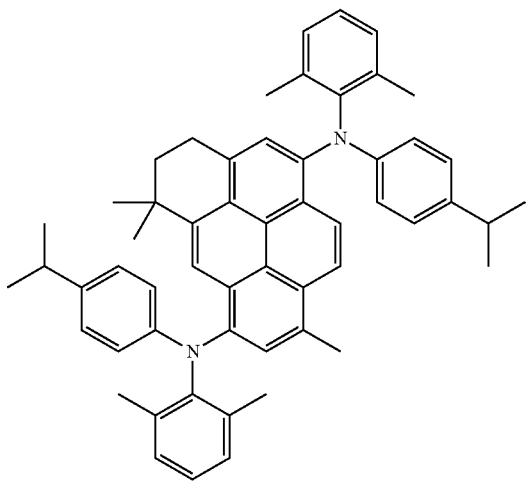
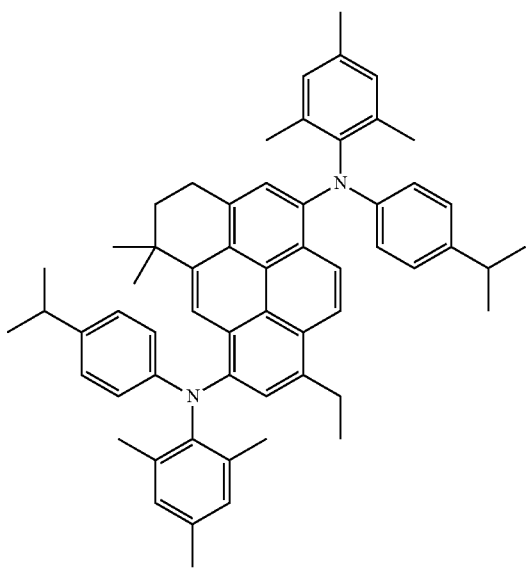
132
-continued
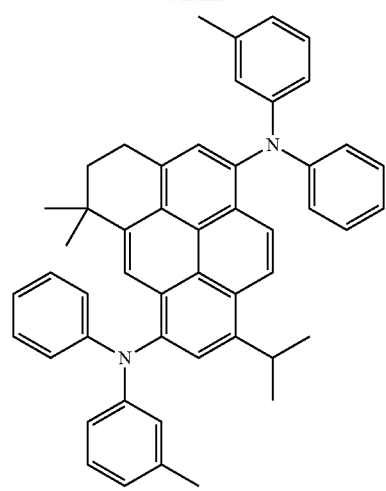
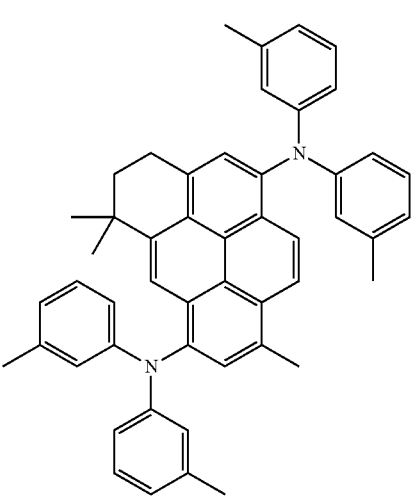
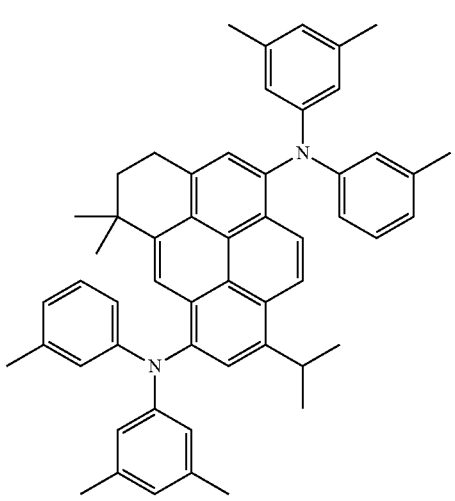

133
-continued
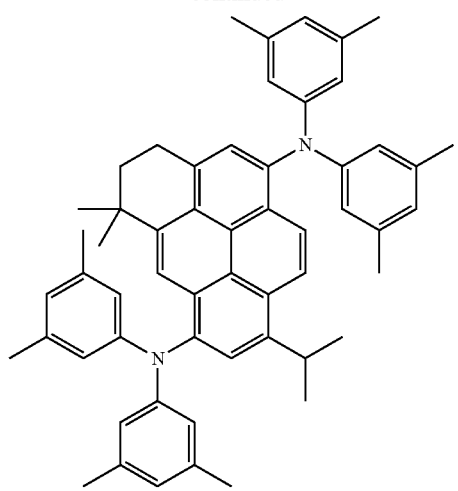
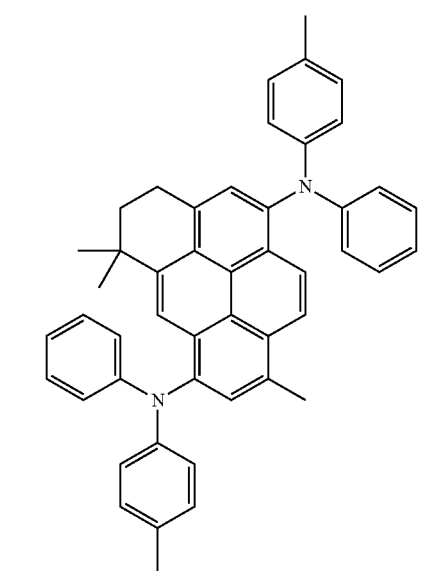
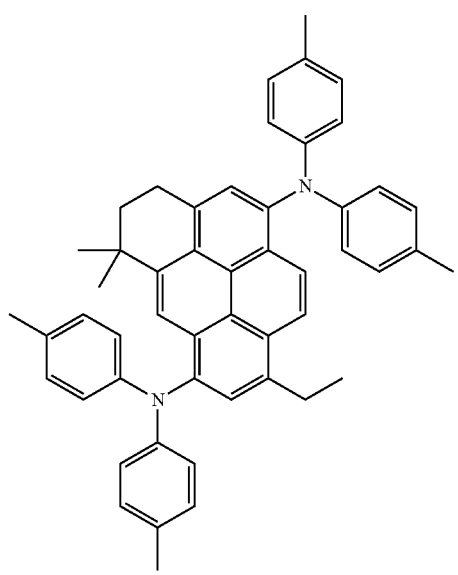
134
-continued
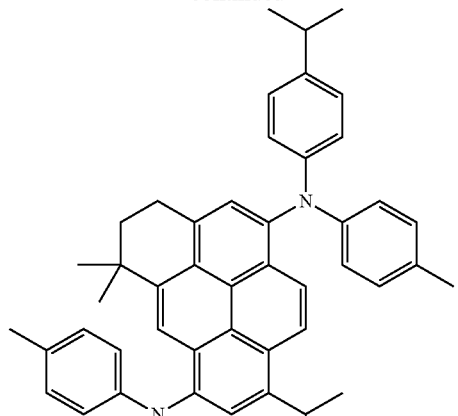
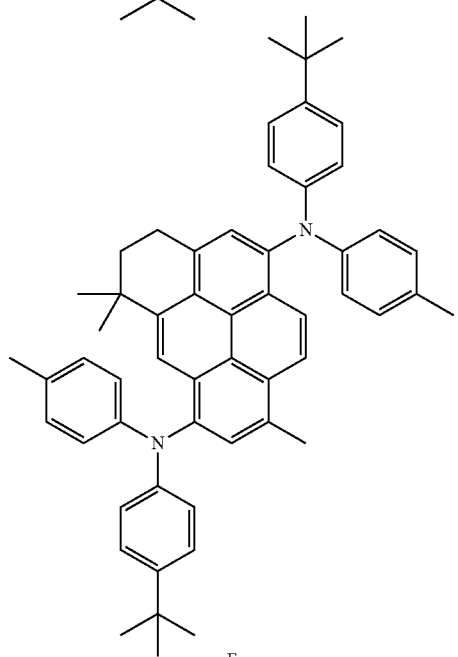
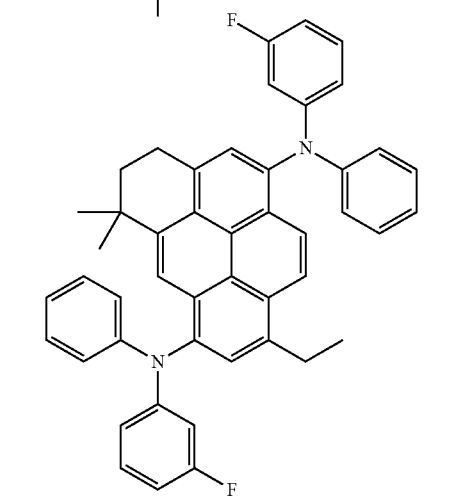

135
-continued
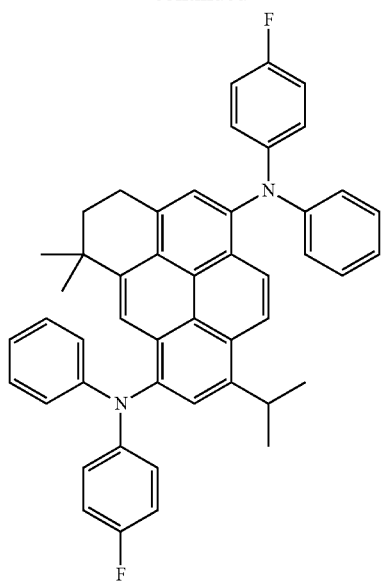
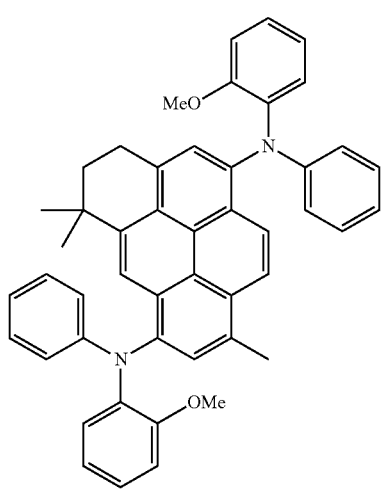
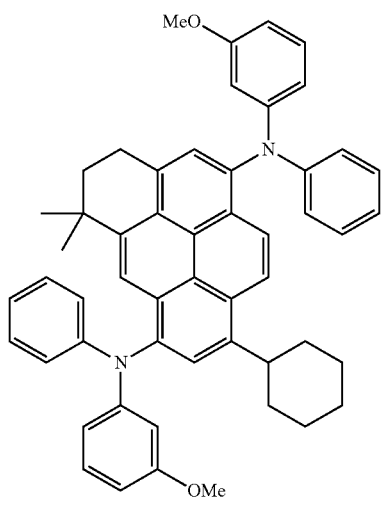
136
-continued
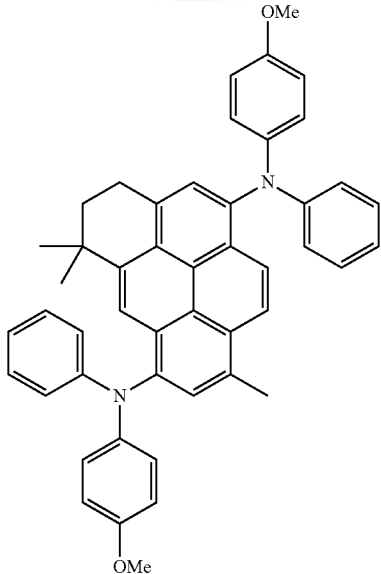
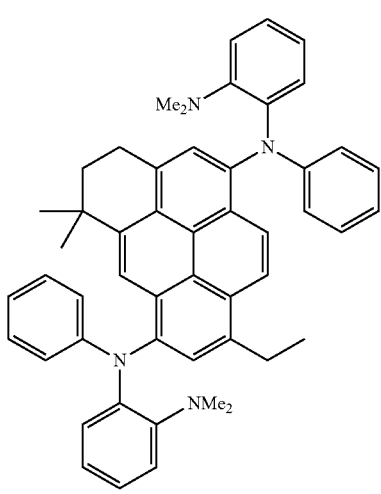
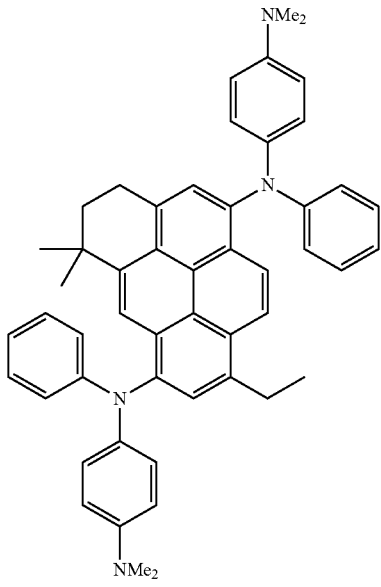

-continued
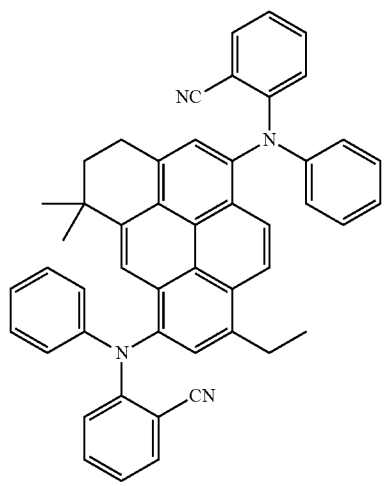
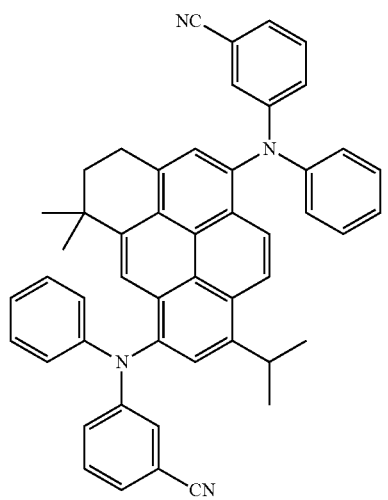
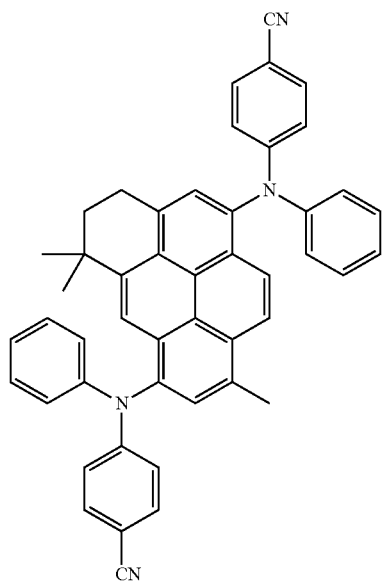
-continued
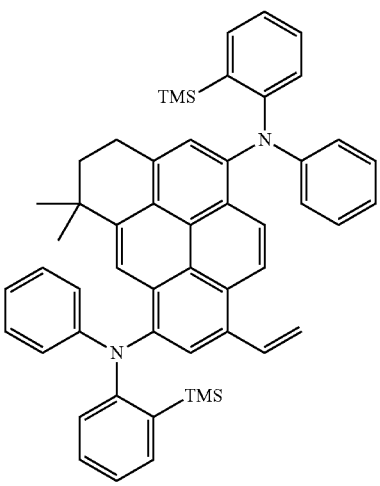
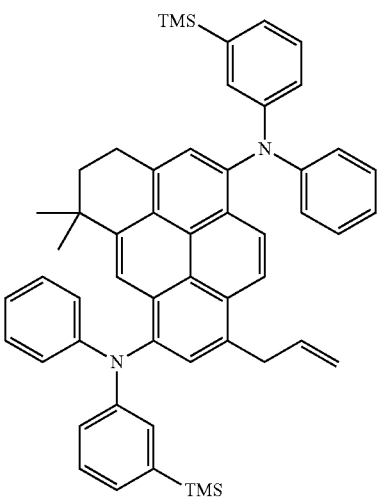
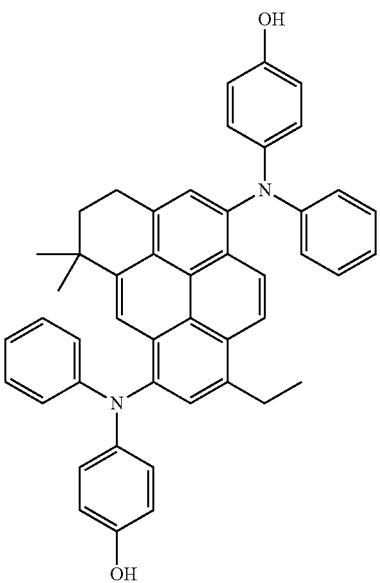

139
-continued
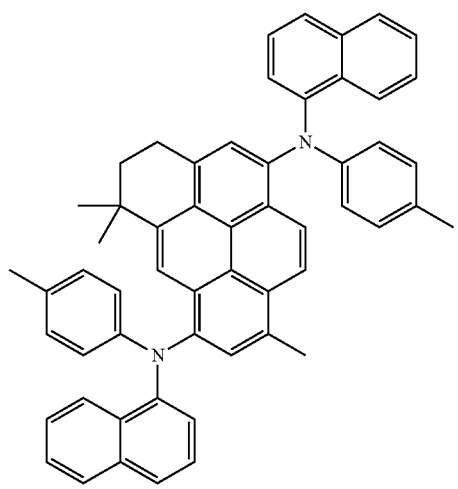
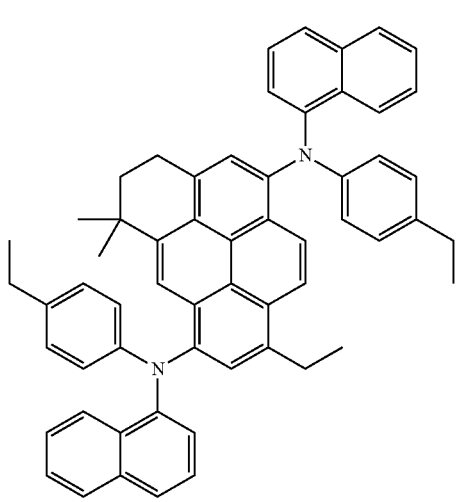
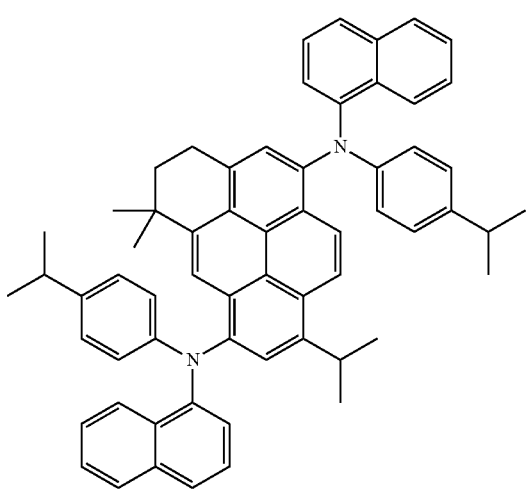
140
-continued
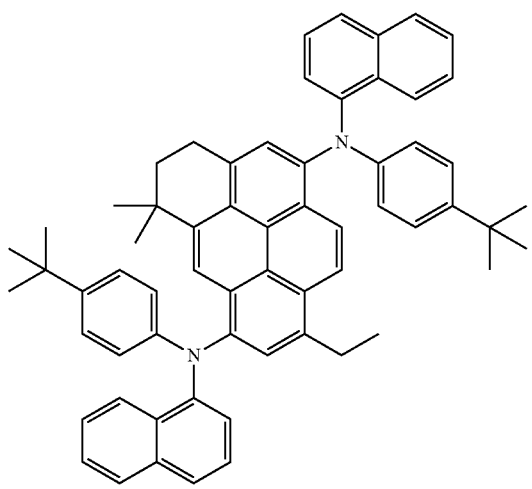
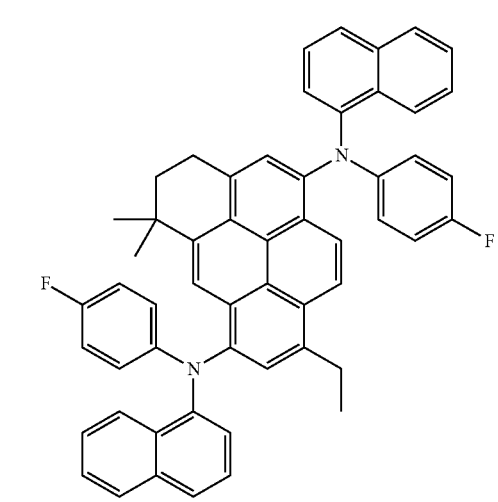
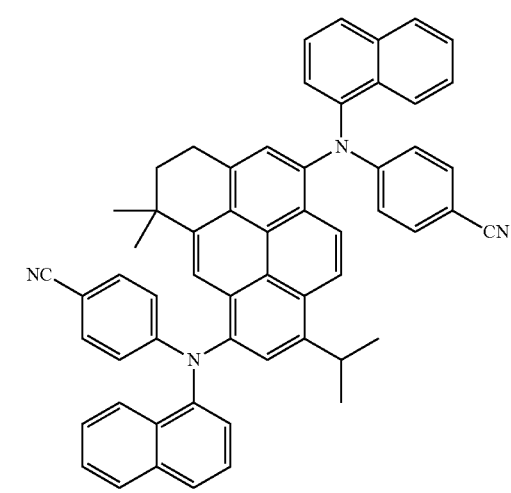

141
-continued
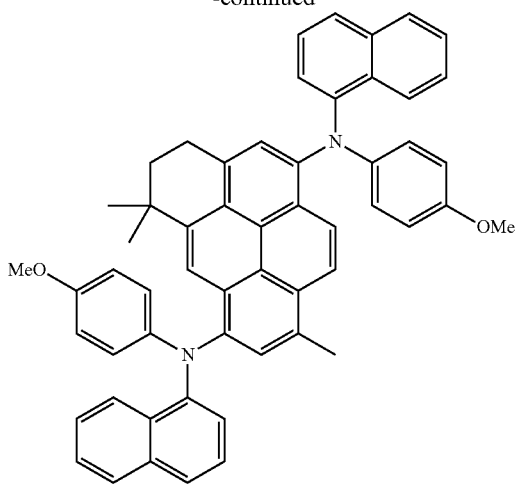
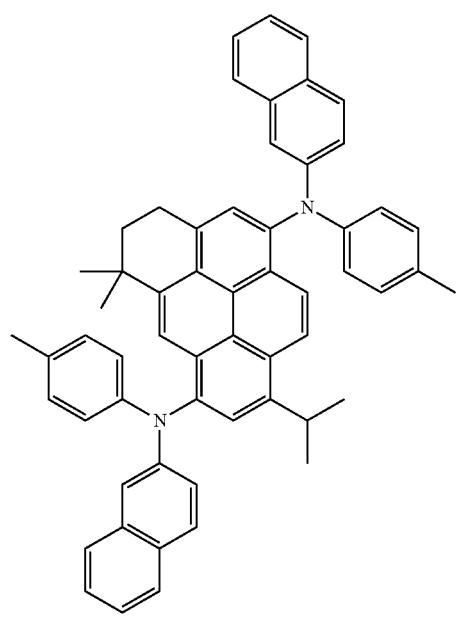
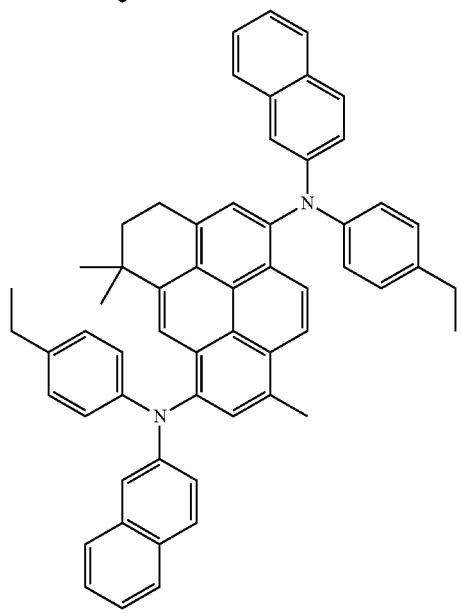
142
-continued
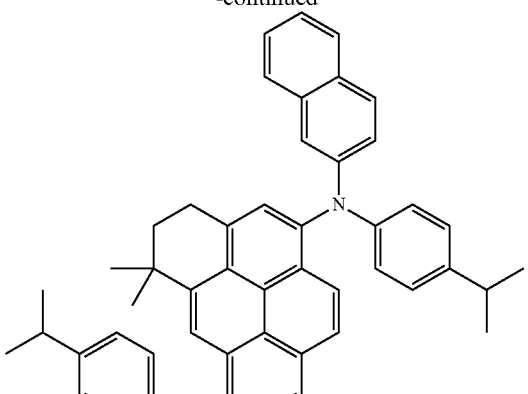
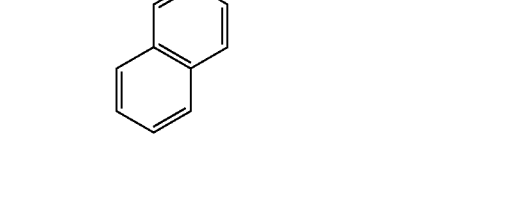

143
-continued
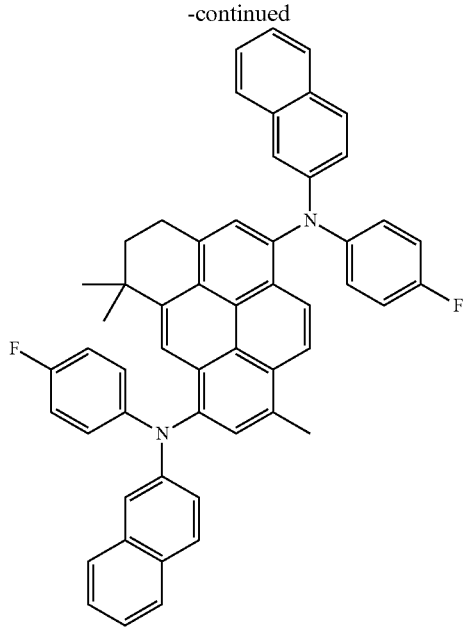
144
-continued
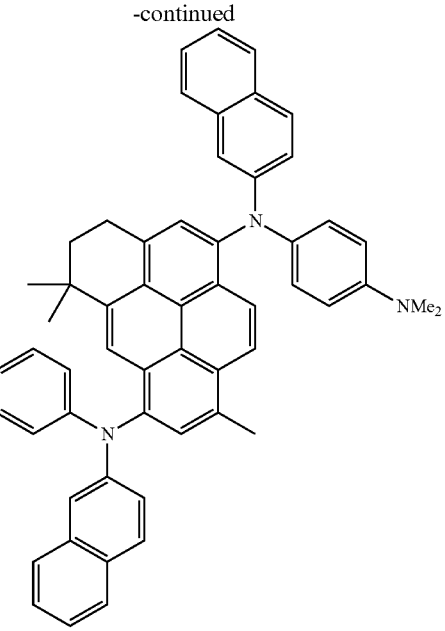
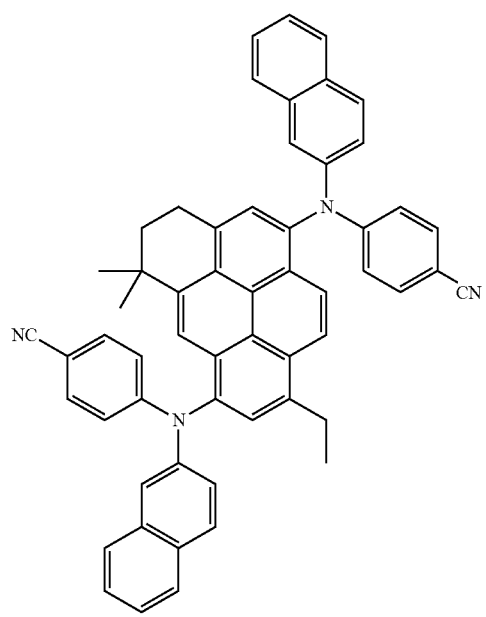
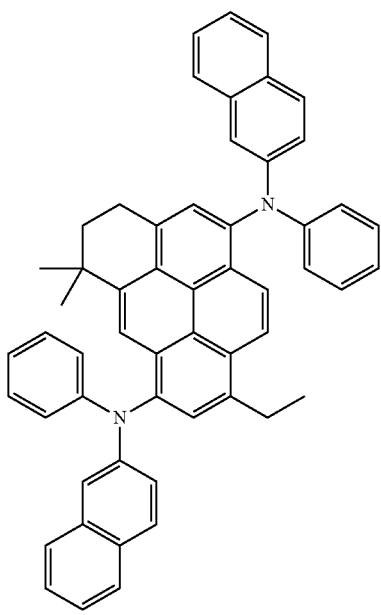

145
-continued
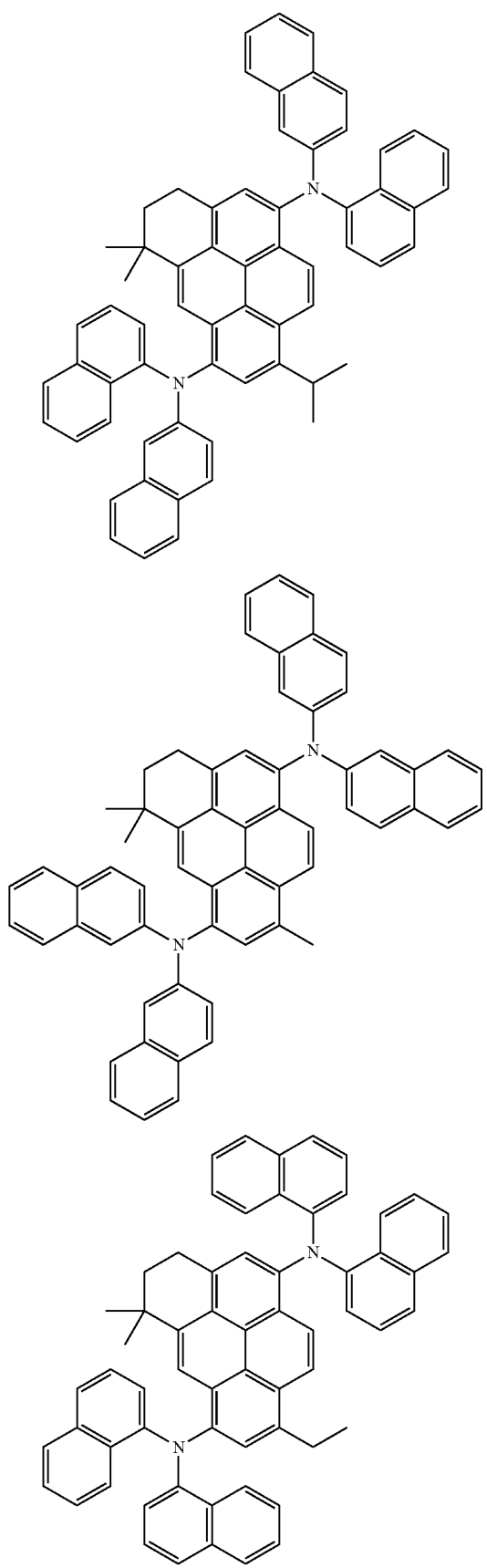
146
-continued
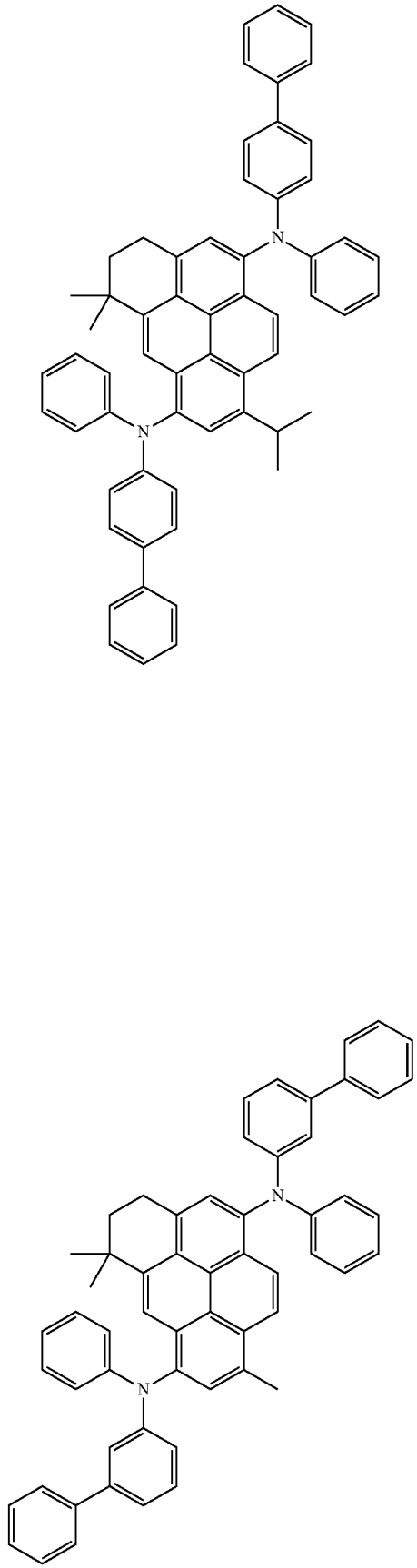

147
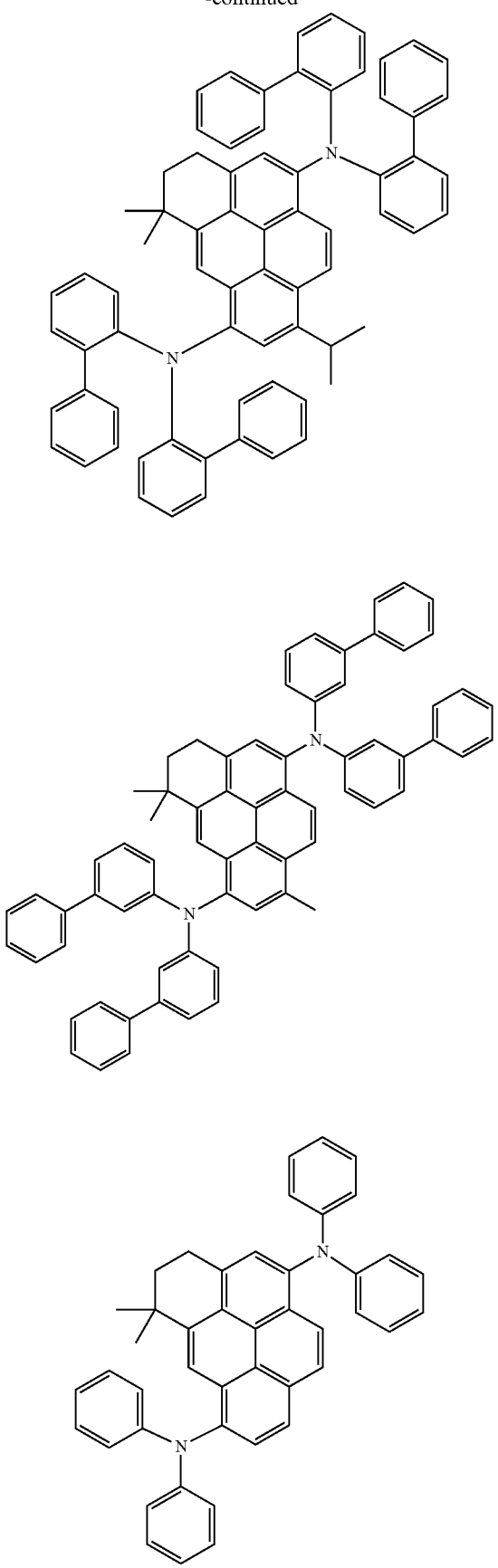
148
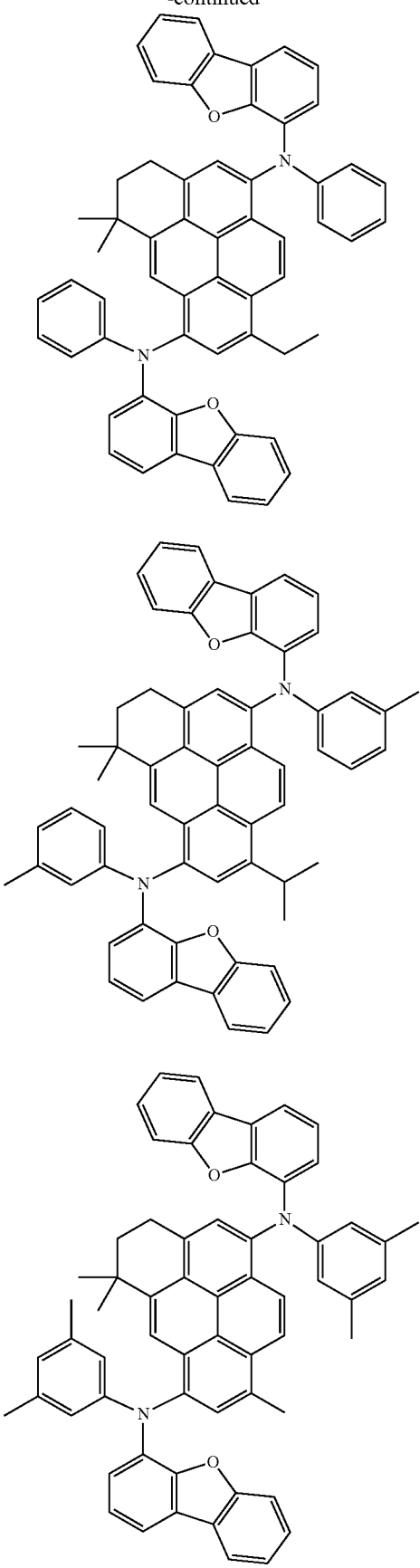

149
-continued
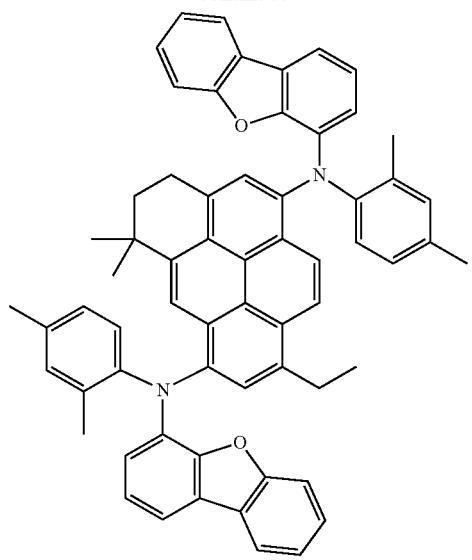
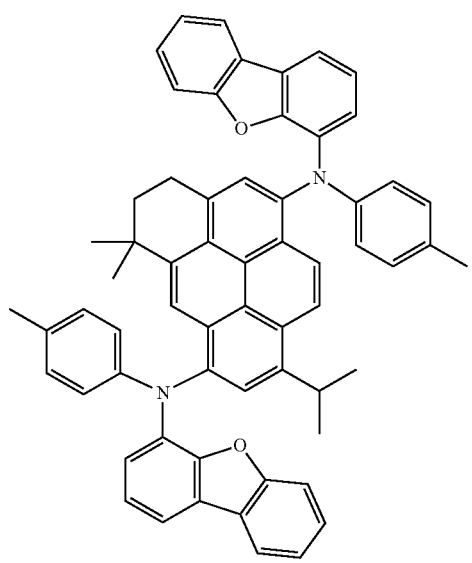
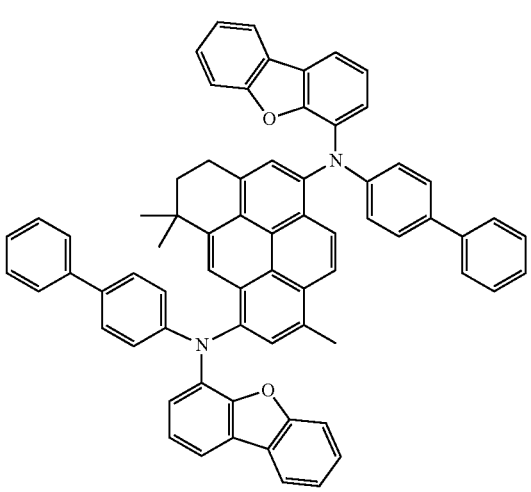
150
-continued
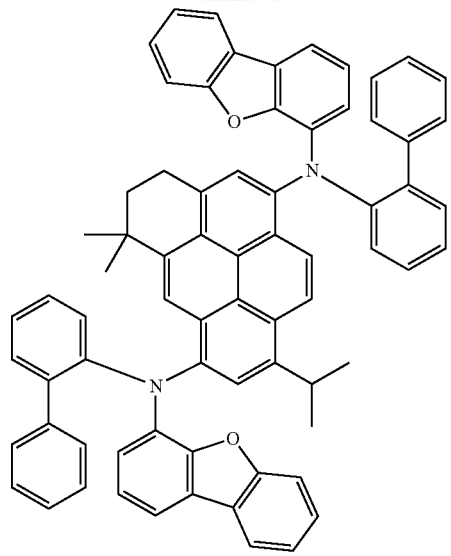
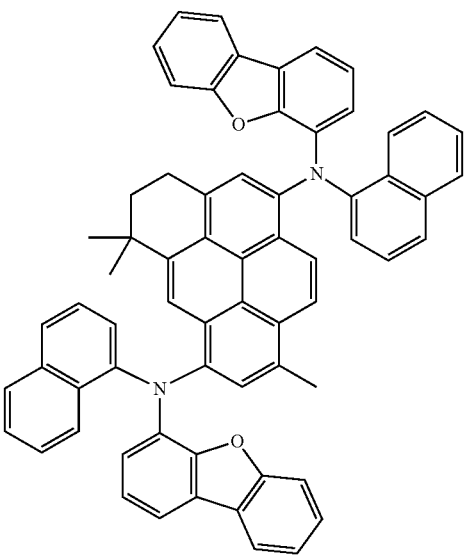
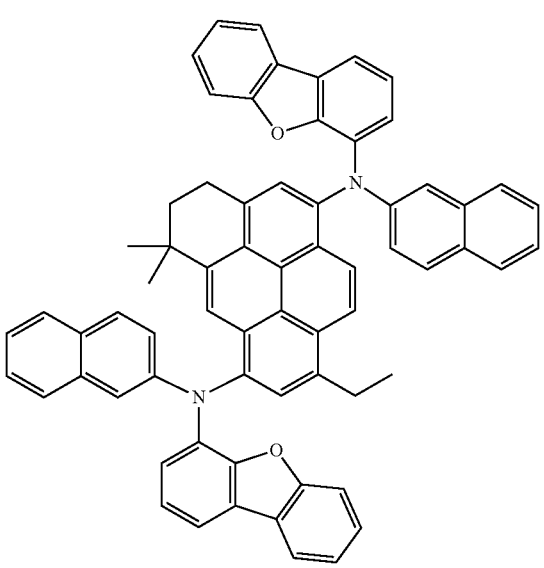

151
-continued
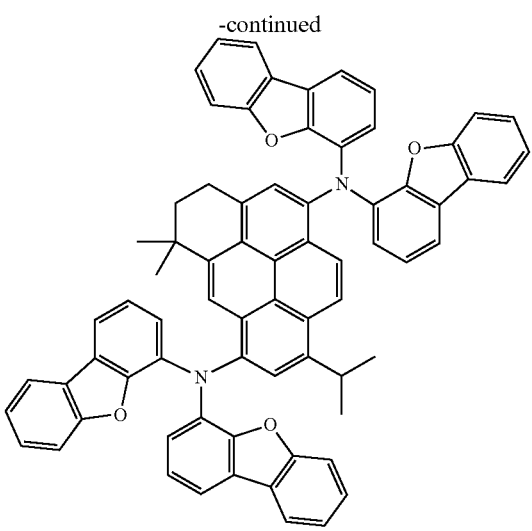
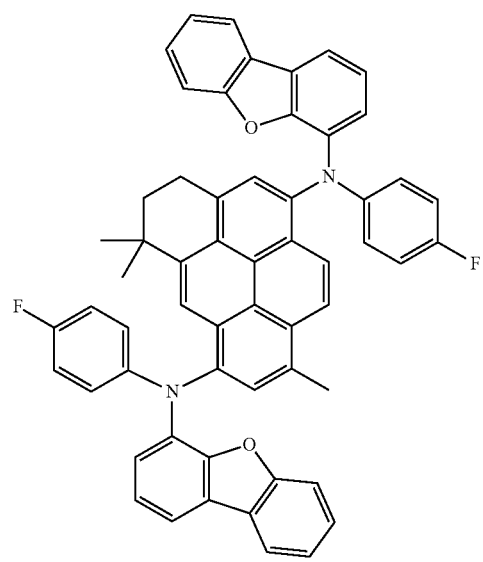
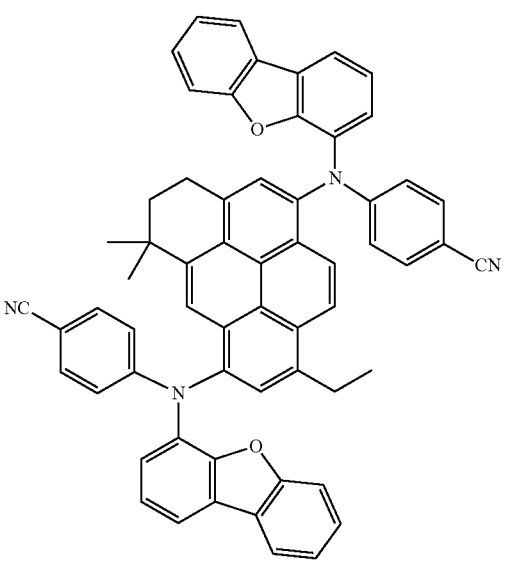
152
-continued
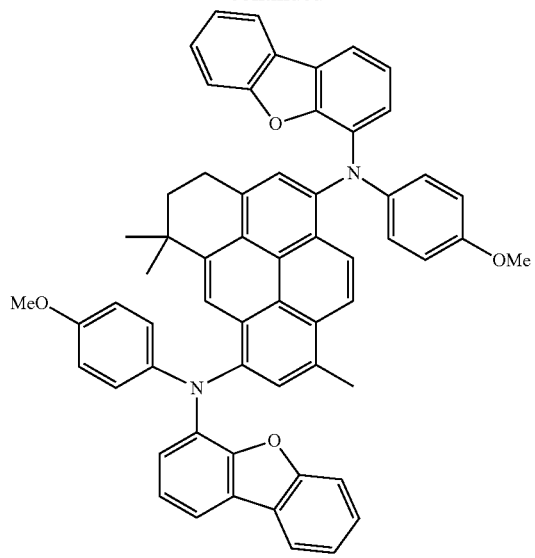
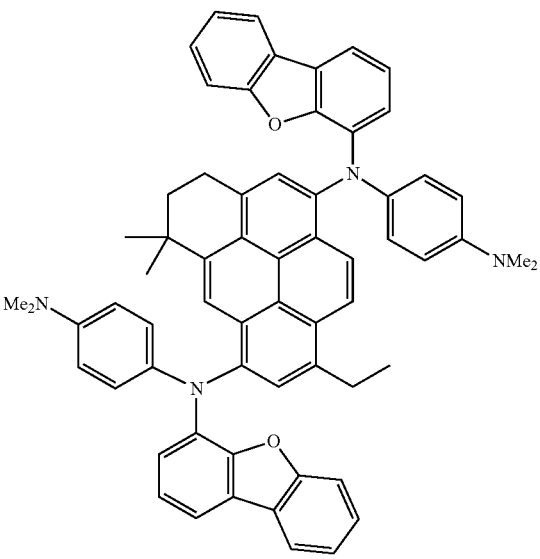
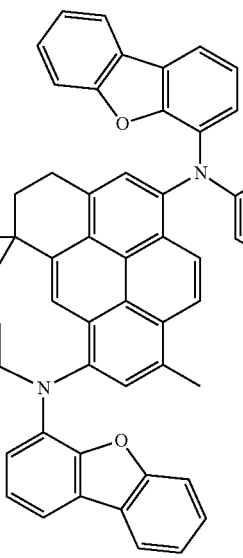

153
-continued
154
-continued
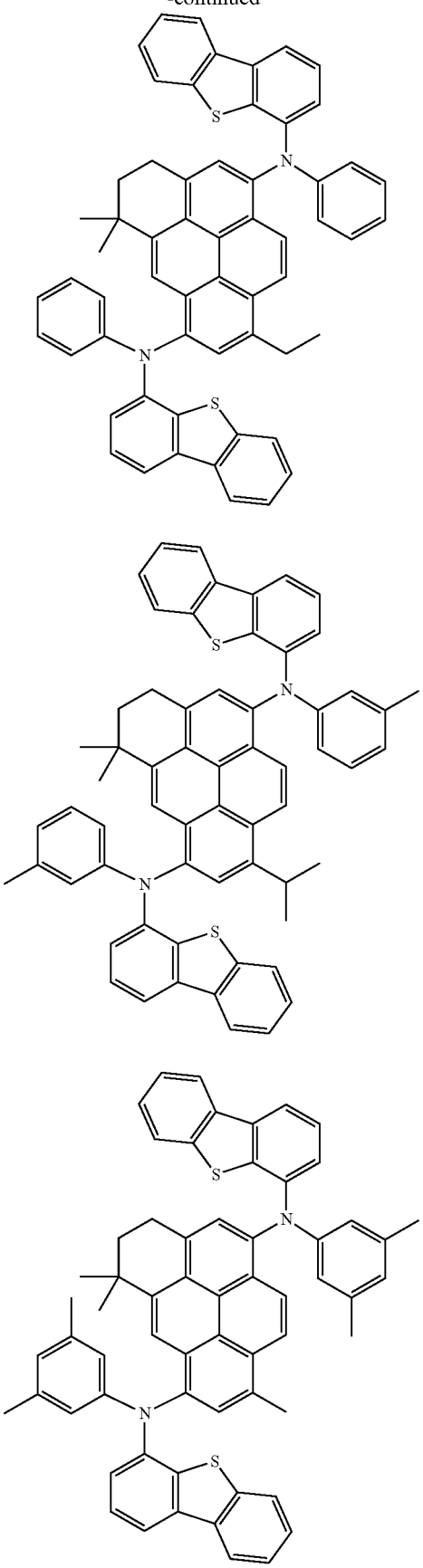
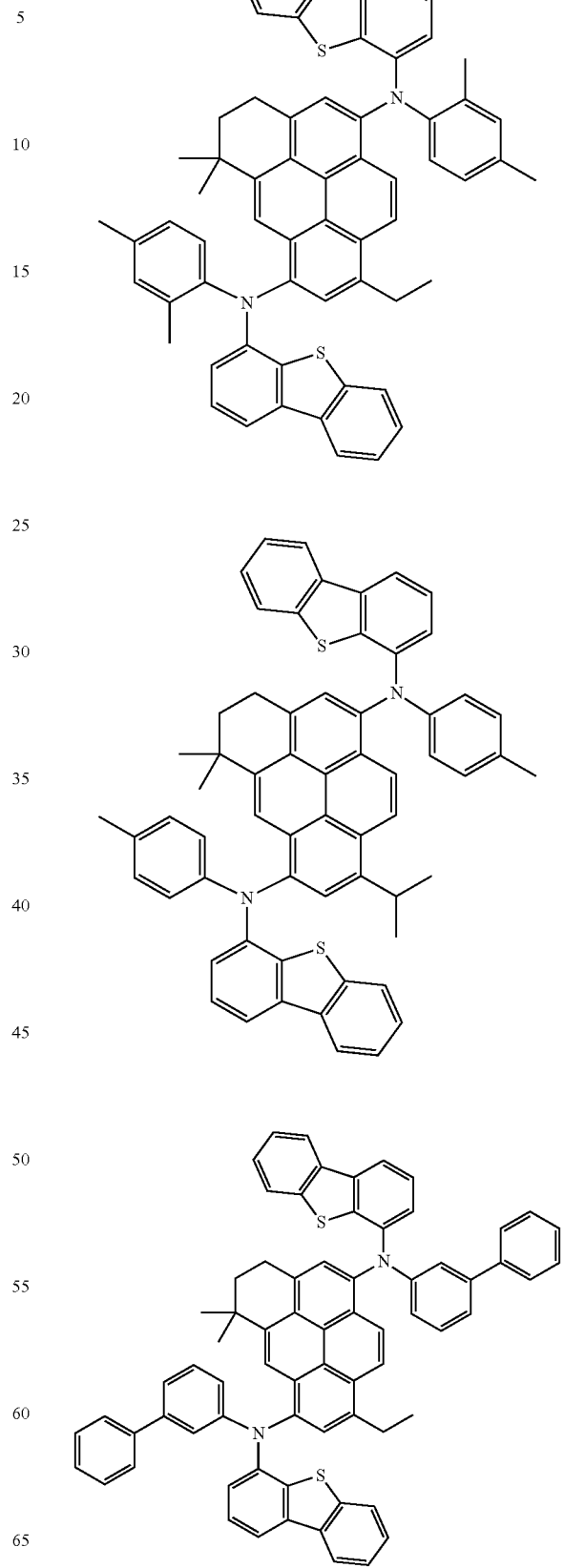

155
-continued
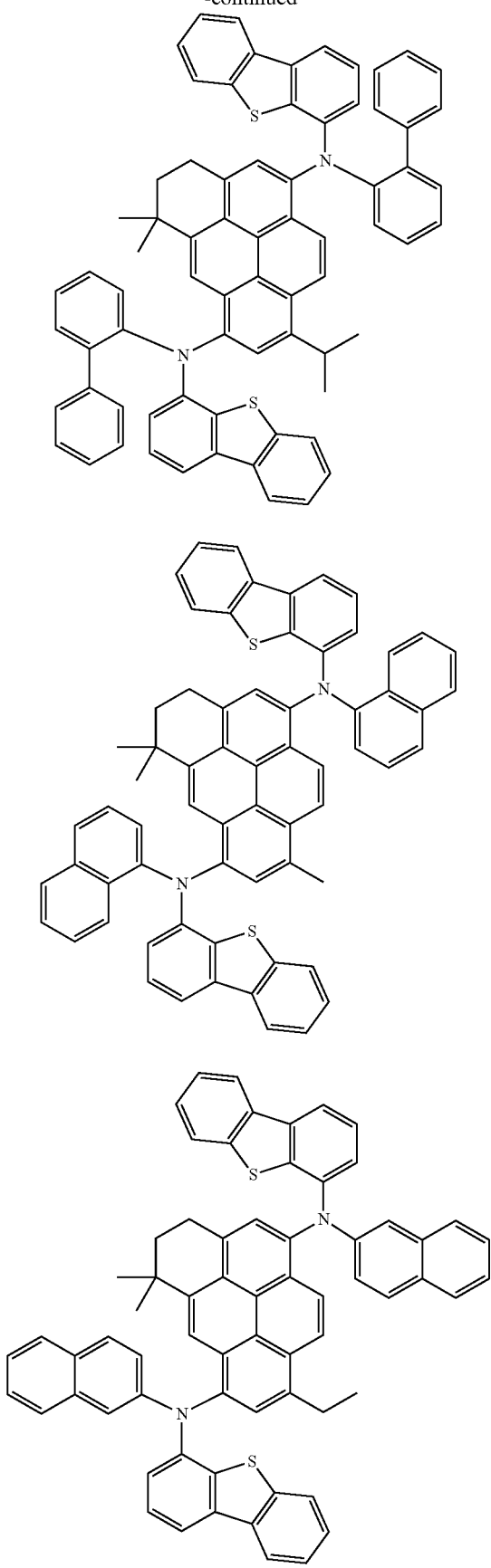
156
-continued
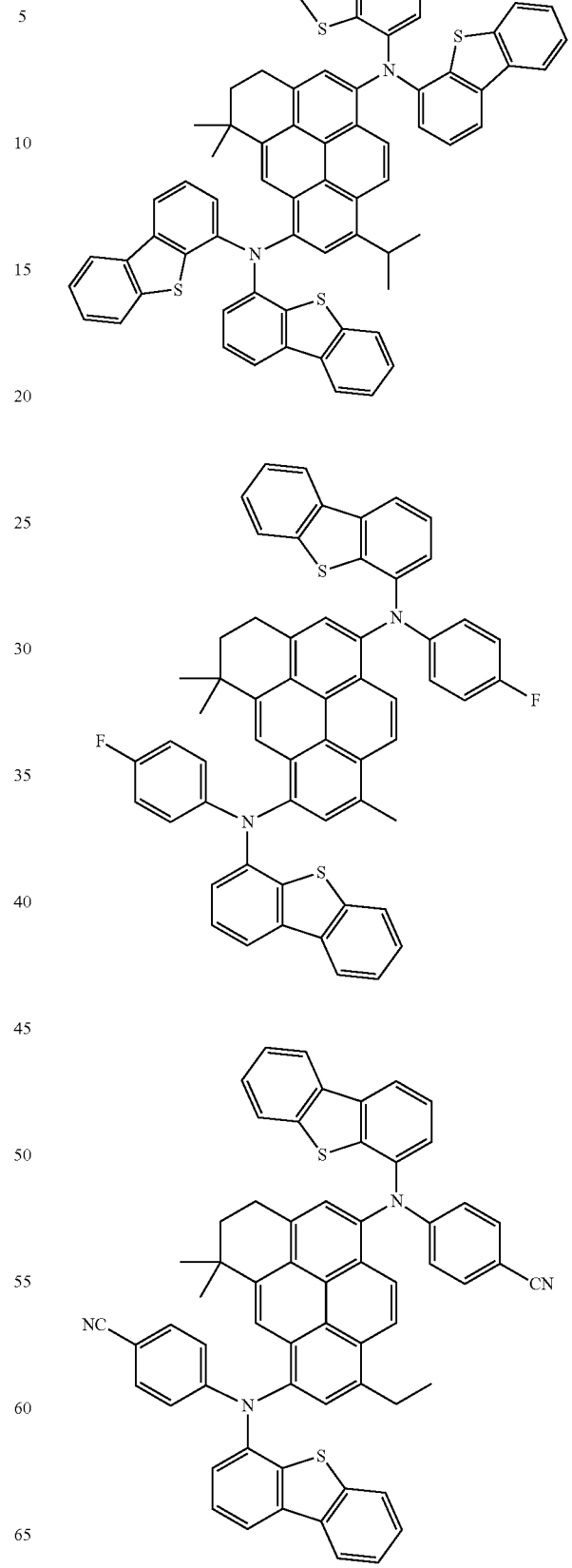

157
-continued
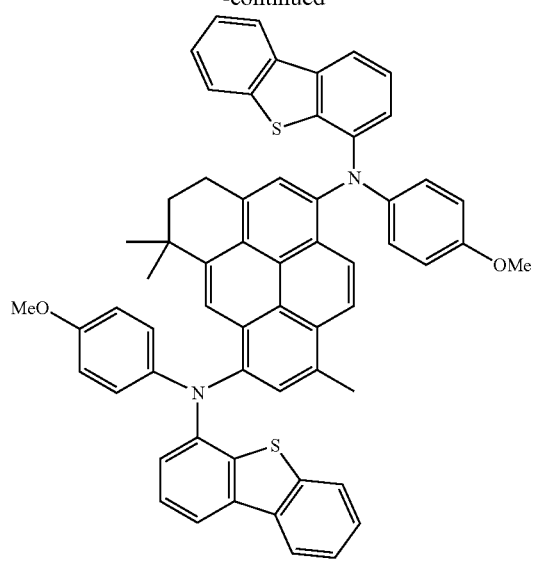
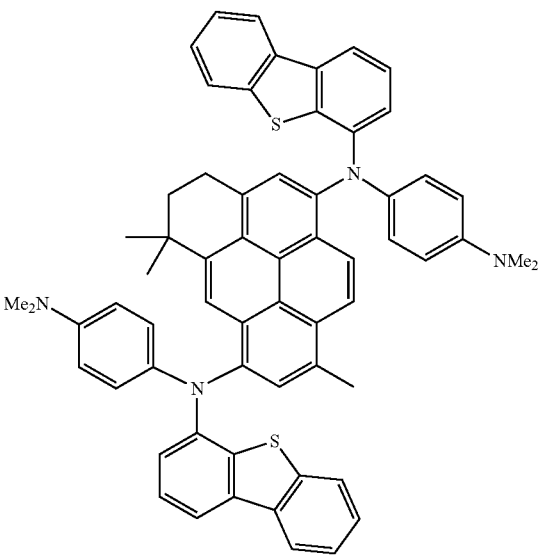
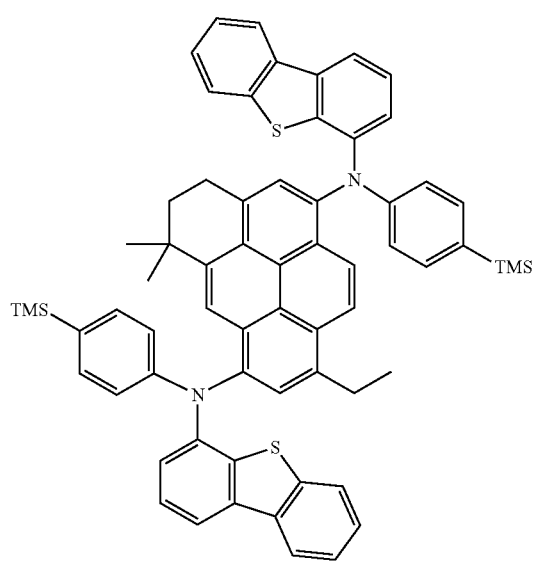
158
-continued
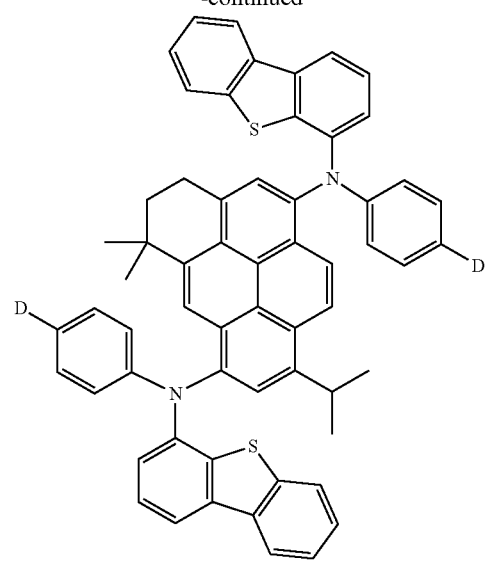
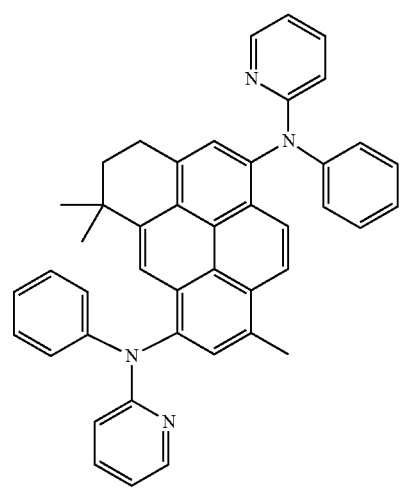
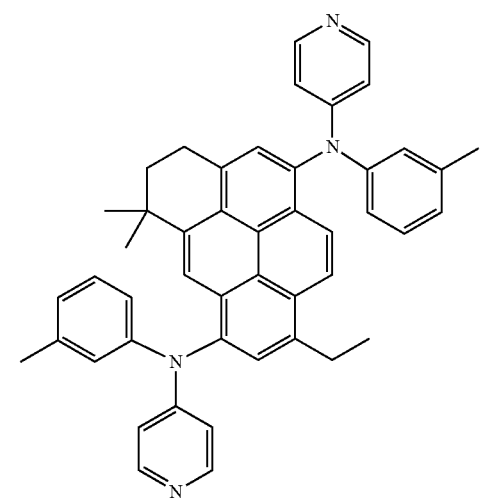

159
-continued
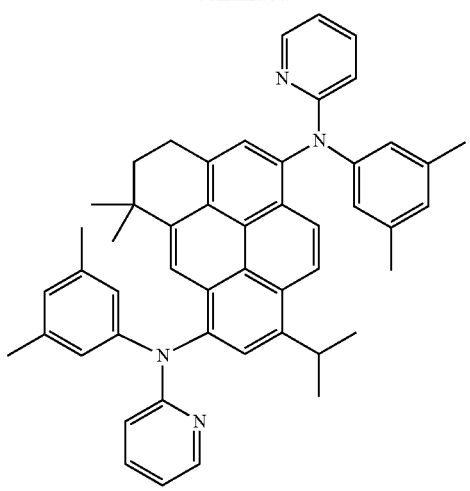
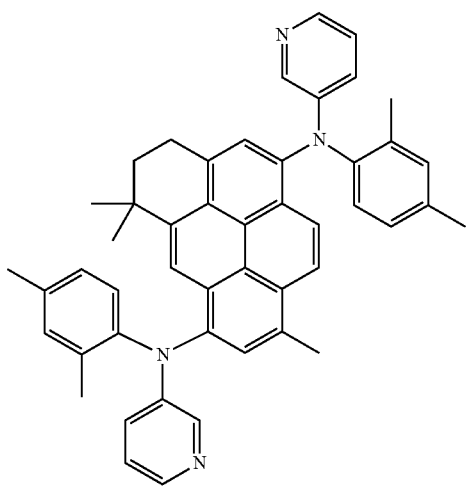
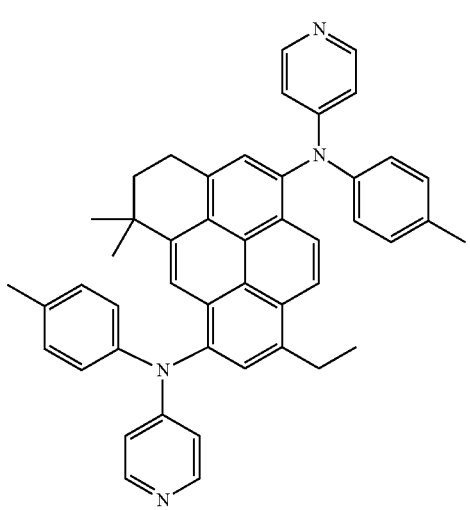
160
-continued
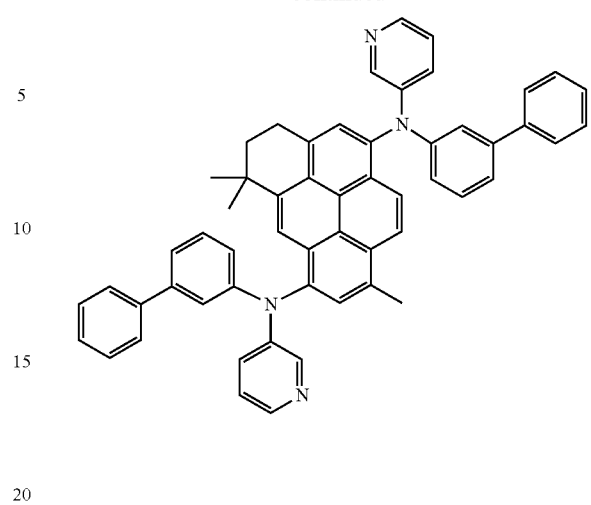
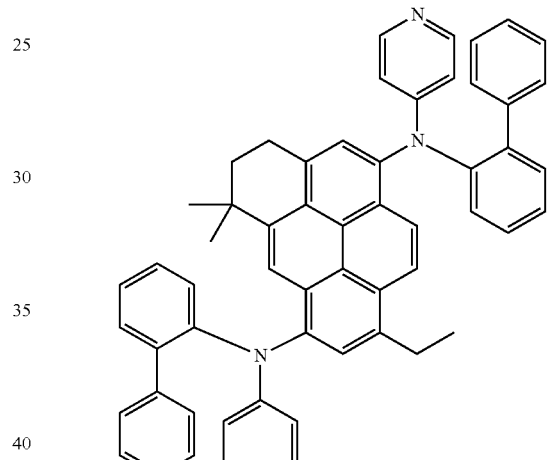
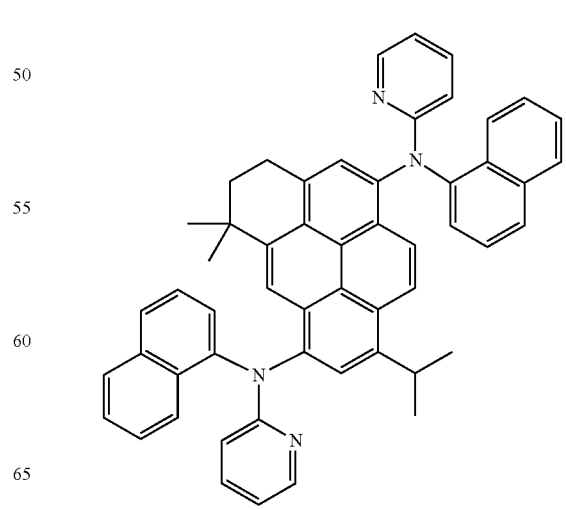

161
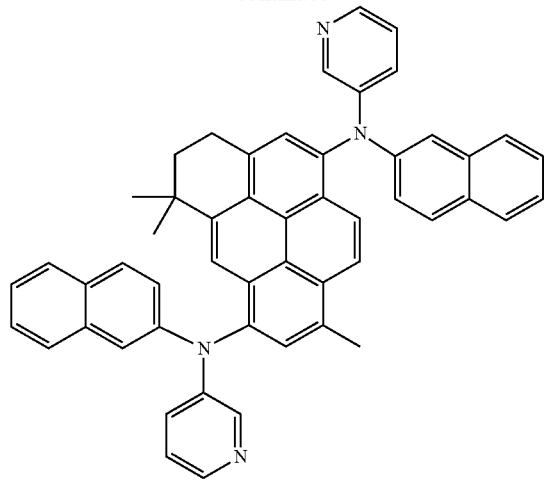
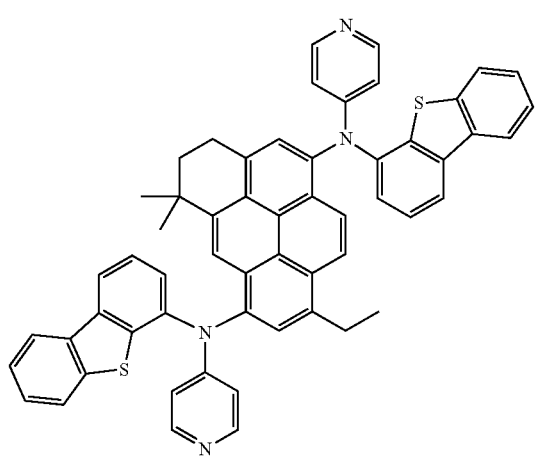
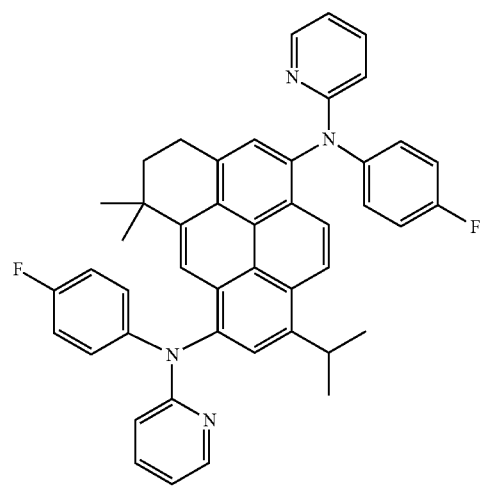
162
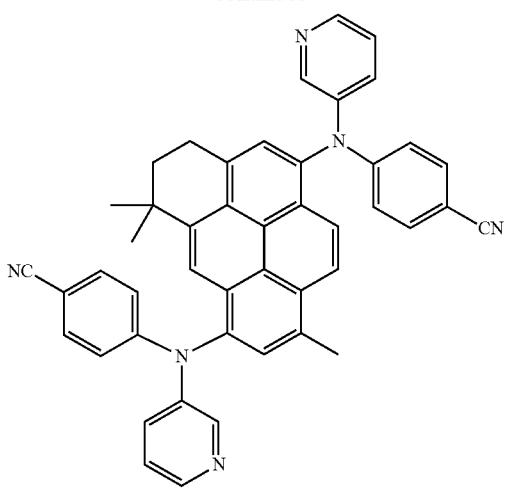
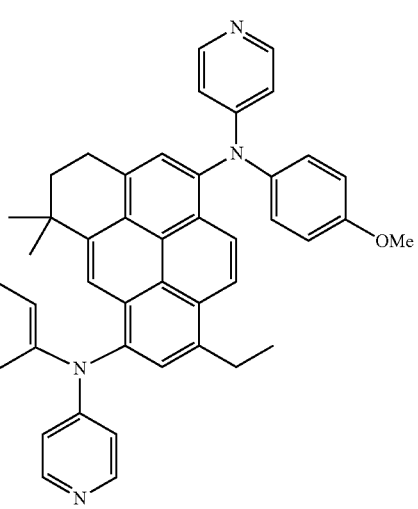
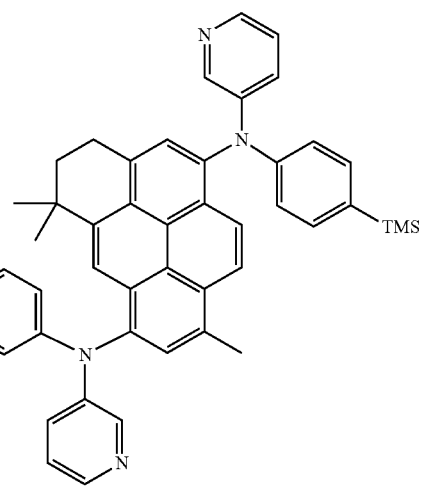

163
-continued
164
-continued
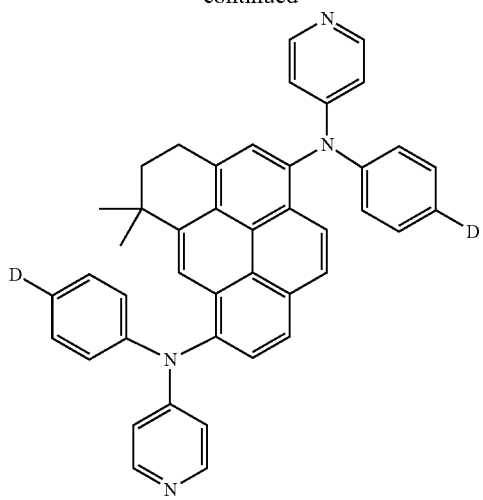
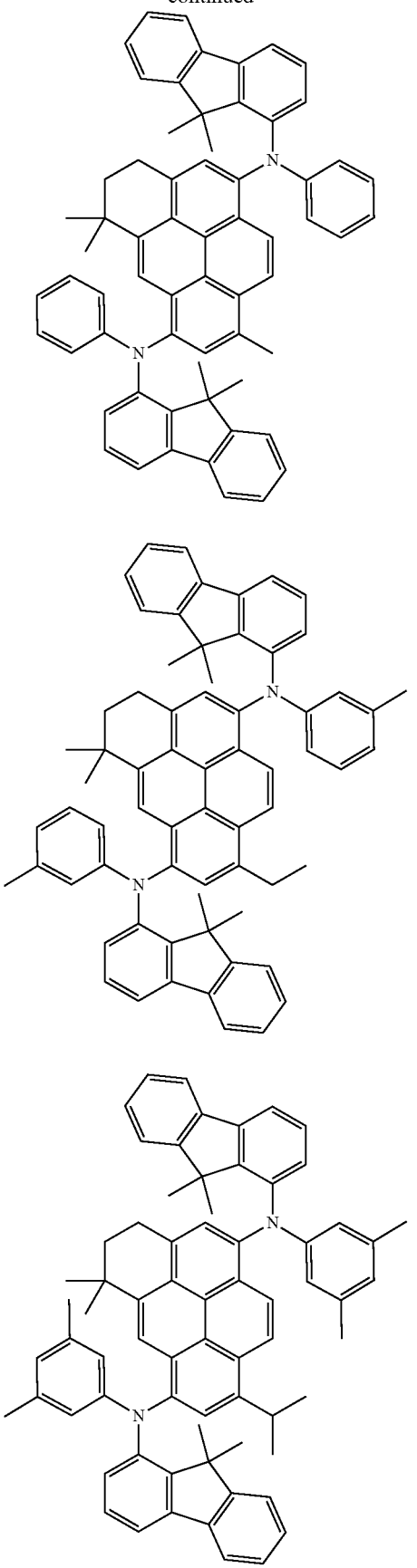
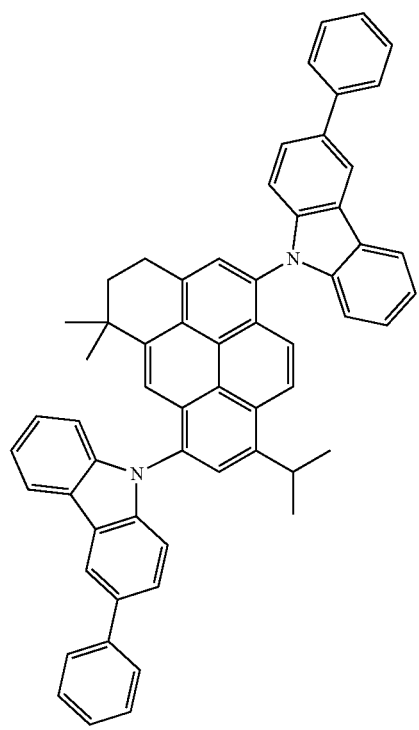

165
-continued
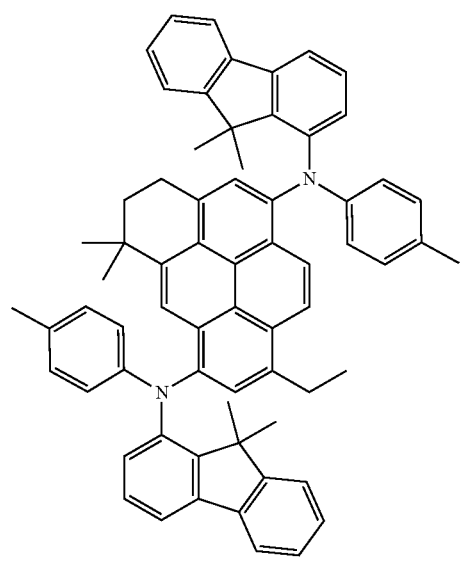
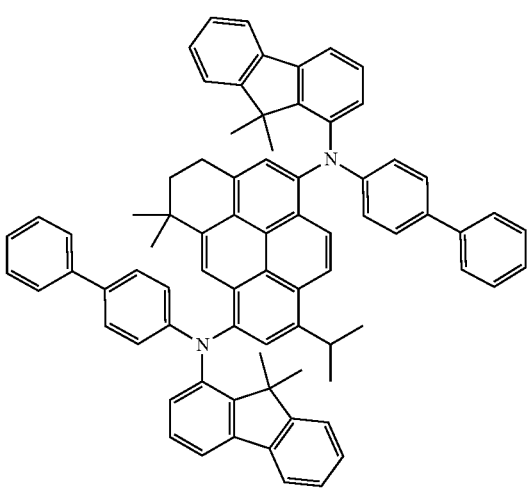
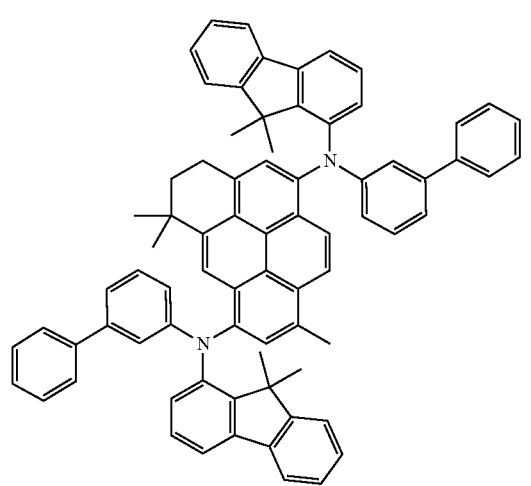
166
-continued
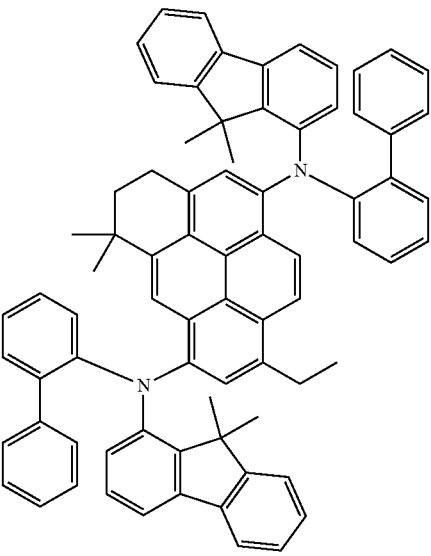
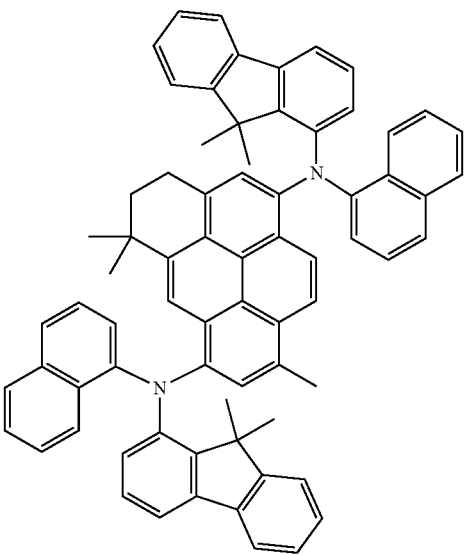
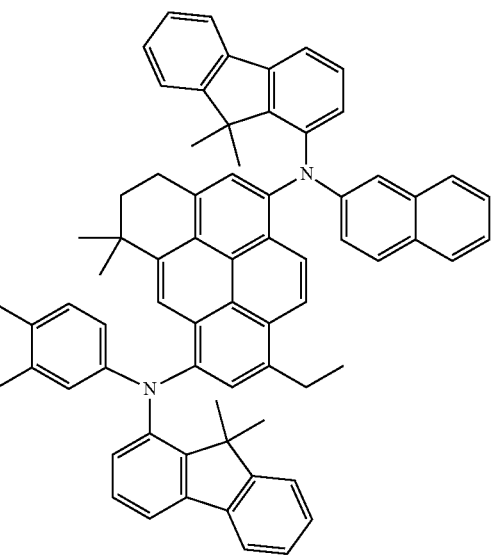

167
-continued
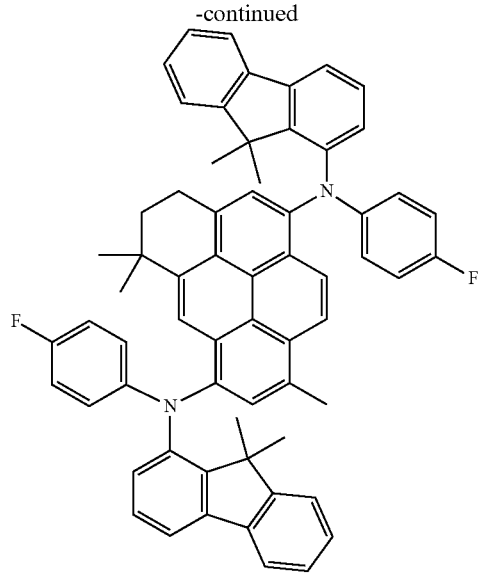
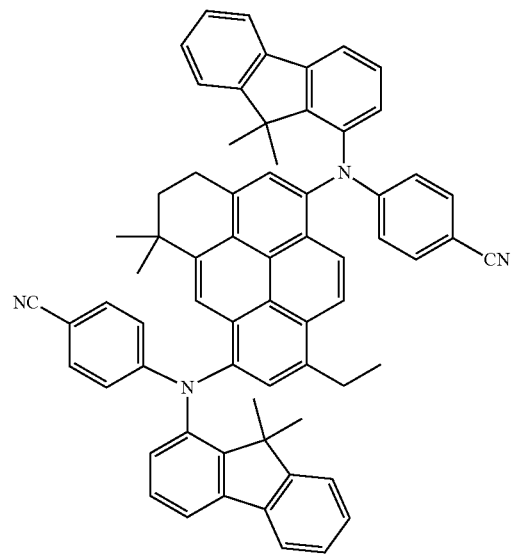
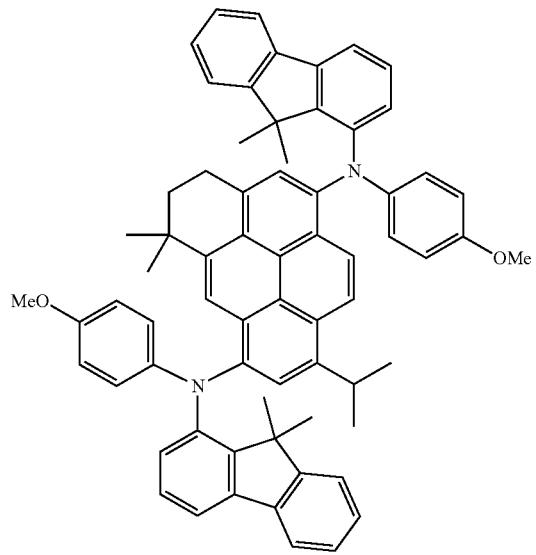
168
-continued
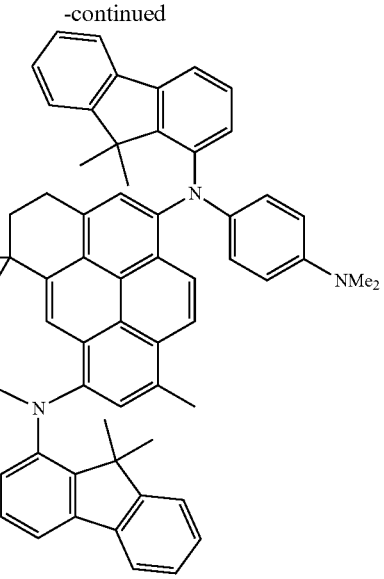
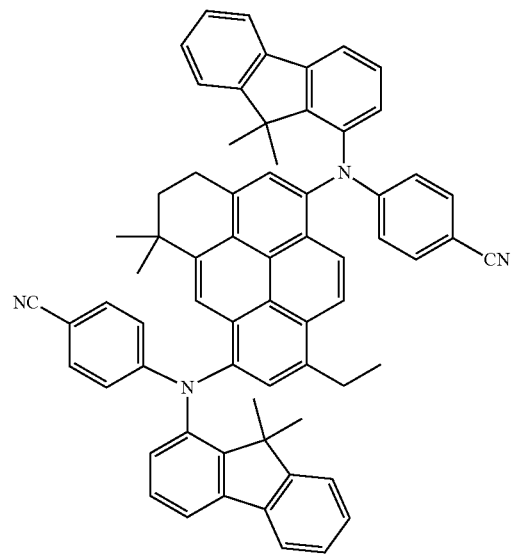
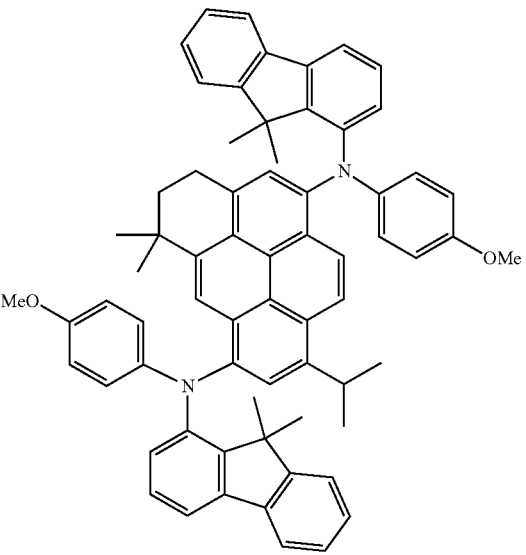

169
-continued
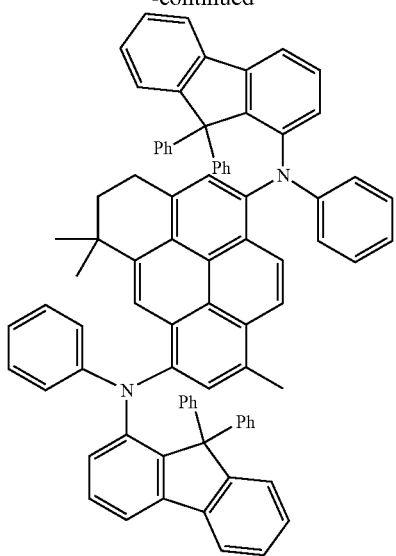
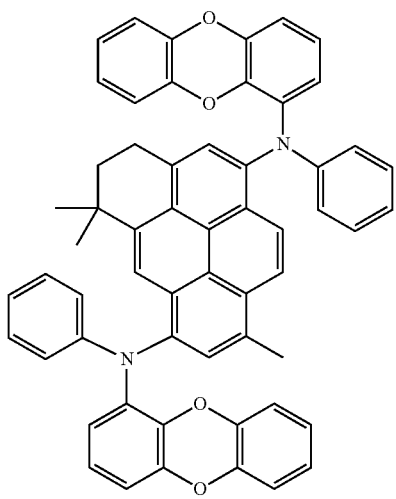
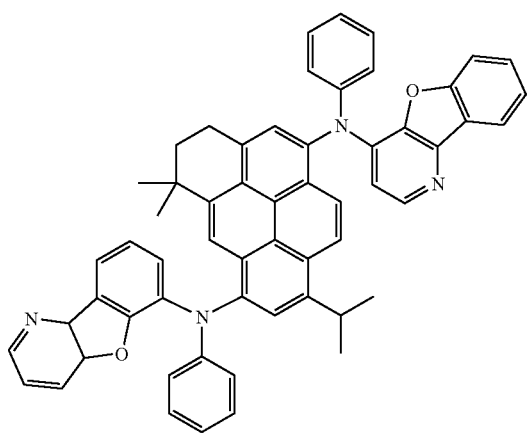
170
-continued
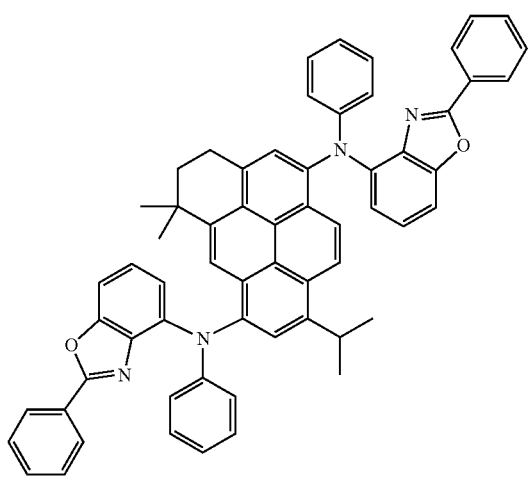
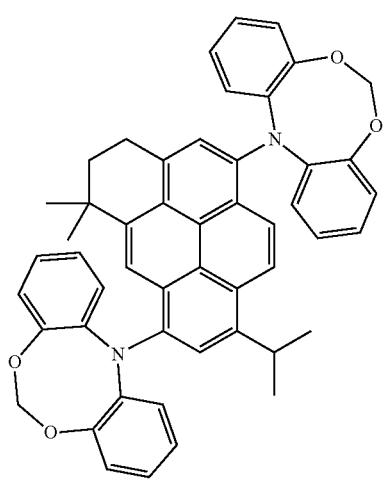
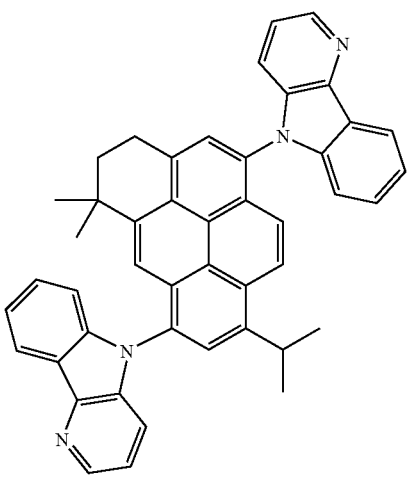

171
-continued
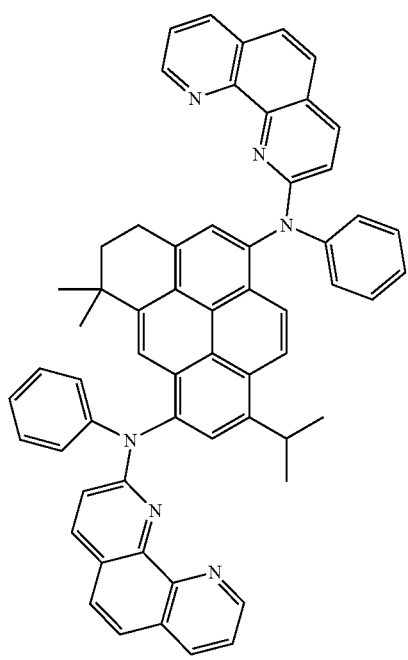
172
-continued
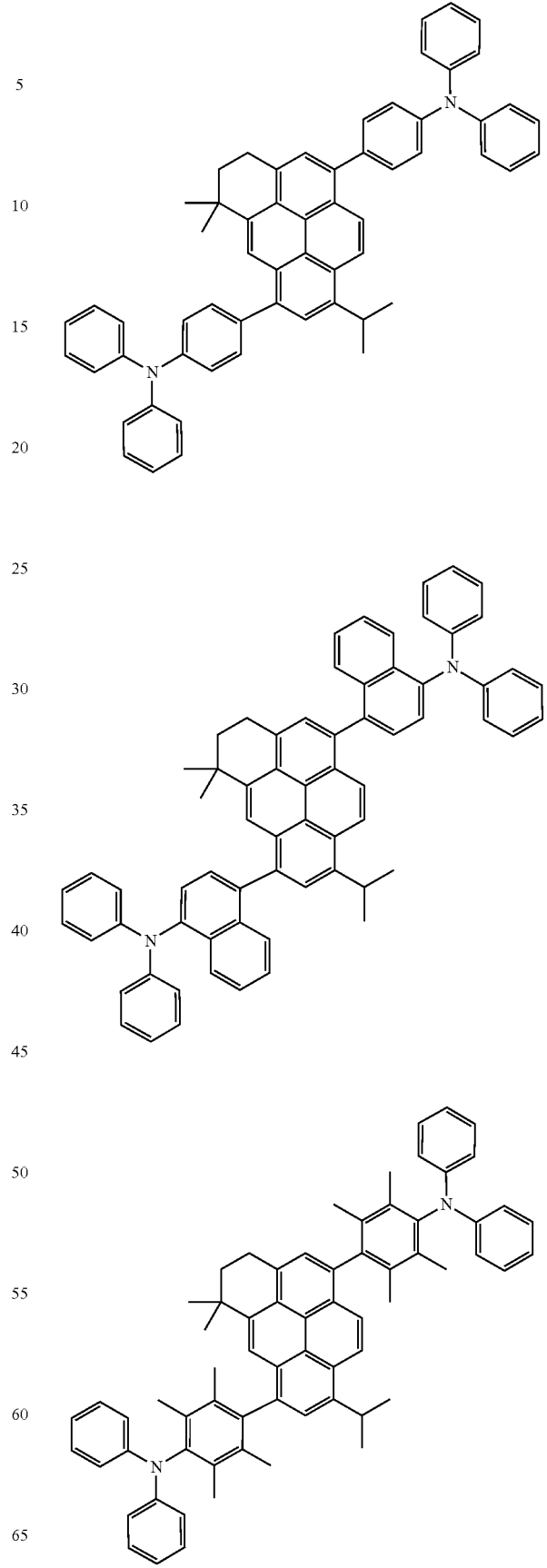
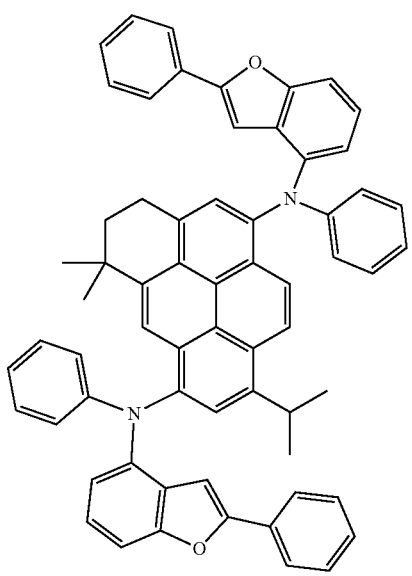

-continued

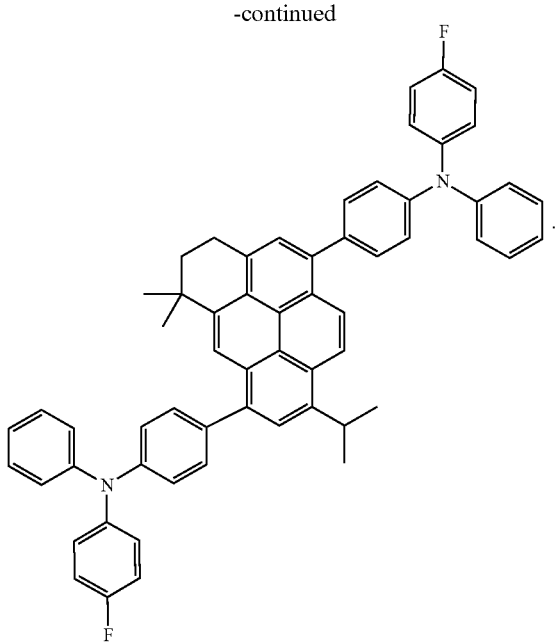

5. An organic light-emitting diode (OLED), comprising:
a first electrode; a second electrode placed opposite to the first electrode; and one or more organic layers interposed between the first electrode and the second electrode,
wherein the one or more organic layers include one or more organic compounds of claim 1.

6. The OLED of claim 5, wherein the organic layer(s) further include(s) one or more selected from an electron injection layer, an electron transport layer, a hole blocking layer, an electron blocking layer, a hole transport layer and a hole injection layer.

7. The OLED of claim 5, wherein the organic layer includes a light emitting layer.

8. The OLED of claim 7, wherein the light emitting layer includes:
one or more hosts selected from the group consisting of naphthalene, anthracene, pyrene, phenanthrene, fluoranthene, chrysene, perylene, naphthacene and pentacene; and one or more of organic compounds represented by Formula 2 below as a dopant:

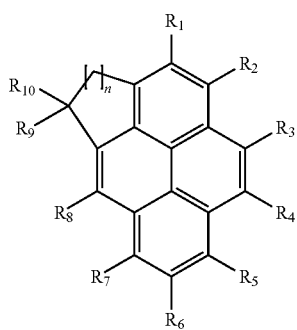

[Formula 2]

wherein n is an integer of 2 forming a saturated ring having 6 carbon atoms, and $R_1$ to $R_8$ are the same or different, and each independently selected from the group consisting of hydrogen, deuterium, a halogen, a nitro group, a cyano group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted cycloalkyl group having 3 to 30 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 6 to 30 carbon atoms, a substituted or unsubstituted heteroarylalkyl group having 6 to 30 carbon atoms, a substituted or unsubstituted alkylsilyl group having 1 to 30 carbon atoms, a substituted or unsubstituted arylsilyl group having 6 to 30 carbon atoms and a substituted or unsubstituted aryloxy group having 6 to 30 carbon atoms, and the substituents of $R_1$ to $R_8$ may be the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms, a heteroalkyl group having 2 to 30 carbon atoms, an aralkyl group having 7 to 30 carbon atoms, an aryl group having 6 to 30 carbon atoms, a heteroaryl group having 2 to 30 carbon atoms, a heteroarylalkyl group having 3 to 30 carbon atoms, an alkoxy group having 1 to 30 carbon atoms, an alkylamino group having 1 to 30 carbon atoms, an arylamino group having 6 to 30 carbon atoms, an aralkylamino group having 6 to 30 carbon atoms, a heteroarylamino group having 2 to 24 carbon atoms, an alkylsilyl group having 1 to 30 carbon atoms, an arylsilyl group having 6 to 30 carbon atoms and an aryloxy group having 6 to 30 carbon atoms, and
$R_9$ and $R_{10}$ are the same or different, and each independently selected from the group consisting of hydrogen, a substituted or unsubstituted alkyl group having 1 to 10 carbon atoms, a substituted or unsubstituted cycloalkyl group having 3 to 12 carbon atoms, a substituted or unsubstituted alkoxy group having 1 to 10 carbon atoms, a halogen, a cyano group, a substituted or unsubstituted alkylsilyl group having 1 to 30 carbon atoms and a substituted or unsubstituted an arylsilyl group having 6 to 30 carbon atoms, and the substituents of $R_9$ and $R_{10}$ are the same or different, and each independently selected from the group consisting of deuterium, a urethane group, a carboxyl group, a cyano group, a nitro group, a halogen group, a hydroxyl group, a carboxylate group, an alkyl group having 1 to 30 carbon atoms, an alkenyl group having 2 to 30 carbon atoms, an alkynyl group having 2 to 24 carbon atoms, a cycloalkyl group having 3 to 30 carbon atoms and a heteroalkyl group having 2 to 30 carbon atoms.

* * * * *